(12) United States Patent
Lee et al.

(10) Patent No.: US 9,597,405 B2
(45) Date of Patent: Mar. 21, 2017

(54) STAR POLYMER NANOSHELLS AND METHODS OF PREPARATION THEREOF

(71) Applicants: INTERNATIONAL BUSINESS MACHINES CORPORATION, Armonk, NY (US); SAN JOSE STATE UNIVERSITY RESEARCH FOUNDATION, San Jose, CA (US)

(72) Inventors: Victor Yee-Way Lee, San Jose, CA (US); Robert D. Miller, San Jose, CA (US); Hector H. Nuno, San Jose, CA (US); Joseph Sly, San Jose, CA (US)

(73) Assignees: International Business Machines Corporation, Armonk, NY (US); San Jose State University Research Foundation, San Jose, CA (US)

( * ) Notice: Subject to any disclaimer, the term of this patent is extended or adjusted under 35 U.S.C. 154(b) by 140 days.

(21) Appl. No.: 14/588,584

(22) Filed: Jan. 2, 2015

(65) Prior Publication Data
US 2015/0335760 A1    Nov. 26, 2015

Related U.S. Application Data

(62) Division of application No. 13/051,083, filed on Mar. 18, 2011, now Pat. No. 8,945,513.

(51) Int. Cl.
| | | |
|---|---|---|
| *A61K 49/00* | (2006.01) | |
| *A61K 47/48* | (2006.01) | |
| *A61K 9/51* | (2006.01) | |
| *G01N 33/58* | (2006.01) | |
| *A61K 49/04* | (2006.01) | |
| *A61K 49/18* | (2006.01) | |
| *B82Y 5/00* | (2011.01) | |
| *B01J 13/02* | (2006.01) | |
| *C09B 67/02* | (2006.01) | |
| *C09B 67/08* | (2006.01) | |
| *C09B 67/00* | (2006.01) | |
| *C09B 47/00* | (2006.01) | |
| *B82Y 30/00* | (2011.01) | |

(52) U.S. Cl.
CPC ...... *A61K 47/48176* (2013.01); *A61K 9/5115* (2013.01); *A61K 9/5138* (2013.01); *A61K 47/48884* (2013.01); *A61K 49/0036* (2013.01); *A61K 49/0054* (2013.01); *A61K 49/0065* (2013.01); *A61K 49/0093* (2013.01); *A61K 49/0097* (2013.01); *A61K 49/0423* (2013.01); *A61K 49/1818* (2013.01); *B01J 13/02* (2013.01); *B82Y 5/00* (2013.01); *B82Y 30/00* (2013.01); *C09B 47/00* (2013.01); *C09B 67/0005* (2013.01); *C09B 67/0032* (2013.01); *C09B 67/0097* (2013.01); *C09B 68/444* (2013.01); *C09B 68/446* (2013.01); *G01N 33/587* (2013.01); *A61K 9/5192* (2013.01); *Y10T 428/249953* (2015.04); *Y10T 428/2993* (2015.01); *Y10T 428/2998* (2015.01)

(58) Field of Classification Search
CPC  A61K 9/5115; A61K 9/5192; A61K 49/0054; A61K 49/0036; A61K 49/0065; A61K 49/0423
USPC ....... 424/426, 427, 490, 486, 9.6, 9.1, 9.322
See application file for complete search history.

(56) References Cited

U.S. PATENT DOCUMENTS

| | | |
|---|---|---|
| 6,201,099 B1 | 3/2001 | Petersen et al. |
| 6,530,944 B2 | 3/2003 | West et al. |
| 6,682,642 B2 | 1/2004 | Mikkola et al. |
| 6,685,986 B2 | 2/2004 | Oldenburg et al. |
| 6,699,724 B1 | 3/2004 | West et al. |
| 6,972,046 B2 | 12/2005 | Sun et al. |
| 7,056,455 B2 | 6/2006 | Matyjaszewski et al. |
| 7,318,892 B2 | 1/2008 | Connell et al. |
| 7,449,237 B2 | 11/2008 | Chan et al. |
| 7,560,510 B2 | 7/2009 | Wang et al. |
| 7,718,738 B2 | 5/2010 | Bohm et al. |
| 2002/0132045 A1 | 9/2002 | Halas et al. |
| 2007/0053845 A1 | 3/2007 | Sengupta et al. |
| 2007/0292495 A1 | 12/2007 | Ludwig et al. |
| 2007/0292518 A1 | 12/2007 | Ludwig |
| 2007/0298257 A1 | 12/2007 | Ludwig et al. |
| 2009/0061006 A1 | 3/2009 | Leuschner et al. |
| 2009/0246142 A1 | 10/2009 | Bhatia et al. |
| 2010/0009001 A1 | 1/2010 | Armes et al. |
| 2010/0015433 A1 | 1/2010 | Arfsten et al. |
| 2010/0099819 A1 | 4/2010 | Niitani |
| 2010/0330147 A1 | 12/2010 | Hossainy et al. |

FOREIGN PATENT DOCUMENTS

| | | |
|---|---|---|
| JP | 2008179760 A | 8/2008 |
| WO | 9522639 A2 | 8/1995 |

OTHER PUBLICATIONS

Al et al., "Magnetite-Loaded Polymeric Micelles as Ultrasensitive Magnetic-Resonance Probes", Adv. Mater. 2005, 17 p. 1949-1952. Published online: Aug. 4, 2005.
Canadian IPO, PCT/CA2012/050172 International Search Report mailed Sep. 5, 2012.
Kind, L. "Template directed synthesis of highly organized functional biomimetic silica nanostructures" Ph.D. Thesis Universitat Basel, (2009); http://edoc.unifias.ch/921/1/PhD_Thesis_Lucy_Kind jull_version.pdf.
Miller et al., "Versatile Controlled Support Achitectures for Nano-Scale Construction" Polymer Preprints 2006, 47(2), 969.
Nuno, H. "Functionalized silica nanostructures for biosensing applications", Master's Thesis San Jose State University, (2010), Paper 3883; http://scholanvorks.sjsu.edu/etd_theses/3883.
Nuno et al., "Star Polymer Templated, Dye Occluded, Functionalized Silica Nanoparticles for Optoelectronic Applications", PolymerPreprints 2010 51(1), p. 222-223, published online Feb. 17, 2010.

(Continued)

*Primary Examiner* — Micah-Paul Young
(74) *Attorney, Agent, or Firm* — Michael R. Roberts

(57) ABSTRACT

A nanoshell is disclosed, comprising a star polymer occlusion complex comprising i) an amphiphilic unimolecular star polymer having a crosslinked core covalently linked to 6 or more independent polymer arms, and ii) a cargo material occluded in the star polymer; and a shell comprising an inorganic material in contact with a peripheral surface of the star polymer occlusion complex.

23 Claims, 31 Drawing Sheets

(56) References Cited

OTHER PUBLICATIONS

Nuno et al., slides for a talk titled "Star Polymer Templated, Dye Occluded, Functionalized Silica Nanoparticles for Biomedical Applications" delivered by inventor Hector Nuno before a group at the 239th American Chemical Society National Meeting, San Francisco, Mar. 24, 2010.

Nuno, et al., Abstract for a talk titled "Star Polymer Templated, Dye Occluded, Functionalized Silica Nanoparticles for Biomedical Applications" delivered by inventor Hector Nuno before a group at the 239th American Chemical Society National Meeting, San Francisco, Mar. 24, 2010. Published online Jan. 25, 2010.

Pham, et al., "Preparation and Characterization of Gold Nanoshells Coated with Self-Assembled Monolayers", Langmuir 2002, 18, 4915-4920. Published on Web May 17, 2002.

Shi, et al., "Gold Nanoshells on Polystyrene Cores for Control of Surface Plasmon Resonance", Langmuir 2005, 21, 1610-1617, Published on Web Jan. 15, 2005.

Tjio et al., Abstract for a talk titled "Star polymer templated electroless deposition of plasmonic metal nanostructures" by inventor Melia Tjio before a group at the 239th American Chemical Society National Meeting, San Francisco, Mar. 25, 2010. Published online Jan. 25, 2010.

Tjio et al., slides for a talk titled "Star polymer templated electroless deposition of plasmonic metal nanostructures" delivered by inventor Melia Tjio before a group at the 239th American Chemical Society National Meeting, San Francisco, Mar. 25, 2010.

Tjio, et al., "Star Polymer Templated Electroless Deposition of Plasmonic Metal Nanostructures", Polymeric Materials: Science & Engineering 2010, 102, 847. Published online Mar. 16, 2010.

Tjio, M., "Tijo, M. Electroless deposition of plasmonic nanostructures on star polymer templates", Master's Thesis San Jose State University, (2010), Paper 3833; http://scholanvorks.sjsu.edu/etd_theses/3833.

USPTO, Final Office Action, mailed Apr. 23, 2014, U.S. Appl. No. 13/051,083.

USPTO, Non-Final Office Action, mailed Oct. 9, 2013, U.S. Appl. No. 13/051,083.

Wiltshire, et al., "Degradable Core Cross-Linked Star Polymers via Ring-Opening Polymerization", Macromolecules, 2006, 39 (13), 4282-4285; Publication Date (Web): Jun. 3, 2006.

Zhai, et al., "Probing the Electronic Structure and Chemical Bonding of Gold Oxides and Sulfides in $AuO_n^-$ and $AuS_n^-$ (n ) 1, 2)," J. Amer. Chem. Soc., 2008, 130, 9156-9167. Published on Web Jun. 17, 2008.

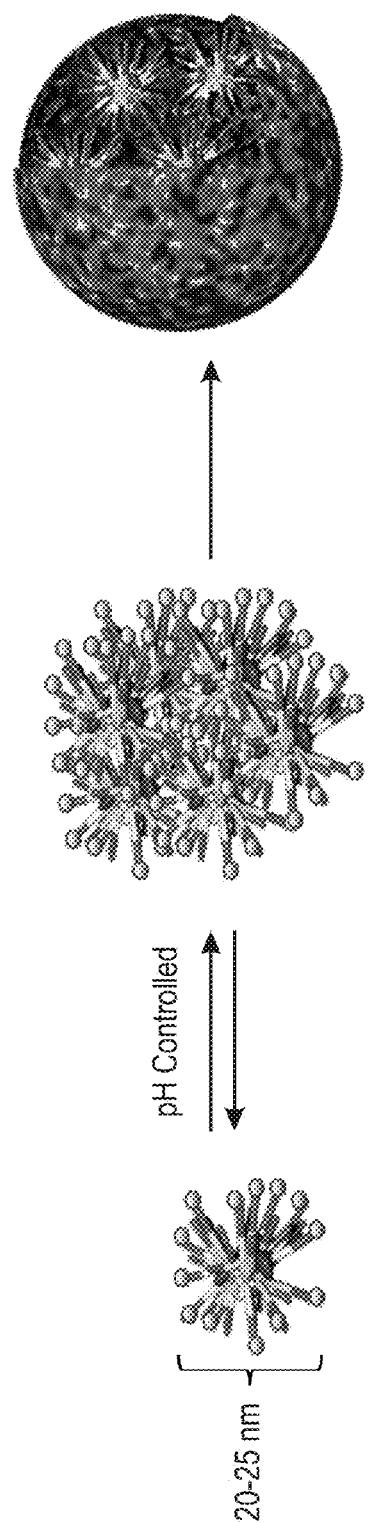

Solid Silica Particles Formed
("Two Pot" Conditions)
Without Star Polymer Template

SPIONNS-1

SPIONNS-1

STAR POLYMER NANOSHELLS AND METHODS OF PREPARATION THEREOF

CROSS REFERENCE TO RELATED APPLICATIONS

This application is a division of, and claims the benefit of, pending nonprovisional U.S. application Ser. No. 13/051,083 entitled "STAR POLYMER NANOSHELLS AND METHODS OF PREPARATION THEREOF", filed on Mar. 18, 2011, herein incorporated by reference in its entirety.

GOVERNMENT LICENSE RIGHTS

This invention was made with Government support under Agreement No. H94003-08-2-0806, awarded by the Defense Microelectronics Activity, effective Sep. 12, 2008. The Government has certain rights in this invention.

PARTIES TO A JOINT STUDY AGREEMENT

This invention was made under a joint study agreement between International Business Machines Corporation and San Jose State University Research Foundation.

BACKGROUND

The present invention relates to star polymer nanoshells and methods of preparation thereof, and more specifically to star polymers comprising gold, silica, or iron oxide in a peripheral shell, and a cargo material occluded in a core region of the star polymer.

Recently, nanoparticles of increasingly complex composition, structure and function have been developed for a wide range of applications such as bio-sensing, drug delivery, intracellular imaging and therapeutics. These include, for example, organic nanoparticles such as dendrimers, inorganic nanoparticles such as silica or transition metal-containing nanoparticles and nanoparticles comprised of composite materials. However, it is a challenge to construct structurally complex inorganic nanoparticles having an average particle diameter below 100 nanometers, and a low polydispersity.

Deposition of silica onto small nanoparticle templates has been used to produce nanoscale core shell structures. Templates include gold nanoparticles, inorganic quantum dots, or organic polymers to produce core shell structures, but nucleation sites must be incorporated onto the surface of these templates for the silica to grow and any optical properties produced are constrained to those of the nucleating template.

Additional methods and materials are needed for preparing nanoparticles comprising silicon and/or other inorganic materials, including metals.

SUMMARY

Accordingly, a nanoshell is disclosed, comprising:
a star polymer occlusion complex comprising i) an amphiphilic unimolecular star polymer having a crosslinked core covalently linked to 6 or more independent polymer arms, and ii) a cargo material occluded in the star polymer; and
a shell comprising an inorganic material in contact with a peripheral surface of the star polymer occlusion complex.

A method is disclosed, comprising:
forming a mixture of an amphiphilic unimolecular star polymer and a cargo material in a first solvent, the star polymer having a crosslinked core covalently linked to 6 or more independent polymer arms;
injecting the mixture into a second solvent, the second solvent being a non-solvent for the cargo material, thereby forming a star polymer occlusion complex, the star polymer occlusion complex comprising the cargo material occluded in the star polymer; and
depositing a shell-forming inorganic material on a peripheral surface of the star polymer occlusion complex using one or more sequential processes, thereby forming a nanoshell comprising a shell, the shell comprising one or more inorganic shell layers.

Another method is disclosed, comprising:
forming a mixture containing an amphiphilic unimolecular star polymer, a cargo material, and iron oxide nanoparticles in a suitable solvent, the star polymer having a crosslinked core covalently linked to 6 or more independent polymer arms; and
injecting the mixture into a second solvent, the second solvent being a non-solvent for the cargo material, thereby forming a nanoshell comprising the star polymer, the cargo material, and the iron oxide particles.

Also disclosed is an aqueous mixture comprising the above-described nanoshell.

Also disclosed is a method of diagnostic imaging, comprising contacting a cell with the above-described aqueous mixture.

The above-described and other features and advantages of the present invention will be appreciated and understood by those skilled in the art from the following detailed description, drawings, and appended claims.

BRIEF DESCRIPTION OF THE SEVERAL VIEWS OF THE DRAWINGS

FIG. 6A is a reaction diagram using three-dimensional drawing representations of the star polymer occlusion complex, which shows the nanoshell size (and hence properties) can be controlled by pH mediated aggregation of the star polymer occlusion complex. The size of the aggregate is a function of pH and/or solvent strength.

" in FIG. 12A. Dansyl chloride dye in FIG. 12A is another example of an organic tagging agent, serving as a representative cellular targeting agent. This demonstrates the nanoshell surface can be modified using one or more surface functionalizing agents to form one or more functionally different reactive surface groups.

DETAILED DESCRIPTION

Disclosed are nano-sized shelled particles referred to herein as nanoshells, based on the discovery that inorganic materials, including tetravalent silicon materials and/or metals, including zerovalent metal, metal oxides and other metal compounds, can be deposited in the form of shell on the peripheral surface of a star polymer and/or a star polymer occlusion complex. A star polymer occlusion complex is an independent macromolecule comprising a star polymer and a cargo material occluded therein (e.g., biologically active materials, dyes, image enhancing agents). The cargo and/or the shell can be bound non-covalently and/or covalently to the star polymer. The nanoshell can comprise a shell encompassing one or more star polymer macromolecules and/or one or more macromolecules of a star polymer occlusion complex. The shell can comprise any suitable inorganic material, organometallic material, and/or metal material. More particularly, the shell can comprise gold (e.g., as a metal and/or a salt), tetravalent silicon-containing materials (e.g., organosilicon materials, silicates, silica), iron-containing materials (e.g., as a metal, iron complexes, and/or iron oxides), which partially or wholly encapsulate the star polymer and/or star polymer occlusion complex. That is, the shell can be contiguous or non-contiguous, porous or non-porous. The nanoshells can comprise one or more shell layers comprising the same or different inorganic materials. The nanoshells are useful, for example, as carriers for gene and drug delivery, materials that can influence stem cell differentiation, and in particular as carriers for materials useful in diagnostics or cellular imaging, such as contrast enhancing agents.

Figure 1A:
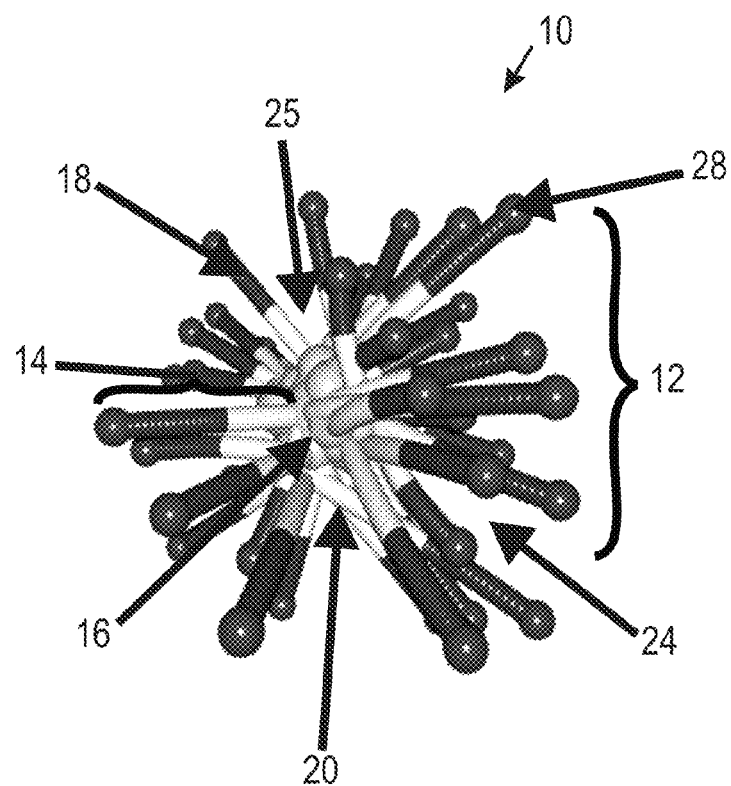
FIG. 1A is a three-dimensional drawing representation of a unimolecular star polymer.
Figure 1B:
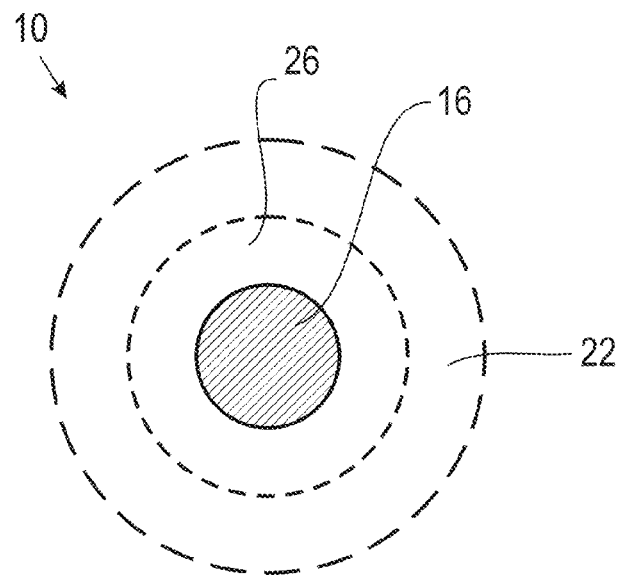
FIG. 1B is a graphical layer diagram illustrating the hydrophilic and hydrophobic sub-regions of an exemplary star polymer.

FIG. 1A is a three-dimensional drawing representation of a unimolecular star polymer 10. FIG. 1B is a graphical layer diagram illustrating the hydrophilic and hydrophobic sub-regions of star polymer 10. Star polymer 10 comprises six or more independent amphiphilic polymer arms 14. Each polymer arm 14 is covalently linked to a central crosslinked polymer core 16. Polymer core 16 can be a living core or a passive core (i.e., having no reactive groups to introduce additional functionality). Polymer core 16 can be either hydrophobic or hydrophilic. In this example, each polymer arm 14 comprises a peripheral hydrophilic chain segment 18 (dark tone in FIG. 1A) and an inner hydrophobic chain segment 20 (white tone in FIG. 1A). Region 12 comprises the collection of polymer arms 14. In this example, region 12 has two sub-regions: a peripheral hydrophilic sub-region 22 (FIG. 1B) comprising the peripheral hydrophilic chain segments 18 and peripheral interstitial areas 24 (FIG. 1A), and an inner hydrophobic sub-region 26 (FIG. 1B) composed of the inner hydrophobic chain segments 20 and inner interstitial areas 25 (FIG. 1A). The dashed boundary lines around peripheral sub-region 22 and inner sub-region 26 in FIG. 1B indicate the boundary between peripheral interstitial areas 24 and inner interstitial areas 25.

FIGS. 1A and 1B depict one example of an architecture for generating water compatible nanoshells. The hydrophilic and hydrophobic sub-regions, chain segments, and interstitial spaces can be reversed if desired. No restriction is placed on the number of the hydrophilic regions or the number of hydrophobic regions in the polymer arms (e.g., hydrophilic blocks and hydrophobic blocks of a block copolymer arm). The star polymer can comprise one or more hydrophilic regions and/or one or more hydrophobic regions, if desired. No restriction is placed on the arrangement of the hydrophilic regions or the number of hydrophobic regions. The peripheral region of the star polymer arm can be hydrophobic or hydrophilic. The inner most region of the polymer arm adjacent to the crosslinked star polymer core can be hydrophilic or hydrophobic. The peripheral sub-region 22, the inner sub-region 26, and/or the crosslinked polymer core 16 can also contain specific sites for further functionalization, which can be useful in controlling chemical interactions that favor the binding of, or the release of, an occluded cargo material. As a non-limiting example, the polymer core 16 can be a living core capable of initiating a polymerization or undergoing a different chemical modification. As another non-limiting example, the polymer arms 14 can comprise a functionally useful end group 28, such as a galactose moiety capable of selective recognition of liver cells.

The amphiphilic arms and the polymer core can be formed by polymerization of a vinyl monomer, or by ring opening polymerization of a cyclic carbonyl monomer.

Figure 1C:
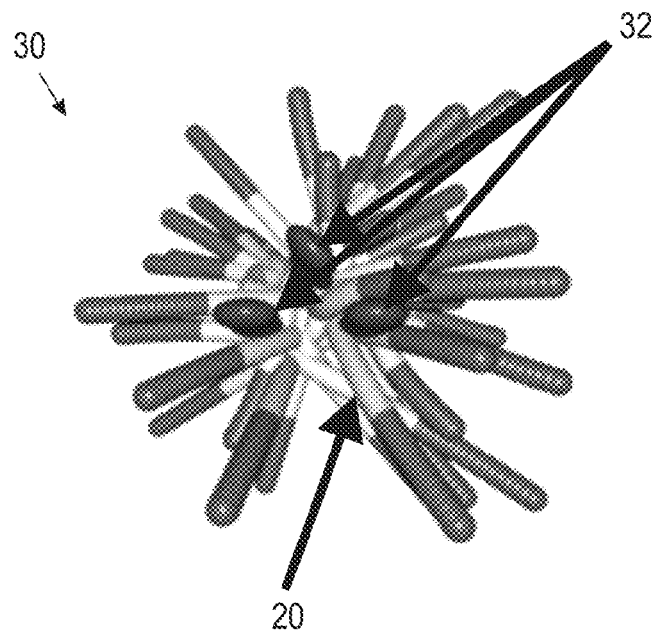
FIG. 1C is a three-dimensional drawing representation of an exemplary star polymer occlusion complex, comprising three occluded particles or molecules. The occluded material can be a pharmaceutical agent, image contrast agent, chromophore or material selected to form an occlusion complex having a desired dielectric constant.

FIG. 1C is a three-dimensional drawing representation of an exemplary star polymer occlusion complex 30, comprising three occluded particles 32 occluded in star polymer 10. Each occluded particle 32 can comprise one or more molecules of an occluded material. In the example shown, the occluded material is in contact with the inner hydrophobic chain segments 20 of star polymer 10 but may also reside to some extent in contact with the outer hydrophillic segments 18. In an embodiment, the occluded material is a porphyrinoid, and the porphyrinoid is not in an aggregated state.

The shell can be in the form of a contiguous or noncontiguous layer. The shell can be porous or non-porous. The shell can comprise independent nanoparticles of a material dispersed in the peripheral interstitial areas 24 of a star polymer molecule. A shell can encompass one or more macromolecules of star polymer and/or star polymer occlusion complex. The general term "shell" includes any of these types of deposited inorganic layers, or a combination thereof, which are further illustrated in FIGS. 1D to 1G.

Figure 1D:
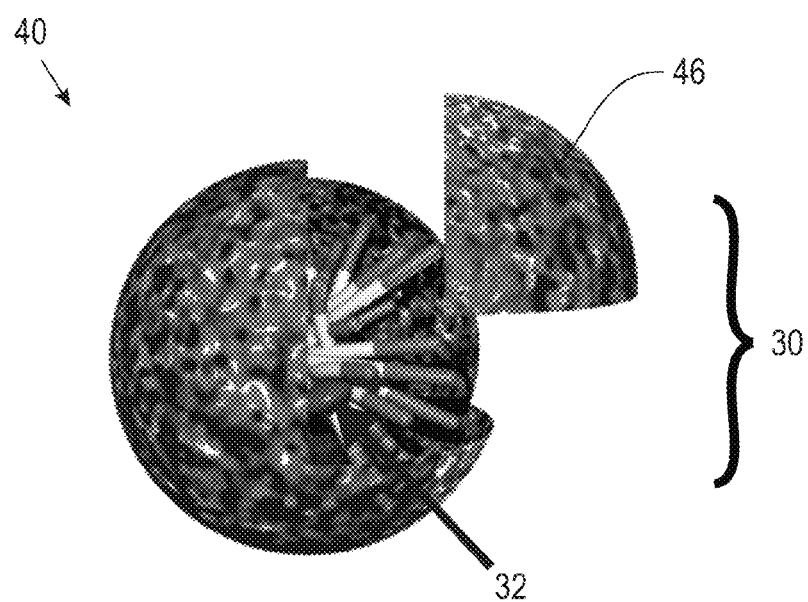
FIG. 1D is a three-dimensional drawing representation of an exemplary star polymer nanoshell comprising a contiguous peripheral shell disposed on a star polymer occlusion complex. A portion of the shell has been removed to reveal the contained star polymer occlusion complex.

FIG. 1D is a three-dimensional drawing representation of an exemplary nanoshell 40 comprising a contiguous shell 46 disposed on a unimolecular star polymer occlusion complex. The shell is partially removed to show the star polymer occlusion complex 30 comprising occluded cargo material 32 (e.g., a molecule of a dye).

Figure 1E:
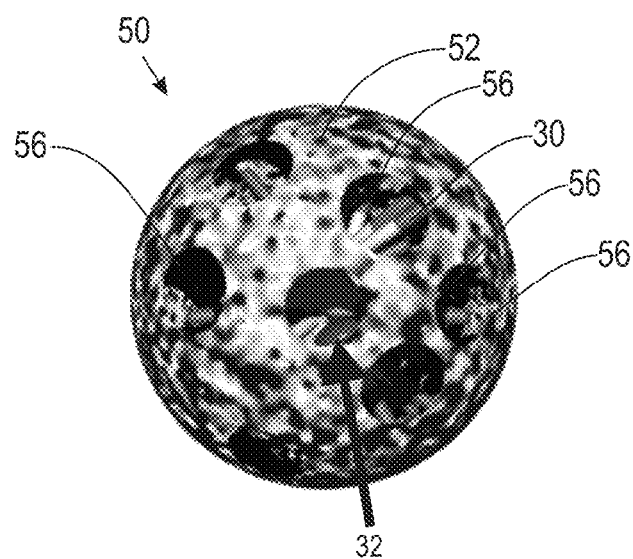
FIG. 1E is a three-dimensional drawing representation of an exemplary star polymer nanoshell comprising a porous peripheral shell.

FIG. 1E is a three-dimensional drawing representation of an exemplary nanoshell 50 comprising a shell 52 having pores 56. The star polymer occlusion complex 30 comprising occluded cargo material 32 is partially visible within pores 56.

Figure 1F:
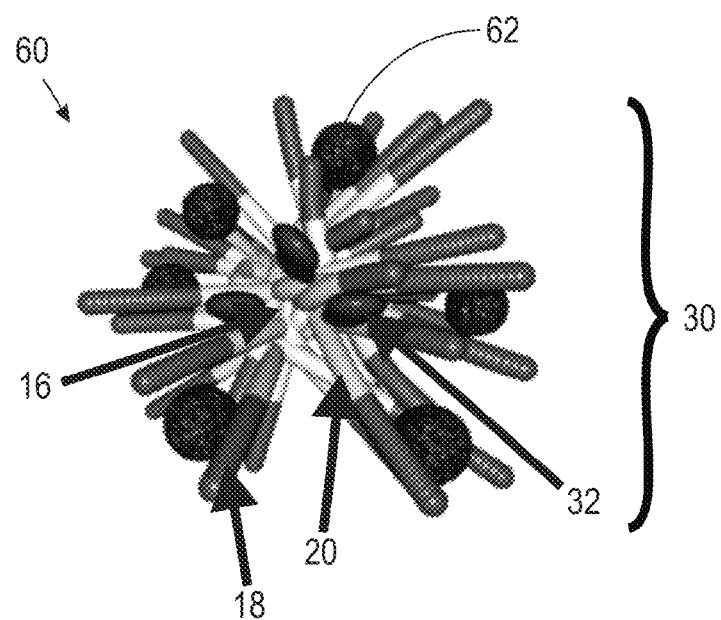
FIG. 1F is a three-dimensional drawing representation of an exemplary star polymer nanoshell comprising a non-contiguous shell comprised of independent inorganic nanoparticles dispersed in the peripheral interstitial spaces of a star polymer occlusion complex.

FIG. 1F is a three-dimensional drawing representation of an exemplary nanoshell 60 comprising independent nanoparticles 62 dispersed in the peripheral interstitial space 24 of the star polymer occlusion complex 30. Inorganic particles 62 are in contact with peripheral hydrophilic chain segments 18 of polymer arms 14 (see FIG. 1A). Occluded cargo material 32 is associated with inner hydrophobic chain segments 20 and/or core 16.

Figure 1G:
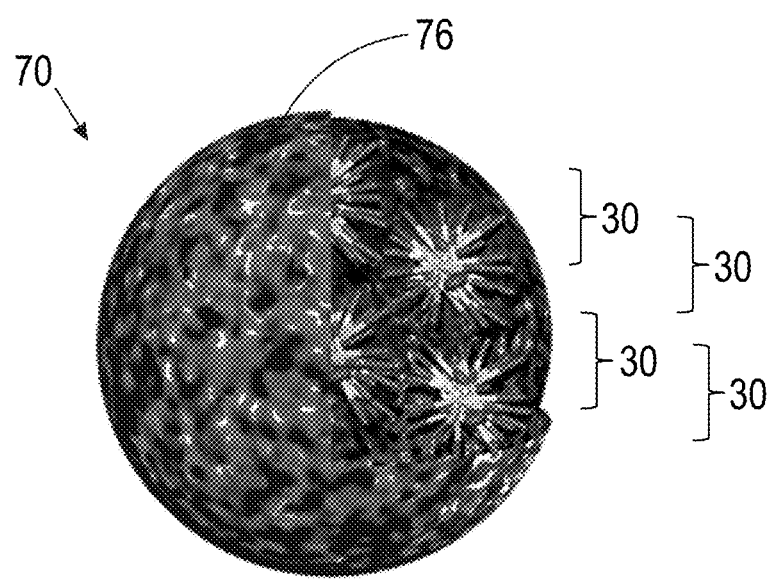
FIG. 1G is a three-dimensional drawing representation of an exemplary star polymer nanoshell comprising a shell that encompasses more than one macromolecule of a star polymer occlusion complex. Each star polymer occlusion complex is an independent macromolecular structure.

FIG. 1G is a three-dimensional drawing representation of an exemplary nanoshell 70, comprising shell 76 encompassing multiple independent macromolecules of star polymer occluded complex 30. In this example, the shell is partially removed to reveal four macromolecules of the star polymer occluded complex 30 contained therein.

The above examples of shells are meant to be illustrative and non-limiting. The hydrophilic chain segments comprise functionality for covalently or non-covalently binding the shell material. The shell material can reside partially or wholly in the peripheral interstitial areas 24. Alternatively, the shell material can be covalently or non-covalently bound, by one or more of the hydrophilic chain segments, as depicted in FIG. 1D.

Herein, "restricted metals" include ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium. In an embodiment, the chemical formula of a star polymer used to prepare a star polymer occlusion complex contains none of the above restricted metals. In another embodiment, each one of the above restricted metals has a concentration in a star polymer used to prepare a star polymer occlusion complex of 0 parts per million to 100 parts per million (ppm), 0 parts per billion to 100 parts per billion (ppb), or 0 parts per trillion to 100 parts per trillion (ppt). Preferably, each one of the above restricted metals has a concentration in a star polymer used to prepare a star polymer occlusion complex that is below detection limits. No restriction is placed on the concentration of boron, silicon, or any individual alkali metal in the chemical formula of a star polymer used to prepare a star polymer occlusion complex, as long as the star polymer and the star polymer occlusion complex have desirable properties, such as amphiphilic properties. The cargo material and/or an inorganic material used in forming a shell can comprise a restricted metal.

The cargo material can be bound covalently or non-covalently to the star polymer. Non-covalent interactions include hydrophobic and/or ionic interactions. The cargo material does not have to be released from the star polymer occlusion complex in order to perform a useful function. The cargo material can perform a useful function while bound to the star polymer or after release from the star polymer.

Preferably, the star polymer occlusion complex can be dispersed in aqueous solution in the form of nano-sized particles. Cargo materials include biologically active substances. Exemplary biologically active substances include biomolecules (e.g., DNA, genes, peptides, proteins, enzymes, lipids, phospholipids, and nucleotides), natural or synthetic organic compounds (e.g., drugs, dyes, synthetic polymers, oligomers, and amino acids), inorganic materials (e.g., metals and metal oxides), chromophores that aid in diagnostics (e.g., porphyrinoid compounds, including porphyrins and phthalocyanines), radioactive variants of the foregoing, and combinations of the foregoing. Some of the biologically active substances can alter the chemical structure and/or activity of a cell, or can selectively alter the chemical structure and/or activity of a cell type relative to another cell type. As an example, one desirable change in a chemical structure can be the incorporation of a gene into the DNA of the cell. A desirable change in activity can be the expression of a transfected gene. Another change in cell activity can be the induced production of a desired hormone or enzyme. A desirable change in cell activity can also be the selective death of one cell type over another cell type. No limitation is placed on the relative change in cellular activity caused by the biologically active substance, providing the change is desirable and useful. Other biologically active materials herein improve diagnostic capability without necessarily altering the structure or activity of the tissue, organ, bone, or cell. These include image contrast enhancing agents for magnetic resonance imaging and x-ray imaging. The cargo material can comprise a metal, including one or more of the above-described restricted metals.

The term "biodegradable" is defined by the American Society for Testing and Materials as a degradation caused by biological activity, especially by enzymatic action, leading to a significant change in the chemical structure of the material. For purposes herein, a material is biodegradable if it undergoes 60% biodegradation within 180 days in accordance with ASTM D6400.

The star polymers used to prepare star polymer occlusion complexes are amphiphilic materials. Herein, an amphiphilic material is a material that can be dispersed in an aqueous mixture in the form of nano-sized particles having a circular cross-sectional diameter of 2 nm to 1500 nm. The star polymers are represented by the general formula (1):

(1)

wherein the wavy line represents the crosslinked polymer core (i.e., core), and each T' is an independent polymer arm covalently linked to the core. The star polymer comprises w' polymer arms T', wherein w' is greater than or equal to 6. The star polymer has a particle size of about 2 nm to about 150 nm. Each of the 6 or more polymer arms comprises a hydrophilic polymer chain segment and a hydrophobic polymer chain segment. The polymer arms can independently comprise an optional side chain polymer (i.e., a polymer pendant to the backbone of the polymer arm, also referred to herein as the second polymer). The polymer arms can independently also comprise a side chain functional group selected from the group consisting of urea groups, carboxylic ester groups, carboxylic acid groups, carboxylic acid salts, latent carboxylic acid groups, quaternary amine groups, tertiary amine groups, secondary amine groups, primary amine groups, azides, alkynes, poly(alkylene ether) groups, and combinations thereof. The 6 or more polymer arms can independently be living polymer arms, and the core can independently be a living core. The polymer arms and the core can independently comprise a homopolymer, random copolymer, block copolymer, or combinations thereof.

The polymer arm can comprise a polymer chain segment comprising a nitrogen-containing backbone. Exemplary nitrogen-containing backbones include poly(alkylene imine)s having the formula —(—(CH$_2$—CH$_2$)$_m$—N(R)—)$_n$, wherein R is alkyl or another substituent (e.g., a substituent comprising a carbonyl group attached to the backbone nitrogen, and the like). The number average molecular weight of the polyamine chain segment can be from 100 to 100,000, more specifically 100 to 10000, and even more specifically, 100 to 5000.

Star polymers as defined above preferably have a peripheral region containing sites for interaction with inorganic materials. These structures provide suitable scaffolds for the formation of inorganic nanoshells. If desired, the star polymer core and inner regions of the polymer arms can provide sites for interaction with inorganic materials. In addition to this, the star polymer can be biodegradable or partially biodegradable. The ROP star polymers described further below provide specific but non-limiting examples of this.

Star Polymers Prepared by Vinyl Polymerizations.

Vinyl polymerization methods are well known and include but are not limited to free radical polymerizations, living anionic addition polymerizations, and living free radical polymerizations (e.g., nitroxide mediated radical polymerization (NMP), atom radical transfer Polymerization (ATRP), and reversible addition-fragmentation chain transfer (RAFT)).

Exemplary vinyl monomers include styrene and substituted styrenes, divinylbenzene and substituted divinylbenzenes, (meth)acrylate esters, ethylene glycol di(meth)acrylates, (meth)acrylamides, acrylonitrile, vinyl acetate, vinyl chloride, ethene, propene, and butadiene. Other vinyl monomers will be readily apparent to those skilled in the polymer art.

ATRP polymerizations are typically initiated by an alkyl halide and catalyzed by a transition metal. The reaction is illustrated in Scheme 1 with the polymerization of styrene using copper(I) bromide as the catalyst, ethyl 2-bromo-2-methylpropionate as the initiator, and N,N,N',N,N pentamethyldiethylenetriamine (PMDETA) as a stabilizing ligand.

Scheme 1

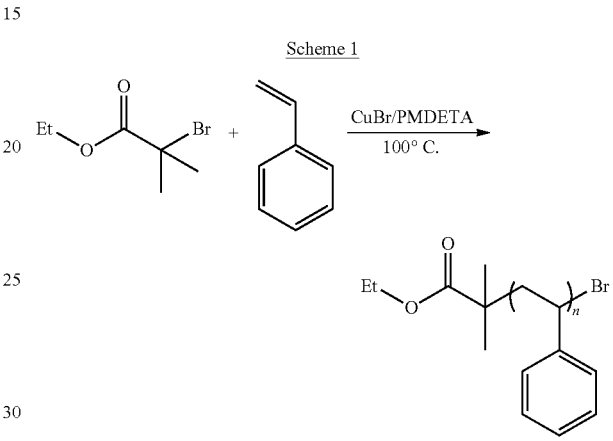

ATRP produces polymers having narrow molecular distributions, but the metal catalyst can be cytotoxic and difficult to remove. Common monomers for ATRP include (meth)acrylates, (meth)acrylamides, acrylonitrile, and styrenes.

Anionic addition polymerizations of vinyl monomers (e.g., styrene, propene, butadiene), are typically initiated by nucleophilic alkyllithium compounds, Grignard reagents, metal alkoxides and metal hydroxides. The resulting anionic living polymers generally have low polydispersities but are non-biodegradable.

Star Polymers Prepared by Ring Opening Polymerization.

In an embodiment, the star polymers are biodegradable. Preferably, these star polymers have a polydispersity index of 1.35 or less. The biodegradable star polymers are preferably formed using a polymerization method that involves the use of an organocatalyst rather than a catalyst whose chemical formula comprises a restricted metal. In an embodiment, the core of the star polymer includes 6 or more sites capable of further synthetic transformation, the sites including a functional group selected from the group consisting of alcohols, amines, carboxylic acids, azides, alkynes, alkenes, halogen groups, and combinations thereof.

The biodegradable star polymers are preferably derived by ring opening polymerization of one or more cyclic carbonyl monomers using organocatalysis to form the polymer arms and the core. The chemical formula of an organocatalyst comprises none of the above described restricted metals, including ionic and non-ionic forms of the restricted metal. The star polymers produced using an organocatalyst by ROP methods preferably contain no more than 100 ppm of any single restricted metal.

Star polymers formed by organocatalyzed ring opening polymerizations of cyclic carbonyl monomers have been found to have narrower molecular weight distributions (i.e., lower polydispersity indexes) compared to star polymers formed by ring opening polymerization with a metal based polymerization catalyst. The molecular weight distributions are also narrower than star polymers prepared by free radical polymerizations (FRP). The star polymers formed by ring opening polymerization are biodegradable, and they can be more biocompatible materials (i.e., non-immunogenic, non-cytotoxic material) due to lower levels of metal contaminants arising from a polymerization catalyst. In addition, sequential ROP polymerizations can be conducted in some instances in a single vessel.

In one process of forming a star polymer, the polymer arms are prepared first, followed by the core, wherein the formation of the crosslinked core conjoins six or more amphiphilic polymer arms. In an embodiment, a polymer arm T' has the general formula (2):

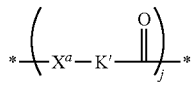
(2)

wherein the asterisk on the left of $X^a$ indicates the attachment point, or bond, to the core. Each P' is a monovalent radical representing a peripheral hydrophilic polymer chain segment of the polymer arm, and is derived from a first polymer. The first polymer can be prepared by ring opening polymerization or by another type of polymerization. P' can further comprise a substituent group selected from the group consisting of urea groups, carboxylic acid groups, carboxylic acid salts, latent carboxylic acid groups, quaternary amine groups, tertiary amine groups, secondary amine groups, primary amine groups, azides, alkynes, poly(alkylene ether) groups, and combinations thereof. In formula (2), the moiety

is a divalent radical comprising the hydrophobic chain segment of the polymer arm, and is derived by ring opening polymerization of one or more cyclic carbonyl monomers. The starred bond on the right side of the carbonyl represents the attachment point to P'. Each $X^a$ is a divalent radical independently selected from the group consisting of —O—, —NH—,

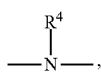

and —S—, wherein $R^4$ is a monovalent radical comprising 1 to 30 carbons. K' is a divalent radical comprising 1 to 10 backbone carbons linking $X^a$ to the carbonyl group. Each j is independently an integer greater than 1, more particularly greater than or equal to 4, and even more particularly greater than or equal to 10. Subscript j is chosen so as to achieve the desired hydrophobic/hydrophilic balance in the polymer arm, which depends on the backbone type of hydrophilic chain segment, the average molecular weight of the hydrophilic chain segment, and the cyclic carbonyl monomer or monomers used to prepare the hydrophobic chain segment. K' can further comprise a functional side chain group F'. The hydrophobic chain segment comprises a backbone selected from the group consisting of polyesters, polycarbonates, polyureas, polycarbamates, polythiocarbamates, polydithiocarbamates, and combinations thereof, which have a repeat structure as shown in (Table 1):

TABLE 1

| Polyester | |
| Polycarbonate | |
| Polyurea | |
| Polycarbamate | |
| Polythiocarbamate | |
| Polythiocarbonate | |
| Polydithiocarbonate | |

More particularly, a polymer arm has the general formula (3):

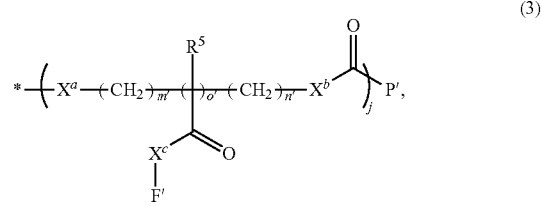
(3)

wherein $X^a$, j, and P' are defined as above. $X^b$ and $X^c$ are each divalent radicals independently selected from the group consisting of —O—,

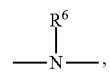

—NH—, and —S—, wherein each $R^6$ is independently hydrogen or a monovalent hydrocarbon radical comprising 1 to 30 carbons. Each $R^5$ is independently hydrogen or a monovalent hydrocarbon radical comprising 1 to 30 carbons. Each m' and n' is independently zero or an integer from 1 to 5. Each o' is independently zero or an integer from 1 to 3. Each functional group F' is independently a monovalent radical comprising from 0 to 10000 carbons. Subscripts m', n', and o' together cannot be zero within the same repeat unit. Each functional group F' can independently comprise a non-polymeric group or a polymeric group, referred to herein as an optional second polymer. The optional second polymer can be derived by ring opening polymerization or another type of polymerization.

In one embodiment, each $X^a$ and each $X^b$ is oxygen, m' and n' are each independently an integer from 1 to 3, and o' is zero or 1. In another embodiment, XC is oxygen, and F' is methyl or ethyl. In another embodiment, F' comprises a second polymer. In still another embodiment, the second polymer comprises a polyether chain. In another embodiment, P' comprises a polymer backbone selected from the group consisting of polyester, polycarbonate, and combinations thereof.

Scheme 2 illustrates the preparation of a biodegradable amphiphilic star polymer by ring opening polymerization, wherein a Polymer Arm Precursor is prepared first, followed by the Polymer Core.

In this example mono methyl end capped poly(ethylene glycol) (First Polymer, MPEG) initiates polymerization of trimethylene carbonate (TMC) in the presence of a suitable organocatalyst, thereby producing the Polymer Arm Precursor. In this instance, the Polymer Arm Precursor is a living block copolymer comprising a hydrophobic polycarbonate backbone segment derived from TMC. This segment has a terminal hydroxyl group capable of initiating a ring opening polymerization. The ring opening polymerization of BOD initiated by the Polymer Arm Precursor produces the Polymer Core, conjoining six or more of the Polymer Arm Precursors, thereby forming the Star Polymer. In this instance, the Polymer Core is a highly crosslinked living network comprising a polyester repeat structure, and further comprising six or more sites (terminal hydroxy groups) for further functionalization or ring opening polymerization if desired. The subscripts y and z indicate the relative moles of

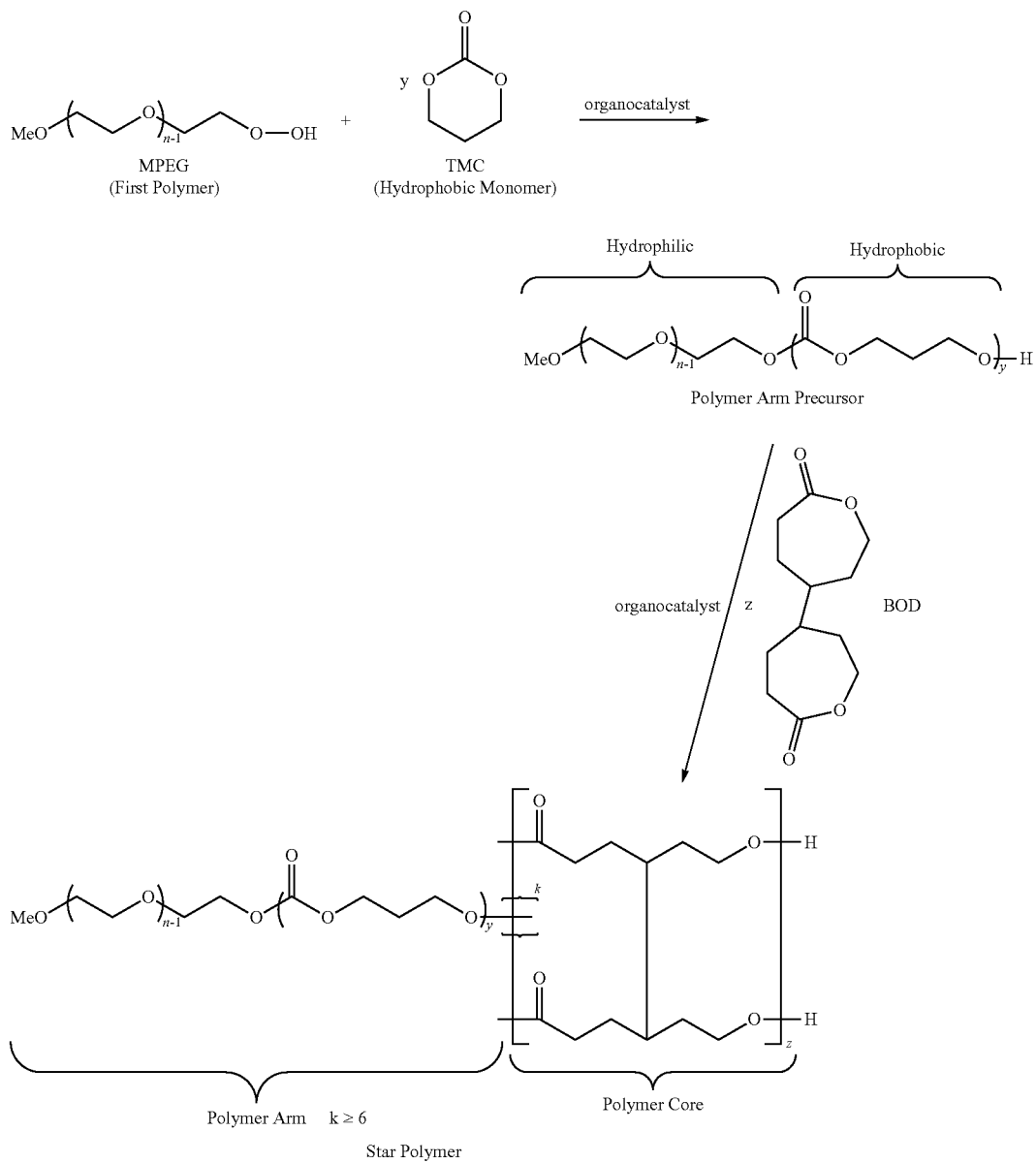

monomer used to make the Star Polymer. The subscript k is an integer greater than or equal to 6 and represents the number of Polymer Arms in the Star Polymer.

Thus, a method (Method 1) of preparing a polymer arm precursor comprises agitating a mixture comprising a first polymer, a first cyclic carbonyl monomer, an organocatalyst comprising no structural metal, an optional accelerator, and an optional solvent, thereby forming the polymer arm precursor by ring opening polymerization of the cyclic carbonyl monomer. The polymer arm precursor is a living polymer and comprises a hydrophilic chain segment, a hydrophobic chain segment, and an initiator group for ring opening polymerization. Herein, the polymer arm precursor is also referred to as a polymeric initiator for ring opening polymerization of a core precursor material.

In a method (Method 2) of forming a star polymer, which can involve one or more of the above-described polymerization techniques, a mixture comprises: i) a polymer arm precursor comprising an initiator group for polymerization, the arm precursor also comprising a hydrophobic polymer chain segment and a hydrophilic polymer chain segment, ii) a core precursor material comprising two or more polymerizable groups, iii) an organocatalyst, iv) an optional accelerator, and v) an optional solvent. The mixture is agitated, thereby forming an amphiphilic star polymer by polymerization of the core precursor material; wherein the star polymer comprises a crosslinked living polymer core derived from the core precursor material, the star polymer comprises 6 or more independent polymer arms covalently linked to the core, the 6 or more polymer arms being derived from the polymer arm precursor, and the star polymer contains no more than 100 ppm of any single restricted metal. In an embodiment, the core precursor material comprises two or more polymerizable cyclic carbonyl groups, and the polymer core is formed by ring opening polymerization of the two or more cyclic carbonyl groups. In an embodiment, each of the 6 or more polymer arms comprises a peripheral hydrophilic chain segment, and a hydrophobic chain segment located nearest the polymer core. In another embodiment, each of the 6 or more polymer arms comprises a peripheral hydrophobic chain segment, and a hydrophilic chain segment located nearest the polymer core. In another embodiment, the polymeric initiator comprises a backbone segment derived by ring opening polymerization of one or more cyclic carbonyl monomers. In another embodiment, the polymeric initiator comprises a backbone segment comprising a poly(alkylene oxide). In another embodiment, the organocatalyst comprises a nitrogen base comprising three or more nitrogens.

As shown above in Scheme 1, the polymer arm precursor is a free polymer chain as opposed to the 6 or more polymer arms of the star polymer, which are covalently linked to the polymer core. Initiation of ring opening polymerization of the core precursor material by the polymer arm precursors causes the polymer arm precursors to be conjoined by the growing crosslinked polymer core network. The core precursor material and the cyclic carbonyl monomer can each comprise a functional group selected from the group consisting of cyclic esters, cyclic carbonates, cyclic ureas, cyclic carbamates, cyclic thiocarbonates, cyclic thioureas, cyclic dithiocarbonates, and combinations thereof. In an embodiment, the core precursor material and the cyclic carbonyl monomer each comprise a functional group selected from the group consisting of cyclic esters, cyclic carbonates, and combinations thereof. In another embodiment, the first polymer is a mono end capped poly(alkylene glycol). In another embodiment, the method is performed in a single reaction vessel without isolating the polymer arm precursor.

In another method (Method 3) of preparing a biodegradable amphiphilic star polymer, the polymer arms are completed after formation of the polymer core. The method comprises agitating a first mixture comprising a first polymer comprising a protected functional group and an non-protected initiator group, a core precursor material comprising two or more polymerizable groups, an organocatalyst, an optional accelerator, and an optional solvent, thereby forming a protected first star polymer by polymerization of the core precursor material. The protected star polymer comprises a crosslinked polymer core and 6 or more independent first polymer arms comprising a protected functional group. The protected functional group of each of the 6 or more first polymer arms is then deprotected, thereby forming a second star polymer comprising 6 or more independent second polymer arms. The deprotected functional group of the 6 or more independent second polymer arms can be an initiator group suitable for extending the second polymer arms by polymerization. Alternatively, the deprotected functional group can be converted to an active leaving group useful in extending the second polymer arms, for example by a nucleophilic displacement reaction. The resulting star polymer comprises 6 or more independent polymer arms covalently bound to the polymer core, the polymer arms comprising a hydrophobic polymer chain segment and a hydrophilic polymer chain segment.

The protected functional group of the first polymer arms can be in the form of a protected alcohol, protected amine, or protected thiol group, which when deprotected forms an alcohol, amine, or thiol, respectively. The deprotected initiator group is preferably in the terminal subunit of each of the 6 or more deprotected second polymer arms.

In the above-described methods, the hydrophilic chain segment of a polymer arm can be located at a peripheral end of each of the 6 or more polymer arms, as illustrated in FIG. 1A. Alternatively, the hydrophobic chain segment can be located at the peripheral end of each of the 6 or more polymer arms. This is illustrated in the molecular models of FIG. 2A and FIG. 2B, wherein star polymer 40 comprises a shell 42 composed of six or more independent amphiphilic polymer arms 44, each of which is covalently linked to a central polymer core 46. A polymer arm comprises a peripheral hydrophobic chain segment 48 and an inner hydrophilic chain segment 50. Shell 42 has two regions, a hydrophobic outer shell region 56 (FIG. 2B) comprising peripheral hydrophobic chain segments 48 and interstitial region 54 (FIG. 2A), and a hydrophilic inner shell region 52 composed of the hydrophlic inner chain segments 50 and interstitial region 54. The dashed boundary lines around inner shell region 52 and outer shell region 56 in FIG. 2B indicate the interstitial area is shared by the outer and inner shell regions. The polymer core 46 can be either hydrophobic or hydrophilic. The outer shell region 56, the inner shell region 52, and/or the polymer core 46 can further contain specific sites useful in controlling chemical interactions that favor the binding of, or the release of, a biologically active cargo material. For example, the polymer core 46 can be a living core, capable of initiating a polymerization or undergoing a different chemical modification. As another non-limiting example, the polymer arms 44 can comprise a functionally useful end group 58, such as a galactose moiety capable of selective recognition of liver cells.

A more specific method (Method 4) of preparing a polymer arm precursor comprises agitating a reaction mixture comprising one or more hydrophobic cyclic carbonyl monomers, a hydrophilic first polymer comprising a ROP initiator group, an organocatalyst comprising no structural metal, an optional accelerator, and an optional solvent, thereby forming a polymer arm precursor by ring opening polymerization. The polymer arm precursor is a living polymer, comprising an initiator group for ring opening polymerization. The polymer arm precursor comprises a hydrophobic chain segment derived from the one or more hydrophobic cyclic carbonyl monomers, and a hydrophilic chain segment derived from the first polymer. In an embodiment, the first polymer is a mono-end capped poly(alkylene glycol). In another embodiment, the first polymer is a poly(alkylene ether) comprising a protected amine end group and a non-protected hydroxyl end group. The hydroxyl end group is an initiator group for ring opening polymerization. In another embodiment, the first polymer comprises a mono end capped poly(ethylene glycol) or a mono end capped poly(propylene glycol).

The polymer arm precursor can be chemically modified to introduce additional functionality after the ring opening polymerization. For example, the reaction mixture can comprise one or more latent hydrophobic cyclic carbonyl monomers, that is, a cyclic carbonyl monomer from which a hydrophobic repeat unit can be derived by a chemical transformation after the ring opening polymerization. Similarly, a latent hydrophilic cyclic carbonyl monomer is one from which a hydrophilic repeat unit can be derived by a chemical transformation after the ring opening polymerization.

In another method (Method 5) of preparing a polymer arm precursor, the hydrophilic and hydrophobic chain segments of the polymer arm precursor are each derived by a ring opening polymerization. The method comprises agitating a first mixture comprising one or more hydrophilic cyclic carbonyl monomers, an organocatalyst comprising no structural metal, an optional accelerator, and an initiator, thereby forming a first polymer by ring opening polymerization, wherein the first polymer comprises an initiator group for ring opening polymerization. A second mixture is formed comprising the first polymer, one or more hydrophobic cyclic carbonyl monomers, an optional second organocatalyst comprising no structural metal, an optional second accelerator, and an optional second solvent. The mixture is agitated, thereby forming a polymer arm precursor, wherein the polymer arm precursor comprises a hydrophobic chain segment derived from the one or more hydrophobic cyclic carbonyl monomers, and a hydrophilic chain segment derived from the first polymer. The first mixture can include one or more latent hydrophilic cyclic carbonyl monomers, and the second mixture can include one or more latent hydrophobic cyclic carbonyl monomers. The polymerizations can be performed in reverse order.

When the hydrophilic chain segment and the hydrophobic chain segment are each formed by a ring opening polymerization, the hydrophilic chain segment and the hydrophobic chain segment can comprise repeat units derived from the same or different cyclic carbonyl monomers. The hydrophilic chain segment and the hydrophobic chain segment can independently comprise a backbone segment selected from the group consisting of polycarbonates, polyesters, polyureas, polycarbamates, polythiocarbamates, polythiocarbonates, polydithiocarbonates, and combinations thereof.

The side chain groups and/or the end unit of the polymer arm or the polymer arm precursor can be further chemically functionalized after formation in order to control, for example, hydrophilic/hydrophobic balance, water dispersibility, cell membrane recognition properties, binding properties with respect to a given cargo material, and/or release properties for a given cargo material.

The polymer arm, the polymer arm precursor, and the optional second polymer can independently comprise an optional end cap group (ECG). End cap groups can impart stability and useful functionality to the final structure. End capping agents are numerous, and methods of their use are well established in the polymer art. End capping agents can be selected based on the functionality desired and their intended use. In an embodiment, the optional end cap group comprises a moiety selected from the group consisting of alkyl ester groups, aryl ester groups, poly(alkylene ether) groups (e.g., poly(alkylene oxide)), thiol groups, amine groups, carboxylic acid groups, quaternary amine groups, functional groups capable of targeting specific cell types, and combinations thereof. In an embodiment, the polymer arm comprises a peripheral end group comprising a galactose moiety for targeting liver cells. In another embodiment, the peripheral end group comprises a mannose moiety for binding mannose-specific proteins. In another embodiment, the peripheral end group comprises a quaternary amine.

The core precursor material for the ring opening polymerization can be a monomer, oligomer or a polymer comprising two or more polymerizable cyclic carbonyl moieties. More specifically, the core precursor material comprises two or more functional groups selected from the group consisting of cyclic esters, cyclic carbonates, cyclic carbamates, cyclic ureas, cyclic thiocarbamates, cyclic dithiocarbonates, and combinations thereof. Non-limiting examples of core precursor materials include bis-cyclic esters, bis-cyclic carbonates, bis-cyclic carbamates, bis-cyclic ureas, bis-cyclic thiocarbamates, and bis-cyclic dithiocarbonates. Exemplary bis-cyclic esters include but are not limited to:

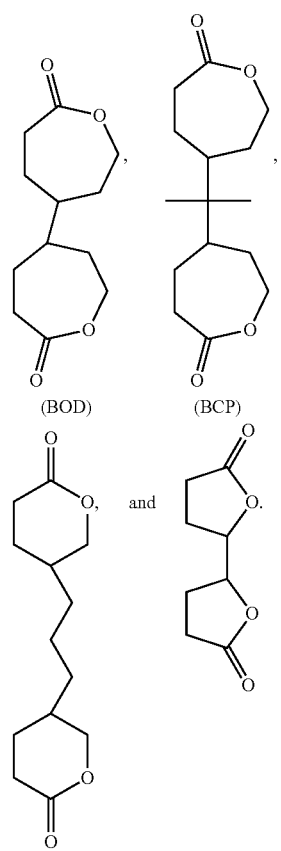

For simplicity, all examples herein assume the ideal case that all initiating groups react and, therefore, the length of polymeric blocks may be described by the division of the number of moles of monomer units (e.g., x, y, z, etc.) by the number of moles of initiating sites. However, the reaction of 100% of the initiating sites is not a requirement for successful implementation of the invention. Non-reacted nucleophilic initiating groups can serve as additional reaction or initiator sites during subsequent synthetic processes. Therefore, it is advantageous that a high percentage of the nucleophilic initiating groups undergo the ring opening reaction.

The above reaction illustrated in Scheme 2 is not meant to be restrictive. For example, the reaction of TMC can be followed by a sequential ring opening polymerization of a different hydrophobic cyclic carbonyl monomer, thereby forming a hydrophobic chain comprising a block copolymer derived from one or more hydrophobic cyclic carbonyl monomers. As stated above, the end cap group of the first polymer and/or the hydrophilic chain segment is optional. In addition, the hydrophilic chain segment or the hydrophobic chain segment can comprise a functional group selected from the group consisting of urea groups, carboxylic acid groups, carboxylic acid salts, latent carboxylic acid groups, quaternary amine groups, tertiary amine groups, secondary amine groups, primary amine groups, azides, alkynes, poly(alkylene ether) groups, and combinations thereof, with the proviso that the water dispersibility and carrier properties of the star polymer are not adversely affected.

Polyethers.

A polyether chain can provide an important means of introducing hydrophilicity into the star polymer. As stated above, a mono end capped polyether alcohol (e.g., poly(alkylene glycol) can be employed as an initiator for ring opening polymerization of a cyclic carbonyl monomer, thereby introducing a main chain hydrophilic block into the resulting polymer arm precursor.

The polyether alcohol can be a poly(alkylene glycol) of the general formula (4):

$$HO-[C(R^7)_2(C(R^7)_2)_{a'}C(R^7)_2O]_n-H \qquad (4),$$

wherein a' is 0 to 8, n is an integer from 2 to 10000, and each $R^7$ is independently a monovalent radical consisting of hydrogen and an alkyl group of 1 to 30 carbons. Thus, the ether repeat unit comprises 2 to 10 backbone carbons between each backbone oxygen. More particularly, the poly(alkylene glycol) can be a mono endcapped poly(alkylene glycol), represented by the formula (5):

$$R^8O-[C(R^7)_2(C(R^7)_2)_{a'}C(R^7)_2O]_n-H \qquad (5),$$

wherein $R^8$ is a monovalent hydrocarbon radical comprising 1 to 20 carbons.

As non-limiting examples, the polyether alcohol can be a poly(ethylene glycol) (PEG), having the structure HO—[$CH_2CH_2O$]$_n$—H, wherein the ether repeat unit $CH_2CH_2O$ (shown in the brackets) comprises two backbone carbons linked to a backbone oxygen. The polyether alcohol can also be a poly(propylene glycol) (PPG) having the structure HO—[$CH_2CH(CH_3)O$]$_n$—H, where the ether repeat unit $CH_2CH(CH_3)O$ comprises two backbone carbons linked to a backbone oxygen with a methyl side-chain. An example of mono end capped PEG is the commercially available monomethyl end capped PEG, wherein $R^8$ is a methyl group. Other examples include poly(oxetane), having the structure HO—[$CH_2CH_2CH_2O$]$_n$—H, and poly(tetrahydrofuran), having the structure HO—[$CH_2(CH_2)_2CH_2O$]$_n$—H.

The mono end capped poly(alkylene glycol) can comprise more elaborate chemical structures, represented by the general formula (6):

$$Z'-[C(R^7)_2(C(R^7)_2)_{a}C(R^7)_2O]_{n-1}-H \qquad (6),$$

wherein Z' is a monovalent radical including the backbone carbons and oxygen of the end repeat unit, and can have 2 to 100 carbons. The following non-limiting examples illustrate mono end-derivatization of poly(ethylene glycol) (PEG). As described above, one end repeat unit of PEG can be capped with a monovalent hydrocarbon group having 1 to 20 carbons, such as the monomethyl PEG (MPEG), wherein Z' is MeOCH$_2$CH$_2$O— as shown further above for MPEG in Scheme 2. The dash on the end of the MeOCH$_2$CH$_2$O— indicates the point of attachment to the polyether chain. In another example, Z' includes a thiol group, such as HSCH$_2$CH$_2$O—, or a thioether group, such as MeSCH$_2$CH$_2$O—. In another example, one end unit of PEG is an aldyhyde, wherein Z' can be OCHCH$_2$CH$_2$O—. Treating the aldehyde with a primary amine produces an imine, wherein Z' is $R^9$N=CHCH$_2$CH$_2$O—. $R^9$ is a monovalent radical selected from hydrogen, an alkyl group of 1 to 30 carbons, or an aryl group comprising 6 to 100 carbons. Continuing, the imine can be reduced to an amine, wherein Z' is $R^9$NHCH$_2$CH$_2$CH$_2$O—. In another example, one end repeat unit of PEG can be oxidized to a carboxylic acid, wherein Z' is HOOCCH$_2$O—. Using known methods the carboxylic acid can be converted to an ester, wherein Z' becomes $R^9$OOCCH$_2$O—. Alternatively, the carboxylic acid can be converted to an amide, wherein Z' becomes $R^9$NHOCCH$_2$O—. Many other derivatives are possible. In a particular embodiment, Z' is a group comprising a biologically active moiety that interacts with a specific cell type. For example, the Z' group can comprise a galactose moiety which specifically recognizes liver cells. In this instance, Z' has the structure:

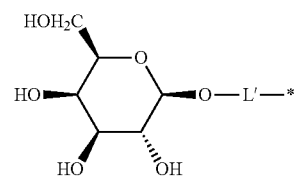

where L' is a divalent linking group comprising 2 to 50 carbons containing the end repeat unit. The starred bond on the right side of L' indicates the attachment point to the polyether chain. Z' can comprise other biologically active moieties such as mannose.

A polyether alcohol initiator for a ring opening polymerization can comprise a poly(alkylene glycol) or a mono-derivatized poly(alkylene glycol). The number average molecular weight of the polyether alcohol can be from 100 to 100,000, more specifically 100 to 10000, and even more specifically, 100 to 5000.

Cyclic Carbonyl Monomers.

The cyclic carbonyl monomers can have the general formula (7):

(7)

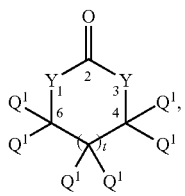

wherein t is an integer from 0 to 6, and when t is 0, carbons labeled 4 and 6 are linked together by a single bond. Each Y is a divalent radical independently selected from the group consisting of —O—, —S—,

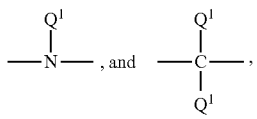

wherein the dashes "—" indicate the point of attachment in the ring. The latter two groups are expressed herein as —N($Q^1$)- and —C($Q^1$)$_2$-. Each $Q^1$ is an independent monovalent radical. Each $Q^1$ group can independently be branched or non-branched. Each $Q^1$ group can independently comprise a polymer comprising from 1 to 10000 carbons. A $Q^1$ group can have the structure

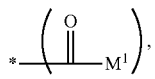

wherein the starred bond on the left side of the carbonyl indicates the point of attachment, $M^1$ is a monovalent radical, polymeric or non-polymeric. As examples, each $M^1$ can independently be selected from the group consisting of —$R^1$, —$OR^1$, —$NHR^1$, —$NR^1R^1$, and —$SR^1$ wherein the dash represents the point of attachment, and each $R^1$ is an independent polymeric or non-polymeric monovalent radical. In this example, each $R^1$ can independently be selected from the group consisting of alkyl groups comprising 1 to 100 carbons, and aryl groups comprising 6 to 100 carbons. Each $Q^1$ group can independently comprise one or more additional functional groups selected from the group consisting of ketone groups, aldehyde groups, alkene groups, alkyne groups, cycloaliphatic rings comprising 3 to 10 carbons, heterocylic rings comprising 2 to 10 carbons, ether groups, amide groups, ester groups, carboxylic acid groups, urea groups, and combinations of the foregoing additional functional groups. The heterocyclic ring can comprise oxygen, sulfur and/or nitrogen. Two or more $Q^1$ groups can together form a ring. In an embodiment, one or more of the $Q^1$ groups comprise a monovalent urea radical. In another embodiment, one or more of the $Q^1$ groups comprise a latent carboxylic acid group capable of being converted to a carboxylic acid after ring-opening polymerization. In another embodiment, one or more of the $Q^1$ groups comprise a functional group capable of reacting with a tertiary amine to form a quaternary amine In another embodiment, each $Q^1$ is independently selected from the group consisting of hydrogen, alkyl groups comprising 1 to 100 carbons, and aryl groups comprising 6 to 100 carbons. In another embodiment, at least one $Q^1$ group is a group other than hydrogen.

A more specific cyclic carbonyl monomer has the general formula (8):

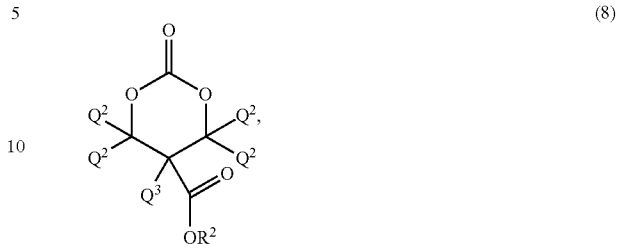

wherein each $Q^2$ and $Q^3$ is an independent monovalent radical and $R^2$ is a monovalent radical, polymeric or non-polymeric. As examples, each $Q^2$ and $Q^3$ can independently be selected from the group consisting of hydrogen, halides, alkyl groups having 1 to 100 carbons, and aryl groups having 6 to 100 carbons. When $Q^2$ and $Q^3$ are not hydrogen, $Q^2$ and $Q^3$ represent pendant moieties to the cyclic carbonyl ring that become side chains to the ROP polymer chain. The —$CO_2R^2$ group also becomes a side chain to the ROP polymer after ring opening polymerization. In an embodiment, each $Q^2$ is hydrogen and $Q^3$ is a methyl or ethyl group. In another embodiment, $R^2$ comprises a monovalent urea radical. In another embodiment, $R^2$ comprises a latent carboxylic acid group capable of being converted to a carboxylic acid after ring-opening polymerization. In another embodiment, $R^2$ comprises a functional group capable of reacting with a tertiary amine to form a quaternary amine In another embodiment, $R^2$ comprises a second polymer comprising from 1 to 10000 carbons.

Another more specific cyclic carbonyl monomer has the general formula (9):

wherein each $Q^4$ is an independent monovalent radical, and u is an integer from 1 to 8. As examples, each $Q^4$ can independently be selected from the group consisting of hydrogen, halides, alkyl groups comprising 1 to 100 carbons, aryl groups comprising 6 to 100 carbon atoms, and groups having the structure

wherein $M^1$ is a monovalent radical, polymeric or non-polymeric. As examples, $M^1$ can be selected from the group consisting of —$R^1$, —$OR^1$, —$NHR^1$, —$NR^1R^1$, and —$SR^1$ wherein the dash represents the point of attachment, and $R^1$ is a monovalent radical, polymeric or non-polymeric. As examples, each $R^1$ can independently be selected from the group consisting of alkyl groups comprising 1 to 100 carbons, and aryl groups comprising 6 to 100 carbons. When $Q^4$ is not hydrogen, $Q^4$ represents a pendant moiety to the cyclic carbonyl ring that becomes a side chain to the ROP polymer after ring opening polymerization. The lactone ring can optionally comprise a carbon-carbon double bond; that is, optionally, a

group of formula (9) can independently represent a

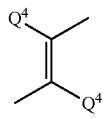

or a

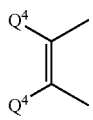

group. The lactone ring can also comprise a heteroatom not linked to the ring carbonyl or ring oxygen, such as oxygen, nitrogen, sulfur, or a combination thereof; that is, optionally a

group of formula (9) can independently represent a —O—, —S—, or —NR$^1$— group. In an embodiment, u is an integer from 1 to 6 and each Q$^4$ is hydrogen. In an embodiment, one or more of the Q$^4$ groups comprise a monovalent urea radical. In another embodiment, one or more of the Q$^4$ groups comprise a latent carboxylic acid group capable of being converted to a carboxylic acid after ring opening polymerization. In another embodiment, one or more of the Q$^4$ groups comprise a functional group capable of reacting with a tertiary amine to form a quaternary amine.

The cyclic carbonyl monomer can have the general formula (10):

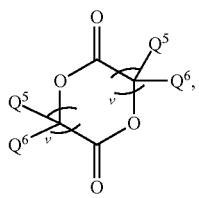

wherein each Q$^5$ is an independent monovalent radical. As examples, each Q$^5$ can independently be selected from the group consisting of hydrogen, halides, alkyl groups comprising 1 to 100 carbons, aryl groups comprising 6 to 100 carbon atoms, and groups having the structure

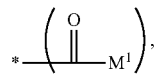

wherein M$^1$ is a monovalent radical, polymeric or non-polymeric, and each v is independently an integer from 1 to 6. As examples, M$^1$ can be selected from the group consisting of —R$^1$, —OR$^1$, —NHR$^1$, —NR$^1$R$^1$, and —SR$^1$ wherein the dash represents the point of attachment, and R$^1$ is a monovalent radical, polymeric or non-polymeric. As examples, each R$^1$ can independently be selected from the group consisting of alkyl groups comprising 1 to 100 carbons, and aryl groups comprising 6 to 100 carbons. Each Q$^6$ is an independent monovalent radical. As examples, each Q$^6$ can independently be selected from the group consisting of hydrogen, alkyl groups having 1 to 100 carbons, and aryl groups having 6 to 100 carbons. When Q$^5$ and Q$^6$ are not hydrogen, Q$^5$ and Q$^6$ represent pendant moieties to the cyclic carbonyl ring that become side chains to the ROP polymer after ring opening polymerization. In an embodiment, each v is 1, each Q$^5$ is hydrogen, and each Q$^6$ is a hydrocarbon group comprising 1 to 6 carbons. In an embodiment, one or more of the Q$^5$ and/or Q$^6$ groups comprise a monovalent urea radical. In another embodiment, one or more of the Q$^5$ and/or Q$^6$ groups comprise a latent carboxylic acid group capable of being converted to a carboxylic acid after ring-opening polymerization. In another embodiment, one or more of the Q$^5$ and/or Q$^6$ groups comprise a functional group capable of reacting with a tertiary amine to form a quaternary amine.

In an embodiment, the polymer arm comprises repeat units derived from a cyclic carbonyl monomer of the general formula (11):

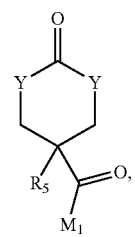

wherein each Y is independently selected from the group consisting of —O—, —NH—,

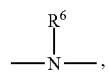

and —S—, R$^5$ and R$^6$ are independent monovalent radicals comprising 1 to 30 carbons, and M$^1$ is selected from the group consisting of —OR$^1$, —NHR$^1$, —NR$^1$R$^1$, and —SR$^1$ wherein the dash represents the point of attachment, and R$^1$ is a monovalent radical. M$^1$ can comprise a non-polymeric group or a second polymer, wherein the second polymer comprises 1 to 10000 carbons.

The cyclic carbonyl monomer can comprise a latent carboxylic acid. Non-limiting examples of latent carboxylic acids include esters that can be hydrolyzed under mild conditions (e.g., trifluoroethyl ester, pentafluorophenyl ester, or p-nitrophenyl ester, N-hydroxysuccinimimide ester, trimethylsilyl ester, tetrahydropyranyl ester). Other latent carboxylic acids include thermally labile tertiary esters (e.g., t-butyl esters). Still other latent carboxylic acids include esters capable of being reductively cleaved using hydrogen and a suitable catalyst (e.g., benzyl esters, cleavable by $H_2$/Pd—C). In an embodiment, the latent carboxylic acid group is any carboxylic ester that can be converted to a carboxylic acid by hydrogenation using a suitable catalyst. One example is the benzyl ester of MTCOBn.

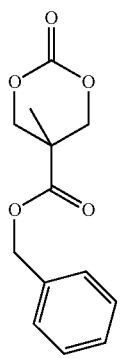

(MTCOBn)

The benzyl ester of MTCOBn can be cleaved to a carboxylic acid using $H_2$/Pd—C after the ring opening polymerization.

Another example of a latent carboxylic acid group is an acetal-protected carboxylic acid group, herein also referred to as an acetal ester group. The acetal ester group has the general formula (12):

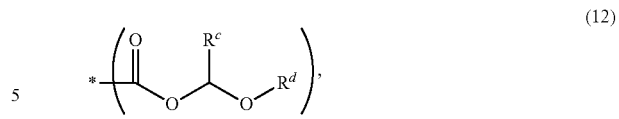

wherein the starred bond (*) represents the site of attachment to a cyclic carbonyl moiety, and $R^c$ and $R^d$ are monovalent radicals independently comprising from 1 to 20 carbons. In an embodiment, $R^c$ is methyl and $R^d$ is ethyl. An example of cyclic carbonyl compound comprising an acetal ester is MTCOEE:

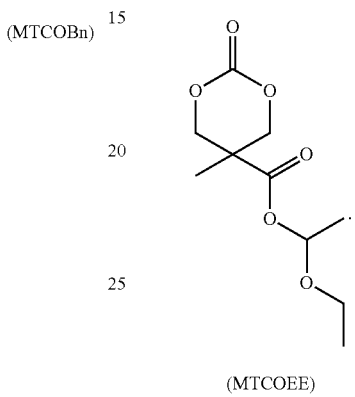

(MTCOEE)

When copolymerized into the polymer, repeat units derived from MTCOEE comprise a side chain acetal ester that is readily deprotected in the acidic endosomal environment. Once released into the cytoplasm, the resulting carboxylic acid groups of the cationic polymer can be deprotonated.

Additional cyclic carbonyl monomers of formulas (8), (9), and (10) are listed in Table 2.

TABLE 2

| | |
|---|---|
| 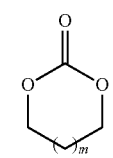<br>m = 1 Trimethylene carbonate (TMC)<br>m = 2, Tetramethylene carbonate (TEMC)<br>m = 3, Pentamethylene carbonate (PMC) | 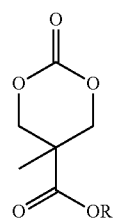<br>R = hydrogen (MTCOH)<br>R = methyl (MTCOMe)<br>R = t-butyl (MTCOtBu)<br>R = ethyl (MTCOEt) |
| 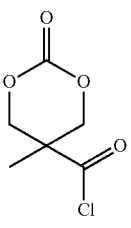<br>(MTCCl) | 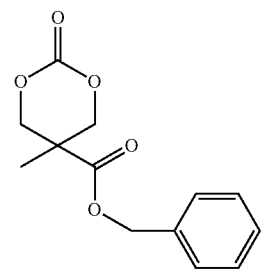 [SMILES: CC1(C(=O)OCc2ccccc2)COC(=O)OC1]<br>(MTCOBn) |

TABLE 2-continued
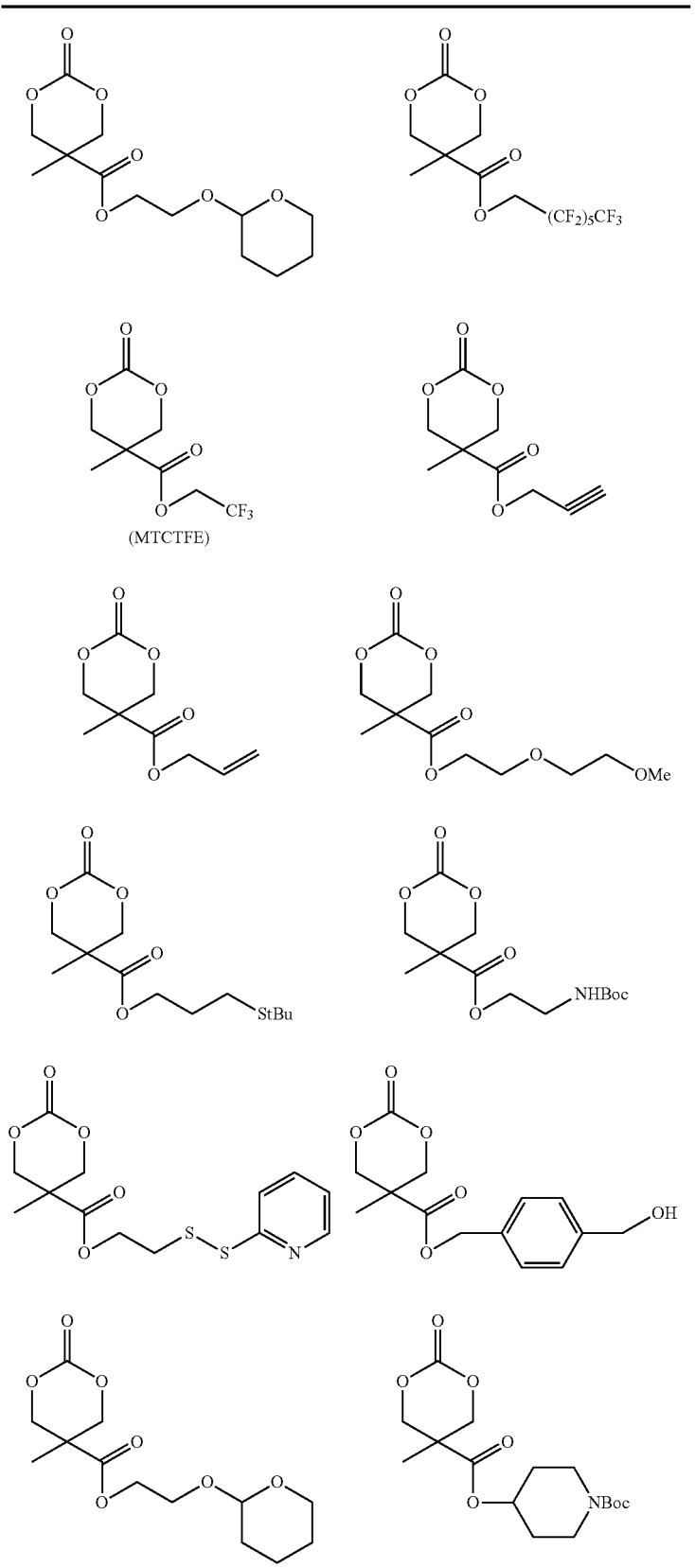

TABLE 2-continued
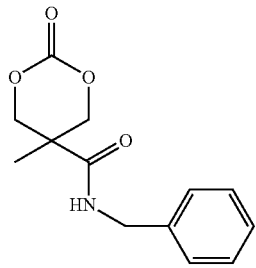 [SMILES: CC1(C(=O)NCc2ccccc2)COC(=O)OC1]
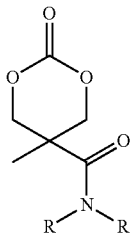
R = methyl
R = iso-propyl
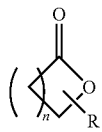
R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = CH3; n = 1: beta-Butyrolactone (b-BL)
R = CH3; n = 2: gamma-Valerolactone (g-VL)
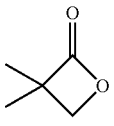
Pivalolactone
(PVL)
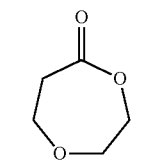
1,5-Dioxepan-2-one
(DXO)
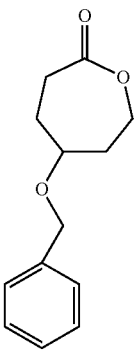 [SMILES: O=C1CCC(OCc2ccccc2)CCO1]
5-(Benzyloxy)oxepan-2-one
(BXO)
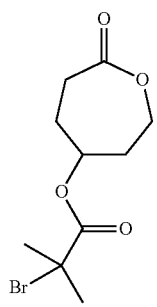
7-Oxooxepan-4-yl 2-bromo-2-methylpropanoate
(BMP-XO)
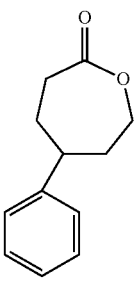 [SMILES: O=C1CCC(c2ccccc2)CCO1]
5-Phenyloxepan-2-one
(PXO)

TABLE 2-continued
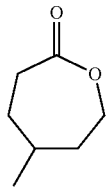
5-Methyloxepan-2-one
(MXO)
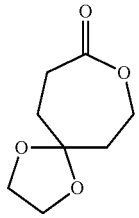 [SMILES: O=C1CCC2(CCO1)OCCO2]
1,4,8-Trioxa(4,6)spiro-9-undecane
(TOSUO)
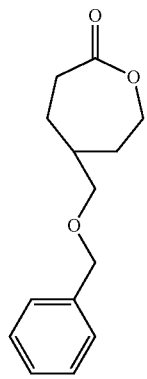 [SMILES: O=C1CCC(COCc2ccccc2)CCO1]
5-(Benzyloxymethyl)oxepan-2-one
(BOMXO)
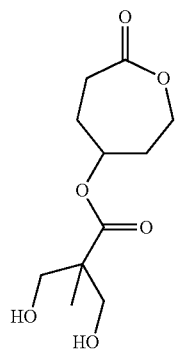 [SMILES: CC(CO)(CO)C(=O)OC1CCOC(=O)CC1]
7-Oxooxepan-4-yl 3-hydroxy-2-
(hydroxymethyl)-2-methylpropanoate
(OX-BHMP)
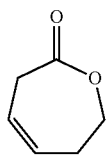
(Z)-6,7-Dihydrooxepin-2(3H)-one
(DHXO)
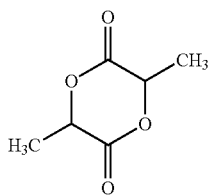
D-Lactide (DLA)
L-Lactide (LLA) or
racemic Lactide, 1:1 D:L forms (DLLA)
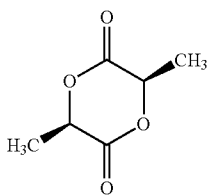
meso-Lactide (MLA)
(two opposite centers of asymmetry
R and S)
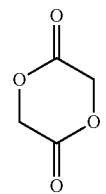
Glycolide
(GLY)

TABLE 2-continued

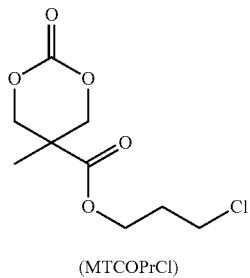
(MTCOPrCl)

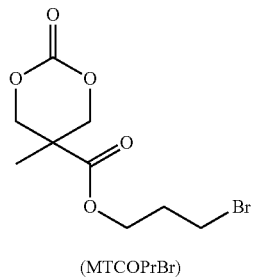
(MTCOPrBr)

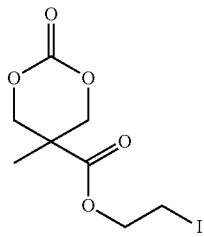
(MTCOEtI)

The cyclic carbonyl monomers can be purified by recrystallization from a solvent such as ethyl acetate or by other known methods of purification, with particular attention being paid to removing as much water as possible from the monomer. The monomer moisture content can be from 1 to 10,000 ppm, 1 to 1,000 ppm, 1 to 500 ppm, and most specifically 1 to 100 ppm, by weight of the monomer.

The cyclic carbonyl monomers can also comprise isotopically enriched forms of the cyclic carbonyl monomers. These include functional groups comprising elements selected from the group consisting of $^{13}C$, $^{14}C$, $^{15}N$, deuterium, tritium, and combinations thereof. The cyclic carbonyl monomers can also comprise a radioactive moiety suitable for targeting a specific cell type, such as a cancer cell.

The cyclic carbonyl monomers can comprise a reactive monovalent leaving group that when treated with a tertiary amine, produces a quaternary amine. Reactive monovalent leaving groups include alkyl halides (e.g., alkyl chlorides, alkyl bromides, or alkyl iodides), sulfonate esters (e.g., tosylates, or mesylates), epoxides, and oxetanes. Reaction with the tertiary amine is generally performed after the ring opening reaction when the reactive monovalent leaving group occupies a side chain position in the ROP polymer.

The tertiary amine can comprise a single nitrogen such as a trialkylamine, including but not limited to trimethylamine, triethylamine, tripropylamine, and the like. The tertiary amine can further comprise additional functional groups, in particular a carboxylic acid group, for example 3-(N,N-dimethylamino)propionic acid. In such instances, the cationic polymer will comprise first repeat units comprising a side chain moiety comprising a quaternary amine and a carboxylic acid group.

The tertiary amine can also comprise isotopically enriched versions of the tertiary amine, such as trimethyl-amine-$^{14}C$, trimethylamine-$^{15}N$, trimethylamine-$^{15}N$, trimethyl-$^{13}C_3$-amine, trimethyl-$d_9$-amine, and trimethyl-$d_9$-amine-$^{15}N$. The tertiary amine can also comprise a radioactive moiety suitable for targeting a specific cell type, such as a cancer cell.

The tertiary amine can be a bis-tertiary amine of the general formula (13):

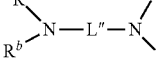

where L" is a divalent linking group comprising 2 to 30 carbons, and each monovalent $R^b$ group is independently selected from alkyl groups comprising 1 to 30 carbons or aryl groups comprising 6 to 30 carbons. Each $R^b$ group can independently be branched or non-branched. Each $R^b$ group can independently comprise additional functional groups such as a ketone group, aldehyde group, hydroxyl group, alkene group, alkyne group, cycloaliphatic ring comprising 3 to 10 carbons, heterocylic ring comprising 2 to 10 carbons, ether group, amide group, ester group, and combinations of the foregoing additional functional groups. The heterocyclic ring can comprise oxygen, sulfur and/or nitrogen. Two or more $R^b$ groups can also together form a ring. Representative L" groups include —$(CH_2)_{z'}$— where z' is an integer from 2 to 30, —$(CH_2CH_2O)_{z''}CH_2CH_2$— where z" is an integer from 1 to 10, —$CH_2CH_2SCH_2CH_2$—, —$CH_2CH_2SSCH_2CH_2$—, —$CH_2CH_2SOCH_2CH_2$—, and —$CH_2CH_2SO_2CH_2CH_2$—. L" can further comprise a monovalent or divalent cycloaliphatic ring comprising 3 to 20 carbons, a monovalent or divalent aromatic ring comprising 6 to 20 carbons, a ketone group, aldehyde group, hydroxyl group, alkene group, alkyne group, a heterocylic ring comprising 2 to 10 carbons, ether group, amide group, ester group, and combinations of the foregoing functional groups. The heterocyclic ring can comprise oxygen, sulfur and/or nitrogen. The bis-tertiary amine can also comprise isotopically enriched forms of the bis-tertiary amine, such as deuterium, carbon-13, and/or nitrogen-15 enriched forms thereof.

More specific bis-tertiary amines include N,N,N',N'-tetramethyl-1,2-ethanediamine (TMEDA), N,N,N',N'-tetramethyl-1,3-propanediamine (TMPDA), N,N,N',N'-tetramethyl-1,4-butanediamine (TMBDA), N,N,N',N'-tetraethyl-1,2-ethanediamine (TEEDA), N,N,N',N'-tetraethyl-1, 3propanediamine (TEPDA), 1,4-bis(dimethylamino) cyclohexane, 1,4-bis(dimethylaminobenzene), N,N,N',N'-tetraethyl-1,4-butanediamine (TEBDA), 4-dimethylaminopyridine (DMAP), 4,4-dipyridyl-1,4-diaz-abicyclo[2.2.2]octane (DABCO), 4-pyrrolidinopyridine, 1-methylbenzimidazole, and combinations thereof. In an embodiment, the bis-tertiary amine is TMEDA.

The above-described cyclic carbonyl monomers undergo ring-opening polymerization to form a ROP polymers in atactic, syndiotactic or isotactic forms. The particular tacticity depends on the cyclic monomer(s), isomeric purity, and the reaction conditions.

The reaction mixture for the ring opening polymerization comprises one or more cyclic carbonyl monomers; a catalyst; an optional accelerator; an optional solvent, and an initiator. The ring opening polymerization is generally conducted in a reactor under inert atmosphere such as nitrogen or argon. The polymerization can be performed by solution polymerization in an anhydrous non-protic solvent such as benzene, toluene, xylene, cyclohexane, n-hexane, dioxane, chloroform and dichloroethane, or by bulk polymerization. The reaction temperature can be from about ambient temperature to 250° C. Generally, the reaction mixture is heated at atmospheric pressure for 0.5 to 72 hours to effect polymerization, forming a second mixture.

Less preferred catalysts for ring opening polymerizations include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; heteropolyacids such as phosphotungstic acid, phosphomolybdic acid, silicotungstic acid and alkali metal salt thereof; zirconium compounds such as zirconium acid chloride, zirconium octanoate, zirconium stearate and zirconium nitrate.

Metal from a polymerization catalyst can be entrapped by the crosslinked polymer core of the star polymer. The trapped metal can be cytotoxic and can interfere with the binding, release and/or the function of a cargo material and/or inorganic shell. Therefore, star polymers comprising a minimum of each restricted metal described further above is highly desirable.

Preferred catalysts for the ring opening polymerization are organocatalysts. An organocatalyst overcomes the problem of entrapped metal, in addition to providing a platform for synthesizing ring opened polymers of controlled, predictable molecular weights and narrow polydispersities. Examples of organocatalysts for ring opening polymerization of cyclic esters, cyclic carbonates and siloxanes are 4-dimethylaminopyridine, phosphines, N-heterocyclic carbenes (NHC), bifunctional aminothioureas, phosphazenes, amidines, and guanidines. In an embodiment the catalyst is N-(3,5-trifluoromethyl)phenyl-N'-cyclohexyl-thiourea (TU):

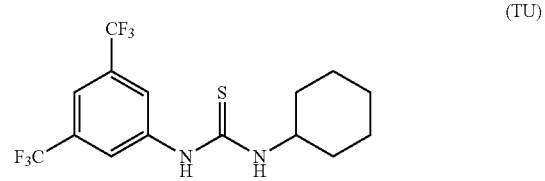 [SMILES: FC(F)(F)c1cc(NC(=S)NC2CCCCC2)cc(C(F)(F)F)c1]

Other organocatalysts comprise at least one 1,1,1,3,3,3-hexafluoropropan-2-ol-2-yl (HFP) group. Singly-donating hydrogen bond catalysts have the formula (14):

$R^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalklyl group, aryl group, substituted aryl group, or a combination thereof. Exemplary singly-donating hydrogen bonding catalysts are listed in Table 3.

TABLE 3

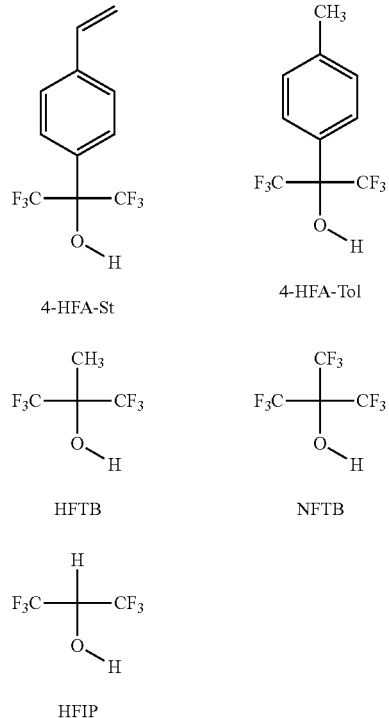

Doubly-donating hydrogen bonding catalysts have two HFP groups, represented by the general formula (15):

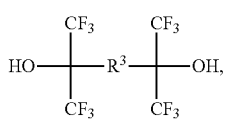

(15)

wherein R³ is a divalent radical bridging group containing from 1 to 20 carbons, such as an alkylene group, a substituted alkylene group, a cycloalkylene group, a substituted cycloalkylene group, a heterocycloalkylene group, substituted heterocycloalkylene group, an arylene group, a substituted arylene group, or a combination thereof. Representative double hydrogen bonding catalysts of formula (15) include those listed in Table 4. In a specific embodiment, R² is an arylene or substituted arylene group, and the HFP groups occupy positions meta to each other on the aromatic ring.

TABLE 4

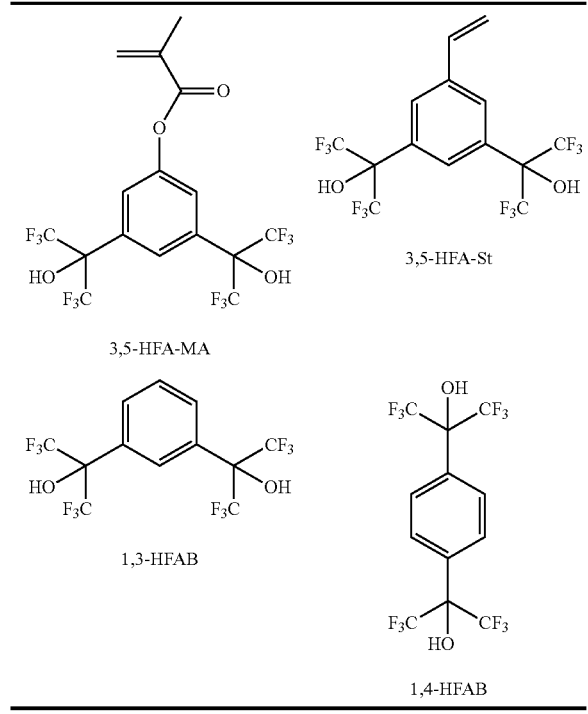

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

Also contemplated are organocatalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Alternatively, pre-formed polymers and other solid support surfaces can be modified by chemically bonding an HFP-containing group to the polymer or support via a linking group. Examples of linking groups include $C_1$-$C_{12}$ alkyl, $C_1$-$C_{12}$ heteroalkyl, an ether group, a thioether group, an amino group, an ester group, an amide group, or a combination thereof. Also contemplated are catalysts comprising charged HFP-containing groups bound by ionic association to oppositely charged sites on a polymer or a support surface.

The organocatalyst can also be a nitrogen base, as indicated above. Exemplary nitrogen base catalysts include triallylamine, triethylamine, tri-n-octylamine and benzyldimethylamine. Other nitrogen base catalysts, listed in Table 5, include pyridine (Py), N,N-dimethylaminocyclohexane (Me₂NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (–)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl(imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof.

TABLE 5

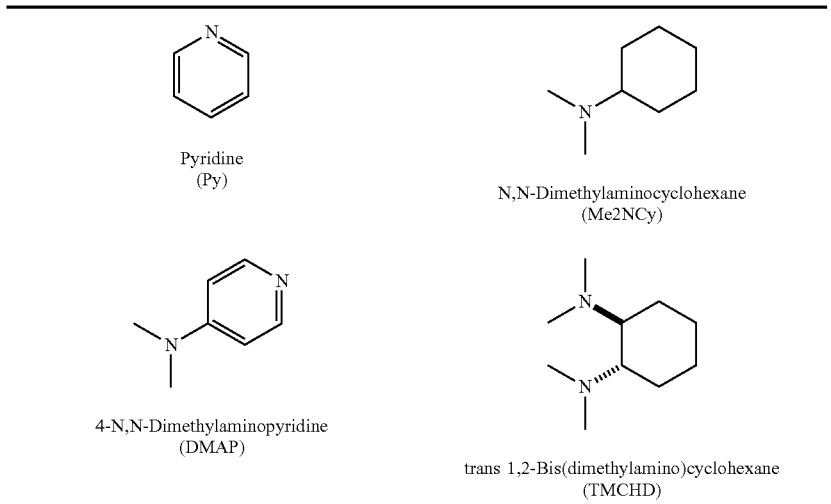

TABLE 5-continued
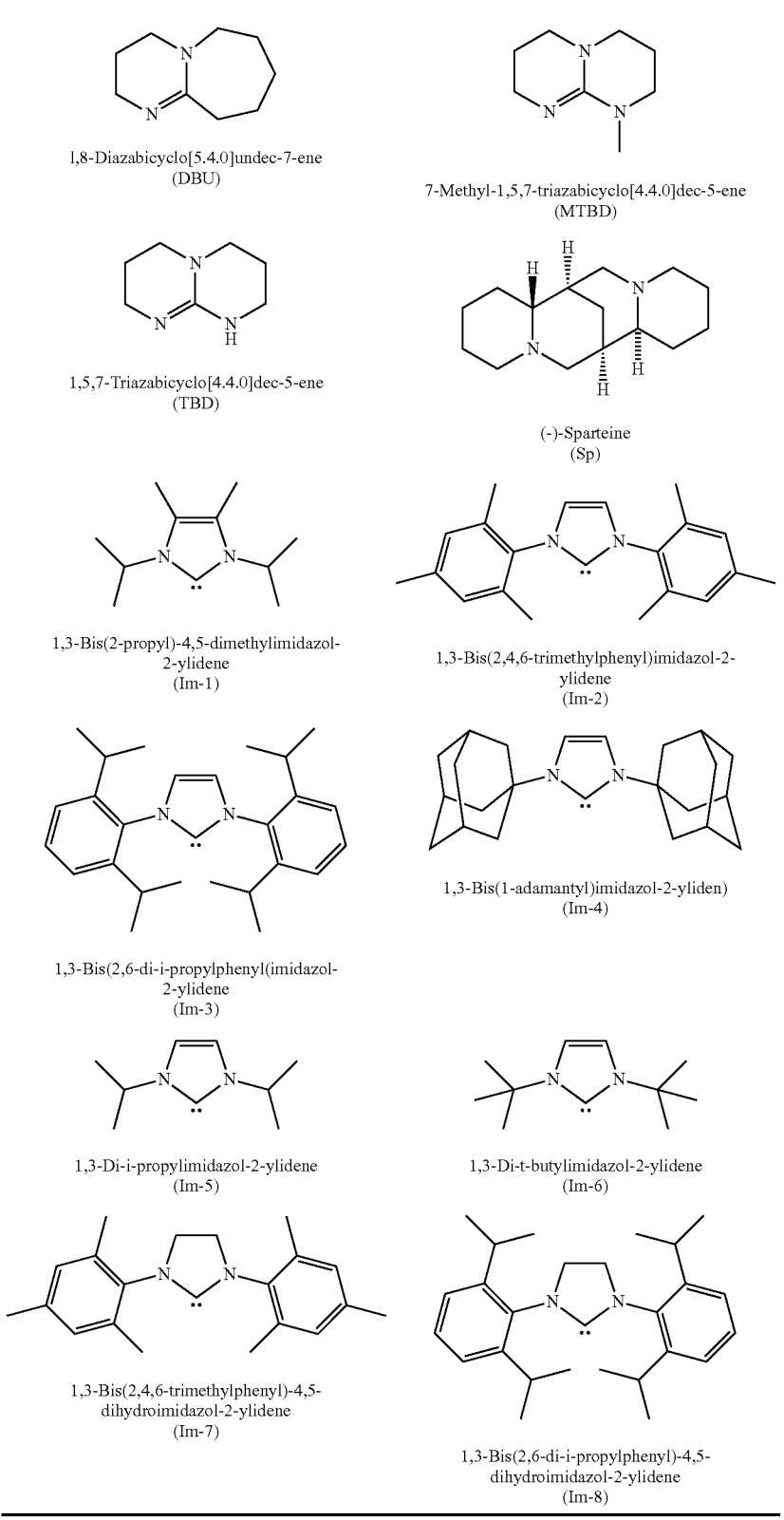
The above-described nitrogen bases can be used alone as a catalyst when producing linear polymers by ring opening polymerization, such as the polymer arm precursor. Alternatively, the nitrogen bases can serve as an optional accelerator when used in combination with a primary catalyst, such as TU, in a ring opening polymerization. When employed as an accelerator, each nitrogen is potentially capable of participating as a Lewis base. In general, stronger nitrogen base accelerators improve the polymerization rate.

Exceptions to the above have been found when attempting to generate the polymer core by ring opening polymerization using base catalysis alone. In these instances, nitrogen bases comprising 1 or 2 nitrogens were not effective in forming unimolecular star polymers. The 1-nitrogen and 2-nitrogen base catalysts produced star polymers having high polydispersities (greater than 1.35), or products that were amorphous. Preferred nitrogen bases for the formation of the polymer core by ring opening polymerization of a bis-cyclic carbonyl monomer have three or more nitrogens. Unimolecular nano-sized amphiphilic star polymers having a polydispersity of 1.35 or less were successfully produced using this type of catalyst. One such base catalyst is 1,5,7-triazabicyclo[4.4.0]dec-5-ene (TBD). In some instances the star polymer can be formed using TBD as the sole catalyst. The star polymer can have a polydispersity index of 1.26, a hydrodynamic radius of 10.9 nm, and contains less than 100 ppm of any restricted metal.

The ROP reaction mixture comprises at least one catalyst and, when appropriate, several catalysts together. The ROP catalyst is added in a proportion of 1/20 to 1/40,000 moles relative to the cyclic carbonyl monomers, and preferably of 1/100 to 1/20,000 moles.

The ROP reaction mixture also comprises an initiator. Initiators generally include nucleophiles such as alcohols, amines and thiols. The initiator can be monofunctional, difunctional, or multifunctional. The initiator can be polymeric or non-polymeric. For example, the initiator can be a polymeric alcohol, polymeric amine, or polymeric thiol.

More particularly, the initiator for the ring opening reaction is an alcohol. The alcohol initiator can be any suitable alcohol, including mono-alcohol, diol, triol, or other polyol, with the proviso that the choice of alcohol does not adversely affect the polymerization yield, polymer molecular weight, complexation with a biologically active material, and/or the desirable mechanical and physical properties of the star polymer. The alcohol can be multi-functional comprising, in addition to one or more hydroxyl groups, a halide, an ether group, an ester group, an amide group, or other functional group. Exemplary alcohols includes methanol, ethanol, propanol, butanol, pentanol, amyl alcohol, capryl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, nonadecyl alcohol and other aliphatic saturated alcohols, cyclopentanol, cyclohexanol, cycloheptanol, cyclooctanol and other aliphatic cyclic alcohols; phenol, substituted phenols, benzyl alcohol, substituted benzyl alcohol, benzenedimethanol, trimethylolpropane, a saccharide, poly(ethylene glycol), propylene glycol, alcohol functionalized block copolymers derived from oligomeric alcohols, alcohol functionalized branched polymers derived from branched alcohols, or a combination thereof. Monomeric diol initiators include ethylene glycols, propylene glycols, hydroquinones, and resorcinols. An example of a diol initiator is BnMPA, derived from 2,2-dimethylol propionic acid.

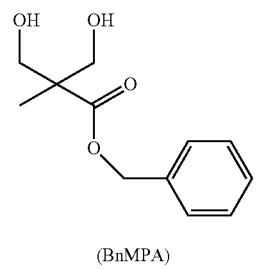 [SMILES: CC(CO)(CO)C(=O)OCc1ccccc1]

(BnMPA)

BnMPA is a precursor used in the preparation of cyclic carbonate monomers.

The ring-opening polymerization can be performed with or without the use of a solvent, more particularly with a solvent. Optional solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. When a solvent is present, a suitable cyclic carbonyl monomer concentration is about 0.1 to 5 moles per liter, and more particularly about 0.2 to 4 moles per liter.

The ring-opening polymerization can be performed at a temperature that is about ambient temperature or higher, more specifically a temperature from 15° C. to 200° C., and more particularly 20° C. to 200° C. When the reaction is conducted in bulk, the polymerization is performed at a temperature of 50° C. or higher, and more particularly 100° C. to 200° C. Reaction times vary with solvent, temperature, agitation rate, pressure, and equipment, but in general the polymerizations are complete within 1 to 100 hours.

Whether performed in solution or in bulk, the ring opening polymerizations are conducted in an inert (i.e., dry) atmosphere and at a pressure of from 100 to 500 MPa (1 to 5 atm), more typically at a pressure of 100 to 200 MPa (1 to 2 atm). At the completion of the reaction, the solvent can be removed using reduced pressure.

The nitrogen base accelerator, when used, is present in an amount of 0.1 to 5.0 mol %, 0.1 to 2.5 mol %, 0.1 to 1.0 mol %, or 0.2 to 0.5 mol %, based on total moles of cyclic carbonyl monomer.

The amount of initiator for the ring opening polymerization is calculated based on the equivalent molecular weight per nucleophilic initiating group in the initiator (e.g., alcohol groups). The initiating groups are preferably present in an amount of 0.001 to 10.0 mol %, 0.1 to 2.5 mol %, 0.1 to 1.0 mol %, and 0.2 to 0.5 mol %, based on total moles of cyclic carbonyl monomer. For example, if the molecular weight of the initiator is 100 g/mole and the initiator has 2 hydroxyl groups, the equivalent molecular weight per hydroxyl group is 50 g/mole. If the polymerization calls for 5 mol % hydroxyl groups per mole of monomer, the amount of initiator is 0.05×50=2.5g per mole of monomer.

In a specific embodiment, the catalyst is present in an amount of about 0.2 to 20 mol %, and the hydroxyl groups of the initiator are present in an amount of 0.1 to 5.0 mol % based on the equivalent molecular weight per nucleophilic group in the initiator.

As stated above, the ring opening polymerization forms a polymer chain comprising a living polymer segment. In an embodiment, one backbone repeating unit of the ROP polymer chain is an ester repeating unit. The ROP polymer backbone can, for example, also comprise a polyester homopolymer, a random polyester copolymer, a polycarbonate homopolymer, a random polycarbonate copolymer, or a random polyestercarbonate copolymer. The ROP polymer chain can comprise a terminal hydroxyl group, terminal thiol group, or terminal amine group, each of which can initiate further ROP chain growth, if desired.

The ROP polymer can comprise hydrophilic repeat units, hydrophobic repeat units, and combinations thereof, thereby imparting amphiphilic properties to the star polymer. The ROP polymer chains can have a number average molecular weight $M_n$ as determined by size exclusion chromatography of at least 2500 g/mol, more specifically 4000 g/mol to 150000 g/mol, and even more specifically 10000 g/mol to 50000 g/mol. In an embodiment, the ROP polymer chain has a number average molecular weight $M_n$ of 10000 to 20000 g/mole. The ROP polymer chains also have a narrow polydispersity index (PDI), generally less than or equal to 1.35, more particularly from 1.01 to 1.35, even more particularly 1.1 to 1.30, and still more particularly 1.1 to 1.25.

As stated above, the ROP polymer can comprise a pendant latent carboxylic acid group, such as a benzyl ester. In this instance, the latent carboxylic acid group can be deprotected using $H_2$/Pd—C to form a pendant carboxylic acid group. If the protected carboxylic acid is in the form of a thermally labile carboxylic ester, such as a t-butyl ester, deprotection can be effected by heating the ROP polymer. If the protected carboxylic acid is hydrolytically unstable, such as a trifluoroethyl ester, the ROP polymer can be deprotected with mild aqueous acid or base to form a pendant carboxylic acid group. In a particular embodiment, the protected carboxylic acid is a benzyl ester.

The star polymers can comprise repeat units comprising a positive charge, a negative charge, or a mixture thereof.

In aqueous solution the star polymers disperse to form nanoparticles having an average particle size of from about 2 nm to about 500 nm, about 10 nm to about 250 nm, and more particularly about 50 nm to about 200 nm, about 50 nm to about 150 nm, about 50 nm to about 120 nm, and even more particularly from about 50 nm to about 100 nm, as measured by dynamic light scattering. For the foregoing particle sizes, the aqueous solution can have a pH of from 5.0 to 8.0. This pH range can be increased for non-biodegradable compositions, such as those having a polymer core prepared from divinylbenzene.

Star Polymer Occlusion Complexes.

A star polymer occlusion complex comprises a star polymer and a suitable cargo material occluded therein. In an embodiment, the cargo material is selected from the group consisting of drugs, genes, dyes, image contrast enhancing materials, and combinations thereof. The cargo material can comprise a metal, including one or more of the above-described restricted metals. The cargo material can also comprise a radioactive metal. In aqueous solution at a pH of from 5.0 to 8.0, the star polymer occlusion complexes have an average particle size of from 2 nm to 500 nm, 2 nm to 250 nm, 2 nm to 150 nm, 2 nm to 120 nm, and more particularly 10 nm to 120 nm, 20 nm to 120 nm, 30 nm to 120 nm, and even more particularly from 50 nm to 120 nm, as measured by dynamic light scattering. The star polymer occlusion complexes can comprise, for example 0.1 to 90 wt. %, more particularly 5 to 50 wt. %, and even more particularly 15 to 50 wt. % of a biologically active material based on total dry weight of the star polymer occlusion complexes. In an embodiment, the biologically active cargo material is a drug. In another embodiment, the biologically active material is a contrast enhancing agent.

The star polymer occlusion complexes can comprise both small molecular weight biologically active materials in the size range from 100 daltons to about 1,000 daltons as well as larger macromolecular materials, such as peptide and protein drugs in the size range from about 1,000 daltons (Da) to about 100,000 daltons, and beyond.

Contrast enhancing agents that have been considered for nuclear magnetic resonance imaging include soluble salts of paramagnetic metal ions, paramagnetic chelates and metallic complexes, and nitroxide stable free radicals. Paramagnetic metals ions include: from the transition metals series: titanium ($Ti^{3+}$), iron ($Fe^{3+}$), vanadium ($V^{4+}$), cobalt ($Co^{3+}$), chromium ($Cr^{3+}$), nickel ($Ni^{2+}$), manganese ($Mn^{2+}$), and copper ($Cu^{2+}$); from the Lanthanide series: praseodynium ($Pr^{3+}$), gadolinium ($Gd^{3+}$), europium ($Eu^{3+}$), and dysprosium ($Dy^{3+}$); from the Actinide series: protactinium ($Pa^{4+}$); and from nitroxide stable free radicals: pyrrolidine derivatives, and piperidine derivatives. Of these, the most favored contrast enhancing agents include complexes of ferric, chromium, and gadolinium ions, and stable nitroxide free radicals. Exemplary contrast enhancing agents for x-ray imaging include barium salts and halogenated materials, more particularly brominated and/or iodinated materials.

Organic contrast enhancing agents include porphyrinoids, which include but are not limited to porphyrins, corrins, chlorins, bacteriochlorophylls, phthalocyanines, tetraazaphyrins, texaphyrins, saphyrins, and the like. A nonlimiting example of a porphyrinoid compound is 5,10,15,20-(3,5-ditertbutylphenyl)porphyrin, where the ligand M can be a metal or two hydrogens (M=2H) (DTBP):

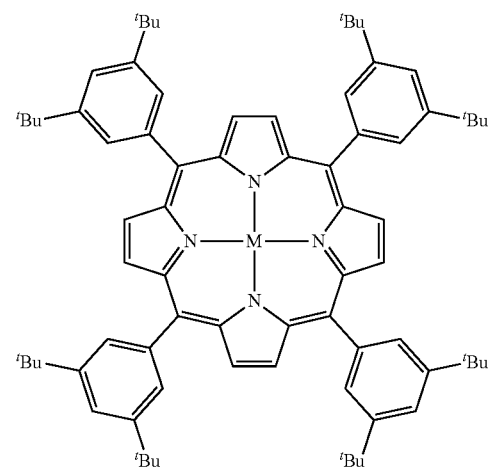

-continued

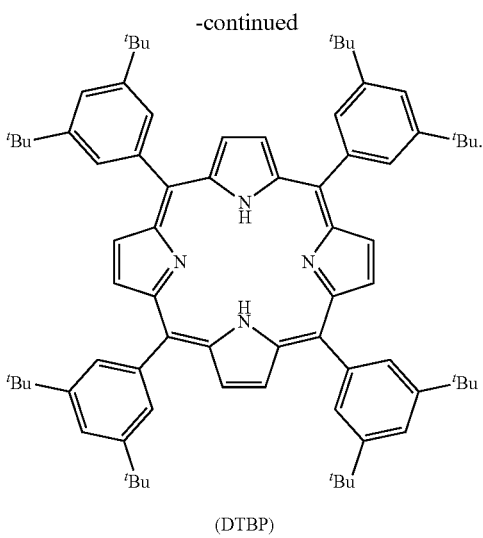

(DTBP)

Another non-limiting example of a porphyrinoid compound is tert-butyl phthalocyanine, wherein the ligand M can be a metal or two hydrogens (M=2H) (TBP):

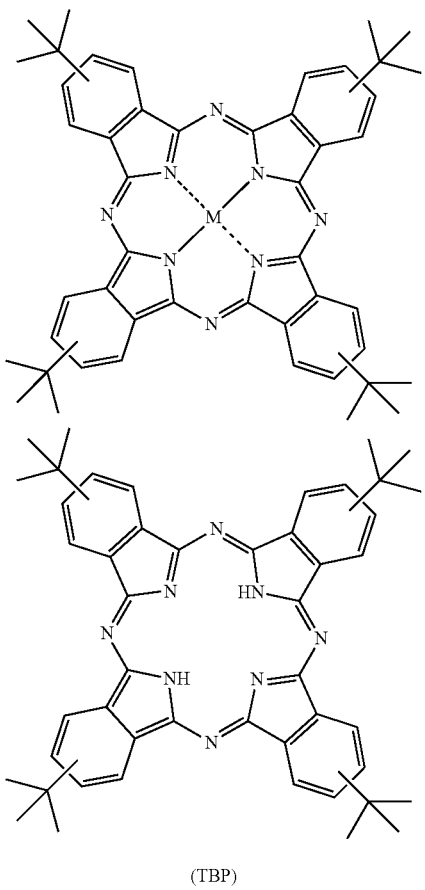

(TBP)

The contrast enhancing material can also comprise a combination of a porphyrinoid compounds. The porphyrinoid compound can further comprise a metal ligand that is a restricted metal.

The porphyrinoid compound can be in a non-aggregated state in the star polymer occlusion complex, detectable by the fluorescence of an aqueous mixture of the star polymer occlusion complex. In an embodiment, 10% to 100% by weight of the porphyrinoid compound in the star polymer occlusion complex is in a non-aggregated state. In another embodiment, 50% to 100% by weight of the porphyrinoid compound in the star polymer occlusion complex is in a non-aggregated state.

Exemplary protein drugs include peptide hormones such as insulin, glucagon, parathyroid hormone, calcitonin, vasopression, renin, prolactin, growth hormone; the gonadotropins including chorionic gonadotropin, follicle stimulating hormone, thyroid stimulating hormone and leutenizing hormone; physiologically active enzymes such as transferases, hydrolases, lyases, isomerases, phosphatases, glycosidases, superoxide dismutase, factor VIII, plasminogen activators; and other therapeutic agents including protein factors such as epidermal growth factor, insulin-like growth factor, tumour necrosis factor, transforming growth factors, fibroblast growth factors, patelet-derived growth factors, erythropoietin, colony stimulating factors, bone morphogenetic proteins, interleukins and interferons. Exemplary non-protein macromolecules include polysaccharides, nucleic acid polymers, and therapeutic secondary metabolites including plant products such as vinblastine, vincristine, taxol and the like.

Other exemplary drugs include Aspirin, Diflunisal, Diclofenac, Aceclofenac, Acemetacin, Etodolac, Indometacin, Sulindac, Tolmetin, Ibuprofen, Carprofen, Fenbufen, Fenoprofen, Flurbiprofen, Ketoprofen, Ketorolac, Loxoprofen, Naproxen, Oxaprozin, Tiaprofenic acid, Suprofen, Mefenamic acid, Meclofenamic acid, Lumiracoxib, Oxyphenbutazone, Piroxicam, Lornoxicam, Meloxicam, and Tenoxicam. Steroidal Anti-Inflammatory Drugs include Hydrocortisone, Prednisone, Prednisolone, Methylprednisolone, Dexamethasone, Betamethasone, Triamcinolone, Beclometasone, Fludrocortisone acetate, and Aldosterone. Chemotherapeutic drugs include Doxorubicin and DNA alkylating Agents such as Melphalan, Chlorambucil, Dacarbazine, Temozolomide, and Streptozotocin. Antimetabolite drugs include Methotrexate, Pemetrexed, Raltitrexed, Tioguanine, Fludarabine, Pentostatin, Cladribine, Floxuridine, and Gemcitabine. Alkaloid drugs include Vincristine, Vinblastine, Vinorelbine, Vindesine, and Topoisomerase. Inhibitors include Etoposide, Teniposide, Irinotecan, and Topotecan. Taxanes include Paclitaxel and Docetaxel. Anticoagulants include Warfarin, Acenocoumarol, Phenprocoumon, Argatroban, and Ximelagatran.

Still other exemplary commercially available drugs include 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone Acetate, Dexamethasone Sodium Phosphate Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan Idamycin®, Idarubicin, Ifex®, IFN-alpha Ifosfamide, IL-11 IL-2 Imatinib mesylate, Imidazole Carboxamide Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, K Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Oraped®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a) Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa.

A method of preparing a star polymer occlusion complex comprises i) forming a mixture of an amphiphilic star polymer and a cargo material in a first solvent; and ii) injecting the mixture into a second solvent, the second solvent being a non-solvent for the cargo material, thereby forming a star polymer occlusion complex; wherein the star polymer comprises a crosslinked polymer core and 6 or more independent polymer arms covalently linked to the core, the 6 or more polymer arms each comprise a hydrophobic chain segment and a hydrophilic chain segment. In an embodiment, the star polymer comprises no more than 100 ppm of any single restricted metal.

Nanoshells.

The nanoshells preferably have an average particle size of about 15 nm to about 300 nm, about 20 nm to about 300 nm, or more particularly about 20 nm to about 100 nm, as measured by electon microscopy (SEM and TEM) and/or light scattering measurments.

The nanoshells preferably have a polydispersity index of 2 to 1, more particularly 1.3 to 1 as measured by electon microscopy (SEM and TEM) and/or light scattering measurments.

Figure 2:
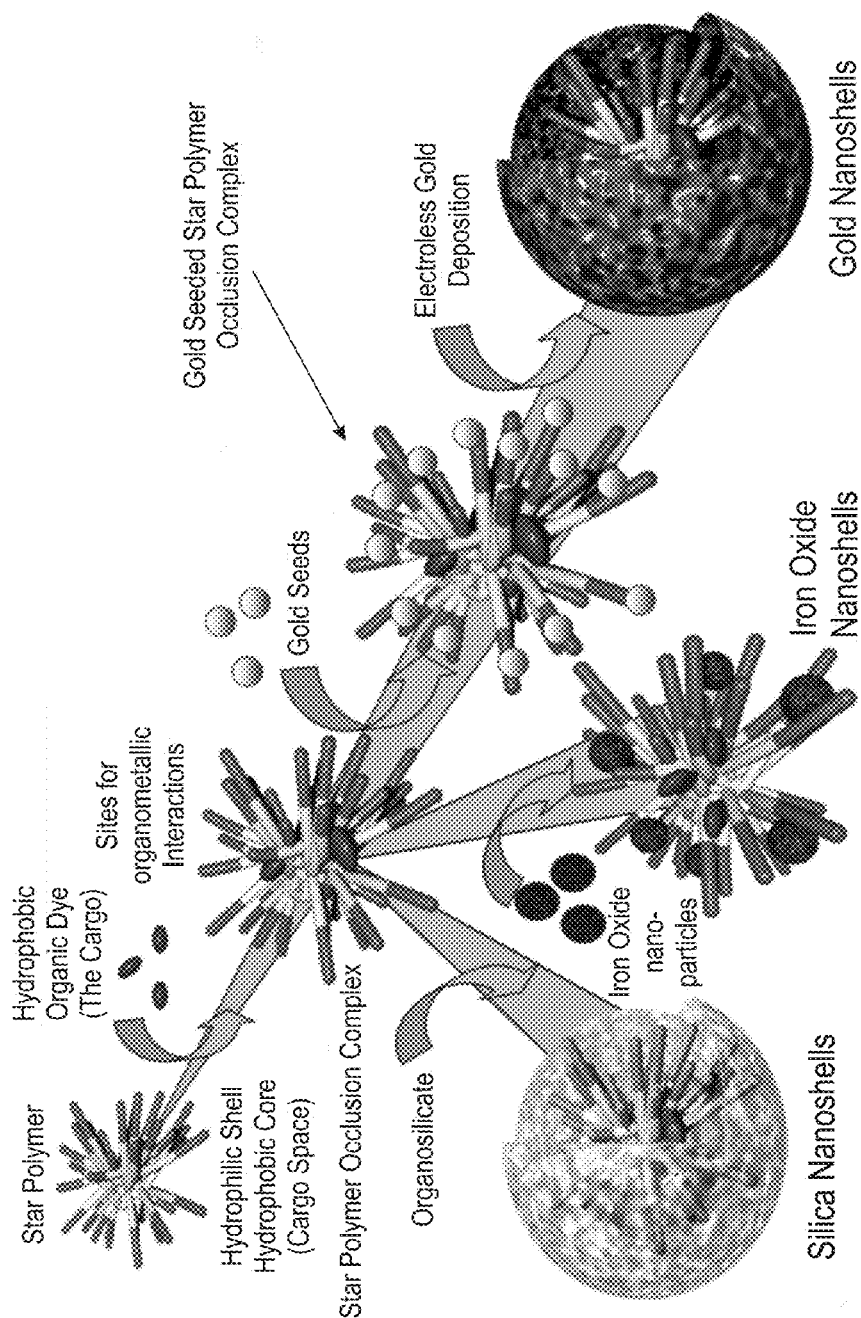
FIG. 2 is a schematic reaction diagram for the preparation of silica nanoshells, iron oxide nanoshells, and gold nanoshells from a common star polymer occlusion complex.

A nanoshell can be prepared by disposing a shell-forming material on a unimolecular star polymer occlusion complex. Alternatively, a nanoshell can be prepared by disposing a shell material on an aggregate of two or more macromolecules of star polymer occlusion complex. FIG. 2 schematically shows exemplary reaction pathways for forming silica nanoshells, iron oxide nanoshells, or gold nanoshells using a common unimolecular star polymer occlusion complexes comprising a porphyrin dye (e.g., DTBP) cargo material. In a first reaction pathway, a silica nanoshell is formed by treating the star polymer occlusion complex with an organosilicate. The silica-containing shell can be contiguous (shown) or non-contiguous (not shown). In a second reaction, an iron oxide nanoshell is formed by depositing preformed iron oxide nanoparticles on the star polymer occlusion complex. The iron oxide nanoparticles remain discrete particles in association with the peripheral hydrophilic chain segments of the star polymer arms. Thus, in this example, the iron oxide shell is non-contiguous. In a third reaction pathway of FIG. 2, a gold nanoshell is formed by i) treating the star polymer occlusion complex with pre-formed gold seeds, thereby forming a seeded occlusion complex, and ii) subjecting the seeded occlusion complex to a growth step employing electroless gold deposition, thereby forming a shell that includes gold. The gold-containing shell can be non-contiguous (not shown) depending on the conditions of the growth step.

The shell contacts at least one peripheral hydrophilic chain segment of the star polymer occlusion complex. The thickness of the shell can be adjusted by changing three parameters: reaction time, size of star polymer occlusion complex, and concentration of the shell-forming inorganic material. The shell can encompass one or more macromolecules of star polymer occlusion complex. The one or more macromolecules of star polymer occlusion complex can be in an aggregated or non-aggregated state.

The nanoshells can be further modified to introduce reactive or passive surface functionality using one or more organic tagging agents such as, for example, reactive dyes and/or reactive polymers comprising poly(alkylene oxide) chain segments (e.g., a poly(ethylene oxide) having one reactive end group). The organic tagging agent can react with the shell material to form an organic surface group covalently linked to the shell surface. The organic surface group can comprise a chemical moiety selected from the group consisting of dye moieties, polymers comprising poly(alkylene oxide) chain fragments, and combinations thereof derived from the tagging agent. As another example, the nanoshell surface can be modified by incorporating organic surface groups capable of targeting specific cell types. In this manner, multi-functional nanoshells can be formed. That is, a cargo material can perform a first function, and one or more covalently bound organic surface groups can perform one or more other functions. The shell material can perform an additional function.

A discussion of more specific nanoshells follows.

Silica Nanoshells.

Unless otherwise stated, the term "silica nanoshell" herein refers to a nanoshell comprising a shell comprising a tetravalent silicon material. The tetravalent silicon can be in the form of a silicon oxide (e.g., silica) and/or another tetravalent silicon material. Two highly reproducible methods are disclosed for forming silica nanoshells, which are illustrated in the reaction schemes of FIGS. 10A and 10B.

Figure 10A:
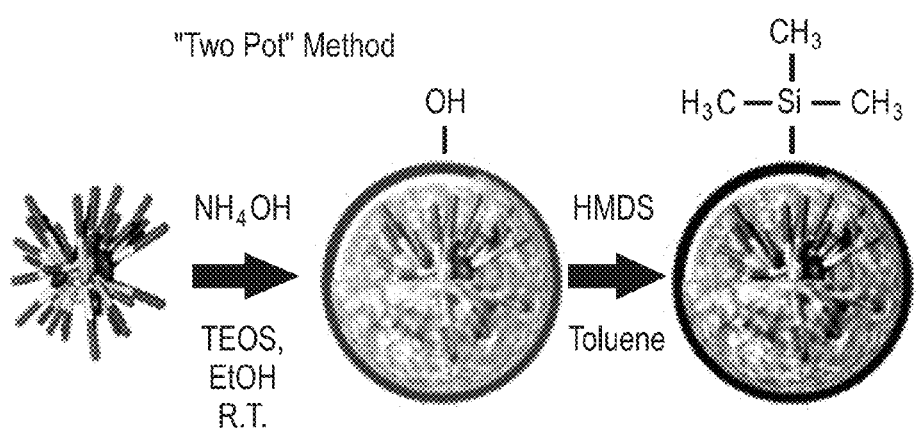
FIG. 10A is a schematic reaction diagram using three-dimensional drawing representations of the "Two-Pot" method of forming silica nanoshells.

In a first method, referred to as a "two pot" method exemplified in FIG. 10A, a star polymer occlusion complex is treated with a first silicon agent in a first solvent, and the resulting precursor nanoshell is transferred to a second solvent before adding a second silicon agent to form the silicon nanoshell. The method comprises i) treating the star polymer occlusion complex with a first silicon agent in a first solvent, thereby forming a precursor nanoshell and ii) treating the precursor nanoshell in a second solvent with a second silicon agent, thereby forming the nanoshell.

In a second method, referred to as a "one pot" method (FIG. 10B), a star polymer occlusion complex is treated sequentially with a first silicon agent and a second silicon agent using a common solvent and one reaction vessel. The method comprises i) treating a star polymer occlusion complex with a first silicon agent in a solvent, thereby forming a precursor nanoshell and ii) treating the precursor nanoshell with a second silicon agent in the solvent, thereby forming a silicon nanoshell.

Exemplary first silicon agents include orthosilicates of the formula $H_nSi(OR)_{4-n}$ wherein n is an integer of 0 to 2, and R is a monovalent radical selected from alkyl, alkenyl, alkynyl, aryl, alkyl-substituted aryl, alkenyl-substituted aryl, alkynyl-substituted aryl, aryl-substituted alkyl, alkenyl-substituted alkyl, or alkynyl-substituted alkyl, or combinations thereof. More specific examples of first silicon agents include tetramethyl orthosilicate (TMOS), tetraethyl orthosilicate (TEOS), tetrapropyl orthosilicate, tetraisopropyl orthosilicate, tetraallyl orthosilicate, tetrakis(2-hydroxyethyl), tetrabutyl orthosilicate, tetraamyl orthosilicate, tetrahexyl orthosilicate, tetraoctyl orthosilicate, tetraphenyl orthosilicate, tetratolyl orthosilicate, tetrakis(2-ethyl-1-butyl)orthosilicate, tetrakis(2-methoxyethyl)orthosilicate, and tetrakis(dimethylsilyl)orthosilicate.

Exemplary second silicon agents include compounds of the formula $HN(SiR_3)_2$ wherein R is a monovalent radical selected from alkyl, alkenyl, alkynyl, aryl, alkyl-substituted aryl, alkenyl-substituted aryl, alkynyl-substituted aryl, aryl-substituted alkyl, alkenyl-substituted alkyl, alkynyl-substituted alkyl, or combinations thereof. Specific examples include hexamethyldisilazane (HMDS) and hexaethyldisilazane. Other second silicon agents include functionalized organosilanes of the formula $R_2Si(OR)_2$, wherein each R is a monovalent radical independently selected from alkyl, alkenyl, alkynyl, aryl, alkyl-substituted aryl, alkenyl-substituted aryl, alkynyl-substituted aryl, aryl-substituted alkyl, alkenyl-substituted alkyl, alkynyl-substituted alkyl, halo substituted versions of any of the foregoing functionalized organosilanes, or combinations thereof. Specific examples include diphenyldimethoxysilane, diethyldimethoxysilane, dimethyldimethoxysilane, and dimethoxy-methyl(3,3,3-trifluoropropyl)silane. Other second silicon agents include halosilanes and dihalosilanes, such as for example, chlorotrimethylsilane and dichlorodimethylsilane.

The second silicon agent can serve as a surface passivating agent or an agent for introducing a reactive functionality, such as an amine. Exemplary second silicon agents for introducing surface primary amine groups include aminopropyltrimethoxysilane (APTMS) and aminopropyldimethylethoxysilane (APDMES).

The silicon nanoshells can be treated with one or more organic tagging agents to form tagged silicon nanoshells comprising organic surface groups derived from the tagging agent which are covalently linked to the shell surface. The surface groups can comprise an organic moiety selected from the group consisting of dyes, poly(alkylene oxide) chain segments, poly(alkylene imine) chain segments, biologically active moieties, and combinations thereof. Biologically active moieties include proteins, drugs, and compounds comprising functional groups capable of specific cell recognition. Exemplary organic tagging agents capable of reacting with nucleophilic groups (e.g., amines, thiols, alcohols) of the silicon nanoshell surface include electrophilic materials such as PEGylating reagents (i.e., a poly(ethylene glycol) having a reactive end group capable of reacting with an amine, thiol or alcohol to form a covalent bond, which are commercially available in a variety of polyether molecular weights. Other electrophilic tagging agents include electrophilic dyes, such as dansyl chloride.

Metal Nanoshells.

A method of forming a metal nanoshell comprises i) treating a star polymer occlusion complex with a pre-formed seed particle comprising a first metal, thereby forming a seeded occlusion complex and/or ii) depositing by electroless deposition on the seeded occlusion complex a second metal from a salt of the second metal, thereby forming a metal nanoshell. The metal nanoshell comprises a metal-containing shell disposed on one more star polymer occlusion complex macromolecules. The first metal and the second metal can be the same metal or different metals. The pre-formed seed and the shell can comprise ionic and/or nonionic forms of the metal. The metal-containing shell can be contiguous or noncontiguous, porous or non-porous.

The first metal and the second metal can be independently selected from the group consisting of gold, silver, platinum, tin, copper, nickel, palladium, zinc, iron, titanium, aluminum, and combinations thereof. In an embodiment, the first metal and the second metal comprise gold.

Iron Oxide Nanoshells.

A first method of forming an iron oxide nanoshell comprises treating a star polymer occlusion complex with a pre-formed iron oxide particles, thereby forming a iron oxide nanoshell, the iron oxide nanoshell comprising the iron oxide nanoparticles bound by non-covalent interactions with a hydrophilic chain segment of the star polymer occlusion complex.

A second method of forming an iron oxide nanoshell comprises treating a star polymer with mixture comprising i) a solvent, ii) a cargo material dissolved in the solvent and iii) a pre-formed iron oxide particles suspended in the solvent, thereby forming a iron oxide nanoshell, wherein the iron oxide nanoshell comprises i) the star polymer, ii) the cargo material bound by non-covalent interaction to a hydrophobic chain segment of the star polymer, and iii) the iron oxide nanoparticles bound by non-covalent interactions with a hydrophilic chain segment of the star polymer.

Also disclosed are aqueous mixtures comprising a nanoshell, wherein the nanoshell comprises a shell material disposed on one or more star polymers and/or one or more macromolecules of the star polymer occlusion complex. The star polymer occlusion complex comprises a cargo material and a star polymer, the star polymer comprising a cross-linked polymer core and 6 or more independent polymer arms covalently linked to the core, the polymer arms comprising a peripheral hydrophilic polymer chain segment and an inner hydrophobic polymer chain segment, the star polymer comprising no more than 100 ppm of any single restricted metal, the cargo material in contact with the polymer core and/or with one or more of the polymer arms. In an embodiment, the shell material comprises silicon, iron, or gold. In an embodiment the cargo material is an image contrast enhancing material. In another embodiment, the contrast enhancing material is a porphyrinoid compound. In another embodiment, the contrast enhancing material is selected from the group consisting of

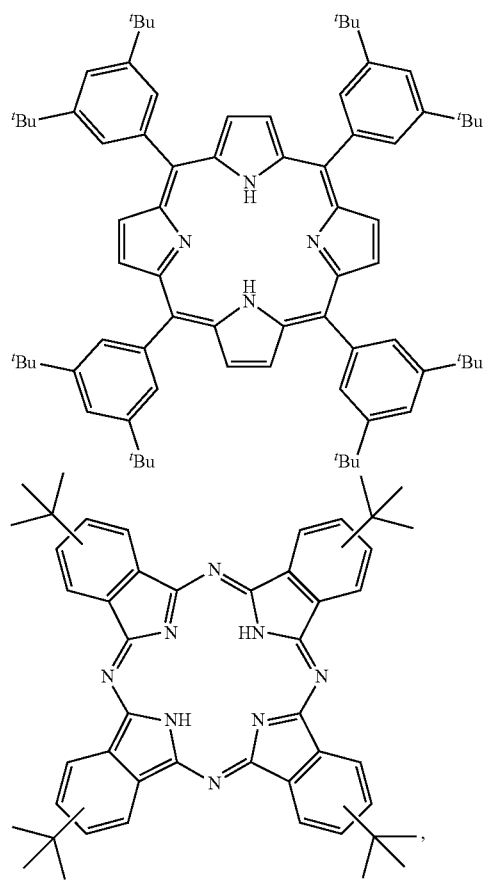

and combinations thereof.

In another embodiment, 10% to 100% of the image enhancing material is not aggregated in the star polymer occlusion complex. In another embodiment, 50% to 100% of the image enhancing material is not aggregated in the star polymer occlusion complex.

INDUSTRIAL APPLICATIONS

Further disclosed is a method of treating a cell, comprising contacting the cell with an aqueous mixture comprising the above described nanoshells. The biologically active cargo can comprise a single biologically active material or a mixture of biologically active materials. The biologically active material can be a substance selected from the group consisting of drugs, genes, dyes, image contrast enhancing materials, and combinations thereof. The biologically active cargo can be a drug, for example doxorubicin. In an embodiment, the biologically active material is a porphyrinoid compound. Cells can be contacted in vitro, ex vivo, or in vivo. Contacting preferably induces 0% to 20%, 0% to 15%, 0% to 10%, 0% to 5%, 0% to 2%, or more particularly 0% to 1% cytotoxicity. In an embodiment, contacting induces no cytotoxicity.

No restriction is placed on the type of cell that can be treated with the above-described star polymer occlusion complexes. In particular, the cells can be eukaryotic cells, mammalian cells, and more particularly rodent or human cells. The cells can be derived from various tissues, including extraembryonic or embryonic stem cells, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, dendritic cells, neurons, glia, mast cells, blood cells and leukocytes (e.g., erythrocytes, megakaryotes, lymphocytes, such as B, T and natural killer cells, macrophages, neutrophils, eosinophils, basophils, platelets, granulocytes), epithelial cells, keratinocytes, chondrocytes, osteoblasts, osteoclasts, hepatocytes, and cells of the endocrine or exocrine glands, as well as sensory cells.

The above-described nanoshells can be used as non-viral transfection vectors. The target gene is not limited to any particular type of target gene or nucleotide sequence. For example, the target gene can be a cellular gene, an endogenous gene, an oncogene, a transgene, or a viral gene including translated and non-translated RNAs. Exemplary possible target genes include: transcription factors and developmental genes (e.g., adhesion molecules, cyclin-dependent kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, ERBB2, ETSI, ETV6, FGR, FOS, FYN, HCR, HRAS, JUN, KRAS, LCK, LYN, MDM2, MLL, MYB, MYC, MYCLI, MYCN, NRAS, PIMI, PML, RET, SKP2, SRC, TALI, TCL3, and YES); tumor suppressor genes (e.g., APC, BRAI, BRCA2, CTMP, MADH4, MCC, NFI, NF2, RBI, TP53, and WTI); and enzymes (e.g., ACP desaturases and hydroxylases, ADP-glucose pyrophorylases, ATPases, alcohol dehydrogenases, amylases, amyloglucosidases, catalases, cyclooxygenases, decarboxylases, dextrinases, DNA and RNA polymerases, galactosidases, glucose oxidases, GTPases, helicases, integrases, insulinases, invertases, isomerases, kinases, lactases, lipases, lipoxygenases, lysozymes, peroxidases, phosphatases, phospholipases, phosphorylases, proteinases and peptidases, recombinases, reverse transcriptases, telomerase, including RNA and/or protein components, and topoisomerases).

The preparation and use of star polymers, star polymer occlusion complexes, and nanoshells is further illustrated by the following examples.

EXAMPLES

Materials used in the following examples are listed in Table 6.

TABLE 6

| Abbreviation | Description | Source |
|---|---|---|
| | Alpha-Methoxy-Omega-Carboxylic Acid Succinimidyl Ester Poly(Ethylene Glycol); PEG MW 750 Dalton | Iris Biotech GmbH |
| | Alpha-Methoxy-Omega-Carboxylic Acid Succinimidyl Ester Poly(Ethylene Glycol); PEG MW 2000 Dalton | Iris Biotech GmbH |
| | Alpha-Methoxy-Omega-Carboxylic Acid Succinimidyl Ester Poly(Ethylene Glycol); PEG MW 5000 Dalton | Iris Biotech GmbH |
| | Alpha-Methoxy-Omega-Carboxylic Acid Succinimidyl Ester Poly(Ethylene Glycol) PEG MW 10000 Dalton | Iris Biotech GmbH |
| | Alpha-Methoxy-Omega-Mercapto Poly(Ethylene Glycol); PEG MW 5000 Dalton | Iris Biotech GmbH |
| DMAEMA | 2-(N,N-Dimethylamino)Ethyl Methacrylate | Sigma Aldrich |
| APTMS | 3-Aminopropyltrimethoxy Silane | Sigma Aldrich |
| APDMES | 3-Aminoproplyldimethylethoxysilane | Sigma Aldrich |
| DPDMS | Diphenyldimethoxysilane | Sigma Aldrich |
| TEOS | Tetraethylorthosilicate | Sigma Aldrich |
| TMOS | Tetramethylorthosilicate | Sigma Aldrich |
| DTBP | 5,10,15,20-(3,5-Ditertbutylphenyl) Porphyrin | Synthesized according to literature proceedure below |
| DANSYL-Cl | 5-Dimethylaminonaphthalen-1-Sulfonyl Chloride | Sigma Aldrich |
| DPDMS | Diphenyldimethoxysilane | Gelest |
| HMDS | Hexamethyldisilazane | Sigma Aldrich |
| THF | Tetrahydrofuran | Sigma Aldrich |
| | 3-(t-Butyldimethylsilyloxy)-1-Propyl Lithium | FMC Lithium Division |
| $Bu_4N^+F^-$ | Tetrabutylammonium Fluoride | Sigma Aldrich |
| | 2-Bromoisobutyryl Bromide | Sigma Aldrich |
| | Hydroxylamine Amine HCl | Sigma Aldrich |
| THPC | Tetrakis(Hydroxymethyl)Phosphonium Chloride | Sigma Aldrich |
| | Gold (III) Chloride | Sigma Aldrich |
| | Iron(III)Acetylacetone | Sigma Aldrich |
| | 30% Ammonium hydroxide | JT Baker |
| BOD | 4-4'-Bioxepanyl-7,7'-dione | TCI America |
| BNPEG | Boc-protected amino-poly(ethylene glycol) (Mn = 5000) | Iris Biotech GmbH |
| TBD | 1,5,7-Triazabicyclo[4.4.0]dec-5-ene (organocatalyst) | Sigma Aldrich |

Instrumentation. $^1$H NMR spectra were obtained on a Bruker Avance 2000 spectrometer (400 MHz) using 5 mm o.d. tubes and were referenced to internal solvent residue ($^1$H, CDCl$_3$: delta=7.24). Analytical Gel Permeation Chromatography (GPC) using Waters high resolution columns HR1, HR2, HR4E and HR5E (flow rate 1 mL/min, THF) was used to determine molecular weight distributions, $M_w/M_n$, of polymer samples with respect to linear polystyrene standards. Absorption studies were performed using a 8453 Agilent UV-VIS spectrophotomer. Nanoshells were spin-coated on a silicon wafer at 3000 rpms and were dried on a thermoplate for one minute at 110° C. prior to characterization using a Hitachi S-4700 cold field emission scanning electron microscope. The nanoshells were deposited on copper grids and dried under vaccum for further characterization using a Topcon 002B transmission electron microscope running at 200 kV.

Star Polymer.

The star polymers used in the following examples had a hydrodynamic radius of 19 nm and each polymer contained approximately 33 arms made of a polystyrene core (3 kDa), and a dimethylaminoethylmethacrylate arm of either (6 or 8 kDa). The hydrophobic polystyrene core is capable of sequestering hydrophobic organic dyes and the polyamine shell provides both water solubility and nucleation sites for the template. Non-aggregating porphyrin dyes were selected to use in this work owing to their strong absorption profile across a wide section of the UV-VIS spectrum.

The star polymer architecture used in forming the occlusion complexes below with a hydrophobic cargo material has i) a crosslinked hydrophobic core, ii) at least 6 independent arms covalently bound at one end to the hydrophobic core, wherein the arms comprise a) respective inner hydrophobic segments bound to the core and b) respective peripheral hydrophilic segments attached to the inner hydrophobic segments, and iii) a plurality of functionalities along the peripheral hydrophilic segments of the arms to facilitate interaction with a specific inorganic nanoshell precursor. More specifically, the star polymers prepared in the following examples comprise a crosslinked polystyrene core and about 33 arms comprising respective inner hydrophobic segments of polystyrene and respective peripheral hydrophilic segments comprising poly(2-(N,N-dimethylamino) ethyl methacrylate) (DMAEMA)

Preparation of Star Polymer SP-1.

(A). Synthesis of Precursor 1, a "Protected" 3-(tert-butyldimethylsilyloxy)-1-propyl Terminated Polystyrene Star Polymer (Typical Procedure).

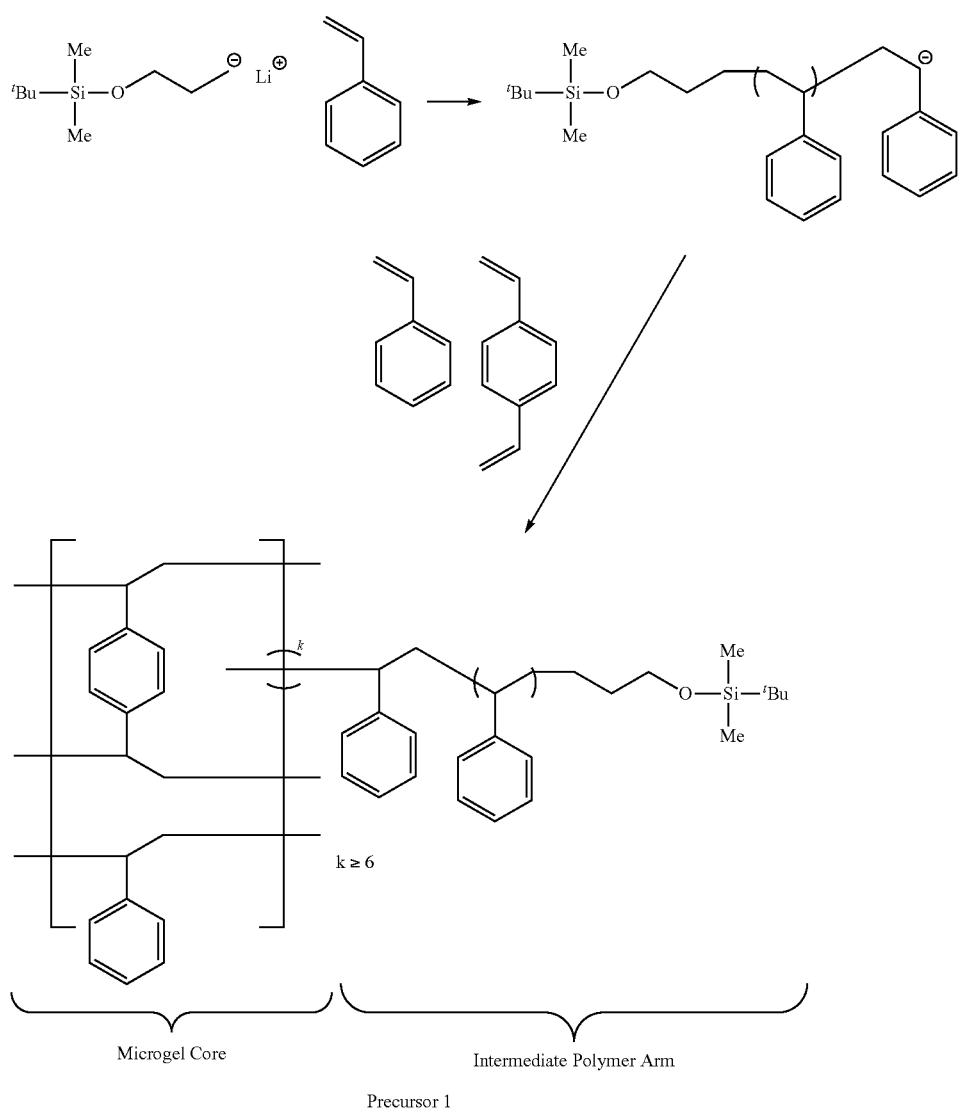

Precursor 1

3-(t-Butyldimethylsilyloxy)-1-propyl lithium (0.60 mL, 20 wt. % solution in cyclohexane) was added to a stirred solution of styrene (12.00 mL) in a cyclohexane (200 mL) and THF (10 mL) mixture under an argon atmosphere. After 20 min an aliquot (approximately 2 mL) was taken, quenched in degassed MeOH (approx. 150 mL) and a representative sample of the "free" polystyrene arm collected by filtration. A mixture of p-divinylbenzene (2.70 mL) and styrene (0.12 mL) in cyclohexane (3.00 mL) was added and the reaction mixture stirred for a further 40 min. The reaction solution was then quenched by slow addition to a rapidly stirred solution of MeOH and EtOH (1.5 L, 1:1). The precipitate formed was isolated by filtration and air dried to a constant weight. The crude star-polymer was then dissolved in $CH_2Cl_2$ (100 mL) before the slow addition of acetone (150 mL) and then isopropyl alcohol (30 mL). The solution was allowed to stand until the product formed a substantial oily layer on the bottom of the container. The mixture was decanted allowing isolation of the oil which was then dried in a vacuum oven to constant weight affording the "protected" intermediate star polymer (Precursor 1) (9.5 g). $^1$H NMR (400 MHz, $CDCl_3$) delta=0.18 (br s, 6H) 0.85 (br s, 9H), 1.44 (br s, 330 H) 1.85 (br s, 165 H), 3.35 (br s, 2 H) 6.50-6.60 (br m, 330 H), 7.10 (br s, 495 H). Analytical GPC: $M_w/M_n$=1.15. Light Scattering: $M_w$=600 000 g/mol, $M_w/M_n$=1.09, $R_h$(avg) 10.8 nm. $^1$H NMR (400 MHz, $CDCl_3$) analysis of the "free arm" sample indicated arm length of approx. 165 repeat units. This implied the approximate number of "arms" in the star-polymer was about 36.

(B). Synthesis of Precursor 2, a "Deprotected" Hydroxy-Terminated Polystyrene Star Polymer (Typical Procedure).

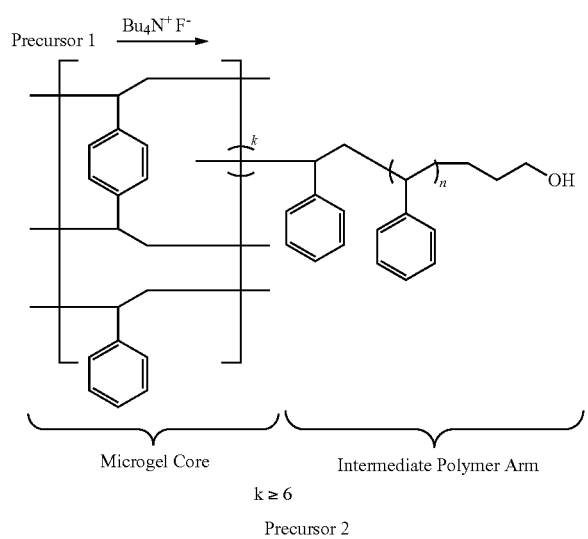

Precursor 1 (9.0 g) was dissolved in THF (9.0 mL) and tetrabutylammonium fluoride (1.0 M solution in THF, 9.0 mL) was added. The reaction solution was stirred for 60 hours at room temperature before being warmed to 50° C. for 1 hour. The solution was allowed to cool to room temperature before it was slowly added to MeOH (1 L) with rapid stirring. The precipitate formed was isolated by filtration and air dried to a constant weight to afford the "deprotected" Precursor 2 (8.5 g). $^1$H NMR (400 MHz, CDCl$_3$) delta=1.44 (br s, 330 H) 1.85 (br s, 165 H), 3.45 (br s, 2 H) 6.50-6.60 (br m, 330 H), 7.10 (br s, 495 H). Analytical GPC: $M_w/M_n$=1.14. Light Scattering: $M_w$=608 000 g/mol, $M_w/M_n$=1.14, $R_h$(THF, average) 10.6 nm.

(C). Synthesis of Precursor 3, a Polystyrene Star Polymer Peripherally Functionalized with Atom Transfer Radical Polymerization (ATRP)-Initiator Moiety.

A solution of 2-bromoisobutyryl bromide (1.4 g, 4 equivalents per star polymer alcohol end group) in anhydrous dichloromethane (30 mL) was added dropwise over 15 minutes to a solution of hydroxy star polymer Precursor 2 (5.0 g) and triethylamine (0.75 g) in anhydrous dichloromethane (30 mL) at 0° C. The mixture was allowed to warm up to room temperature for 14 hours, then heated to a gentle reflux for 4 hours. Pure product Precursor 3 was obtained after repeated precipitation into methanol. GPC and DLS analysis showed no significant change from that of the hydroxy star polymer starting material. 1H NMR (CDCl3, 4000 MHz) characterization of the product confirmed quantitative end-group transformation.

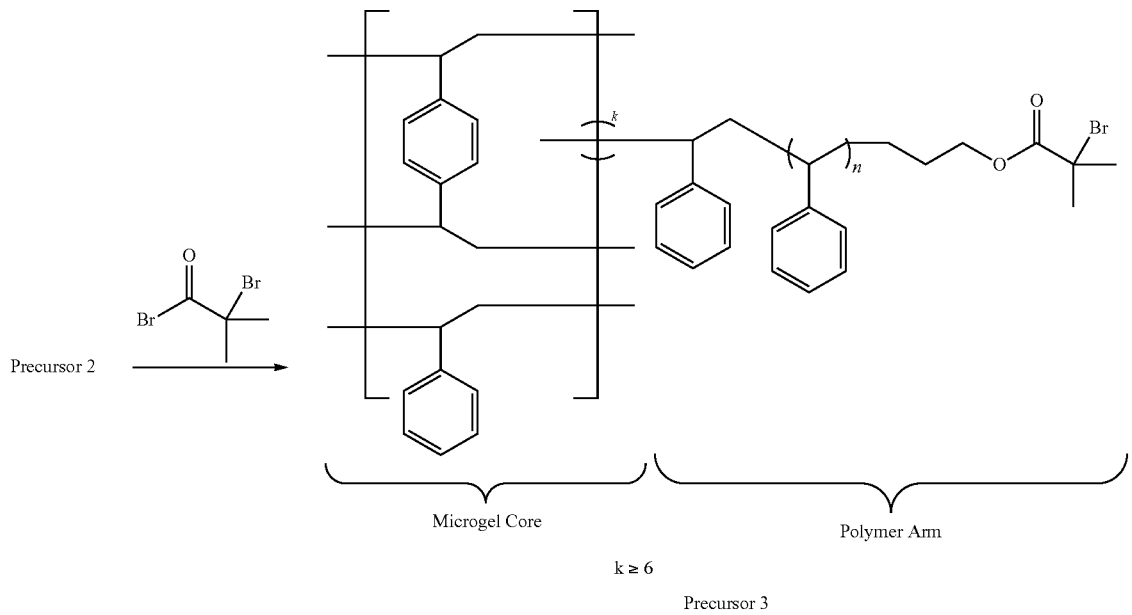

(D). Synthesis of SP-1, a Polystyrene Star Polymer Terminated with poly(2-(N,N-dimethylamino)ethyl methacrylate) (DMAEMA)

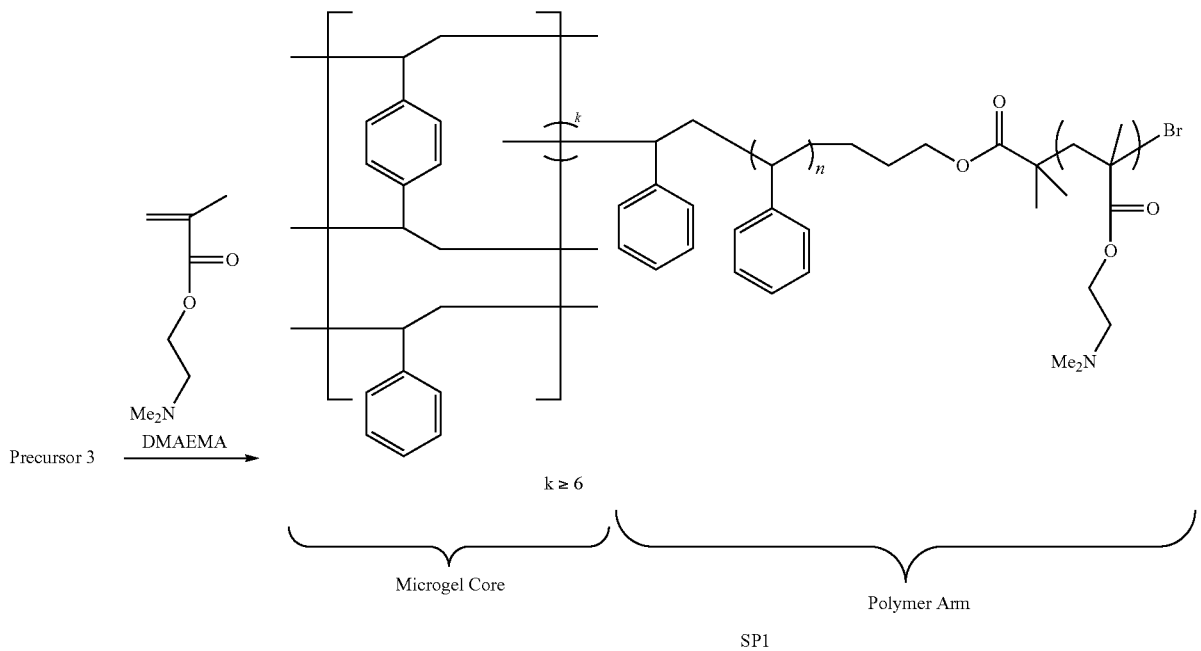

ATRP-initiator peripherally functional polystyrene (PS) star polymer Precursor 3 (0.3 g), N,N-dimethylaminoethyl-methacrylate (DMAEMA) (2.3 g), copper(I) chloride (5.4 mg) and 4,4'-nonyl-2,2'-bipyridine (45.0 mg) were dissolved in toluene (5.0 mL). The solution was degassed and sealed under a nitrogen atmosphere before being heated to 90° C. for 15 hours. The reaction solution was then cooled and added to hexane (50 mL) with rapid stirring. The precipitate thus formed was isolated, dissolved in methylene chloride and again added to hexane (50 mL) with rapid stirring. The precipitate thus formed was isolated and air dried to a constant weight to produce star polymer SP-1 (0.4 g) as a white solid. $^1$H NMR (400 MHz, CDCl$_3$) delta (ppm)=0.78 (br, s, 6H), 0.90 (br s, 40 H), 1.08 (br s, 20 H), 1.45 (br s, 60 H), 1.86 (br s, 80 H), 2.33 (br s, 120 H), 2.63 (br s 40), 4.11 (br s, 40), 6.50-6.60 (br m, 66 H), 7.13 (br s, 99 H). DLS (THF): $M_w$=190,000 g/mol, $M_w/M_n$=1.05, hydrodynamic radius $R_{h(avg)}$=8.5 nm.

Preparation of Star Polymer SP-2.

The above described procedure for SP-1 was used to prepare star polymer SP-2, using DMAEMA (2.6 g) and 60 min reaction time.

Preparation of Star Polymer SP-3.

The above described procedure for SP-1 was used to prepare star polymer SP-3, using DMAEMA (2.6 g) and 85 min reaction time.

Table 7 summarizes the properties of SP-1, SP-2 and SP-3. "PS component" and "DMAEMA component" in Table 7 refer to the average molecular weight of these components in the star polymer, as determined by NMR. Radius "d" refers to the hydrodynamic radius as determined by light scattering.

TABLE 7

| Sample | # of Arms | MW (kDa) by NMR | | Light Scattering | | |
| --- | --- | --- | --- | --- | --- | --- |
| | | Star | PS component | DMAEMA component | MW (kDa) | Radius d (nm) | GPC (PDI) |
| SP-1 | 33 | 231 | 3.3 | 3.7 | 190 | 18 | 1.12 |
| SP-2 | 33 | 211 | 3.3 | 3.1 | 274 | 22 | 1.16 |
| SP-3 | 33 | 320 | 3.3 | 6.4 | 283 | 23.6 | 1.17 |

General Procedure for Preparation of Star Polymer Occlusion Complex.

As shown in the schematic reaction diagram of FIG. 2, a star polymer occlusion complex comprises a cargo material occluded in a star polymer. The cargo material can be bound by non-covalent interactions or covalent interactions. In this example the cargo is a hydrophobic dye. For illustration purposes not meant to be limiting, the molecular structure depicted in FIG. 2 shows three molecules of a dye occluded in the star polymer. The number of occluded molecules of cargo material can be one or more. The hydrophobic dye is believed to be in contact with the inner hydrophobic segment of the polymer arms and the hydrophobic core.

The following general procedure employs hydrophobic solvatochromic dyes as representative therapeutically useful materials (e.g., pharmaceuticals) to prepare water based star polymer occlusion complexes. The nanoparticles of amphiphilic star polymers are occluded with the dye using hydrophobic/hydrophilic interactions. A solution was prepared containing hydrophobic dye material (5 mg) and star-polymer (25.0 mg, approximately 0.1 micromoles) in THF (0.1 mL, about 10 mM). The solution was added dropwise to water (0.9 mL) with rapid stirring, causing the water to rapidly and uniformly color from the dye. Excess solid dye material not adsorbed to the star polymer was removed by passing the mixture through a 0.45 micrometer syringe filter, thereby forming a clear and uniformly colored aqueous solution. Residual THF was removed under vacuum. The further addition of water had no visible effect on the homogeneity of the solution. Ultraviolet-visible (UV-VIS) absorption spectra of the aqueous formulations containing the various solvatochromic dye materials were used to demonstrate the association of these model hydrophobic materials with the star polymer in the aqueous environment.

Preparation of Occlusion Complex, OC-1, with Porphyrin Dye DTBP.

The above-described procedure was used to prepare star polymer occlusion complex OC-1 from star polymer SP-1 and 5,10,15,20-(3,5-ditertbutylphenyl)porphyrin (M=2H) (DTBP).

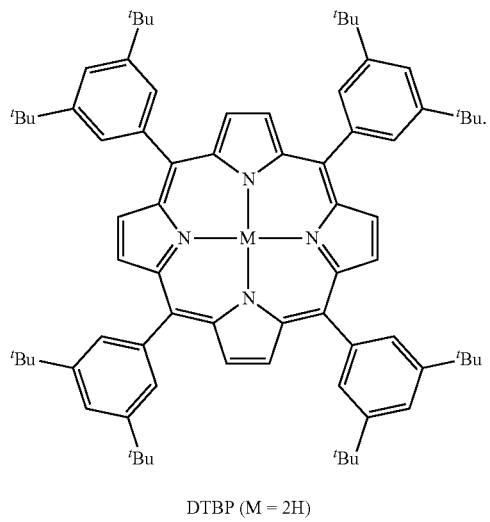

DTBP (M = 2H)

Figure 3:
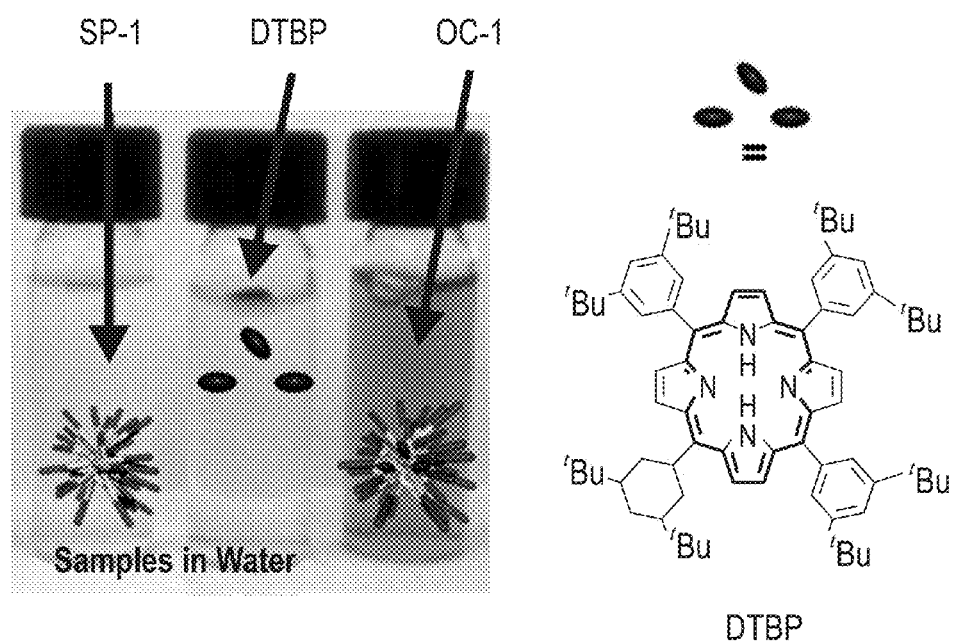
FIG. 3 is a photograph of three vials containing (from the left), star polymer SP-1 (aqueous solution), porphyrin dye (DTBP) (aqueous suspension), and a star polymer occlusion complex (OC-1) prepared from SP-1 and DTBP (aqueous solution).

FIG. 3 is a photograph of side by side vials containing from the left i) the star polymer SP-1 alone in water, ii) the porphyrin dye DTBP alone in water, and iii) the star polymer occlusion complex OC-1. Overlaying each vial is a three-dimensional drawing of the corresponding material. The left vial containing the star polymer SP-1 in water is clear and colorless. The middle vial containing the porphyrin dye DTBP in water is clear with the DTBP precipitated and floating on the top of the aqueous phase. The right vial containing the star polymer occlusion complex OC-1 in water is clear and has a magenta hue.

Preparation of Inorganic Nanoshells.

I. General Preparation of Gold Nanoshells:

Gold seeds (1 nm to 3 nm in average diameter) were prepared according to Pham et al., Langmuir 2002, 18, pages 4915-4920. In summary, NaOH (4.5 mL, 0.2 M) was added into 45.5 mL of Millipore water and the solution was stirred for 2 minutes at 600 rpm. Subsequently, 12 microliters of 80% tetrakis(hydroxymethyl)phosphonium chloride (THPC) that was diluted in 1 mL of Millipore water was added to the mixture and stirred for another 2 minutes. The pH of the solution was about 12. The final step was the fast addition of gold (III) chloride (2 mL, 0.029 M). The solution changed from colorless to light brown when the gold (III) chloride was added. The resulting solution of gold seeds was stirred for another 5 minutes. The aqueous solution containing the star polymer occlusion complex (5 mL) was then mixed with an aqueous solution of gold seeds (5 mL). The combined solution was diluted with water (10 mL) and stirred overnight. The solution was dialyzed against water using a cellulose dialysis membrane with 12,000 Da to 14,000 Da molecular weight cut-off (MWCO) for 24 hours. The dialyzed solution was stored at 4° C., thereby producing a gold seeded occlusion complex. A three-dimensional drawing representation of the gold seeded occlusion complex formed in this manner is shown in FIG. 2. A gold (III) chloride solution (0.0955 M, 1.74 mL) was diluted with 98.2 mL of Millipore water and potassium carbonate (100 mg) was added. The resulting solution was dark aged 24 hours to form a gold(III) hydroxide solution for the following growth step. The gold growth step was initiated by mixing the gold hydroxide solution (14.8 mL) of the solution of gold seeded occlusion complex (9 mL) with vortex agitation at 650 rpm for one minute. The hydroxylamine hydrochloride solution (freshly prepared at 0.026%, 20 mL) was then added to the mixture over 45 seconds. The final solution was stirred for another 15 minutes and stored at 4° C. prior to further purification steps. The gold nanoshell solution was dialysed against water for 24 hours and then against methanol for 24 hours (cellulose membrane with 12,000 Da to 14,000 Da MWCO). The gold nanoshell particles were isolated by freeze-drying.

The particle size of gold nanoshells depends on the ratio of the volume of the gold seeded star polymer solution to the volume of the hydroxylamine solution added, the total volume and/or reagent concentration of the growth solution reagents (i.e., gold hydroxide, gold seeded star polymer solution, and hydroxylamine hydrochloride), and addition rate of hydroxylamine, as shown below in Table 8 below. For example, to achieve an average of 110 nm particles (in diameter), the volume of gold hydroxide, gold seeded star polymer solution, and hydroxylamine hydrochloride was 14.8 mL, 9 mL, and 20 mL, respectively.

EXAMPLE 1

Preparation of Gold Nanoshells, AuNS-1

Figure 4A:
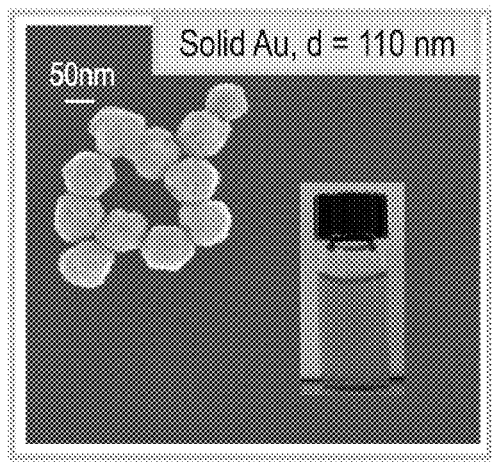
FIG. 4A is a scanning electron micrograph (SEM) of commercially available solid gold nanoparticles (110 nm). The inset picture is an aqueous solution of the solid gold particles. The solution has a magenta hue.
Figure 4B:
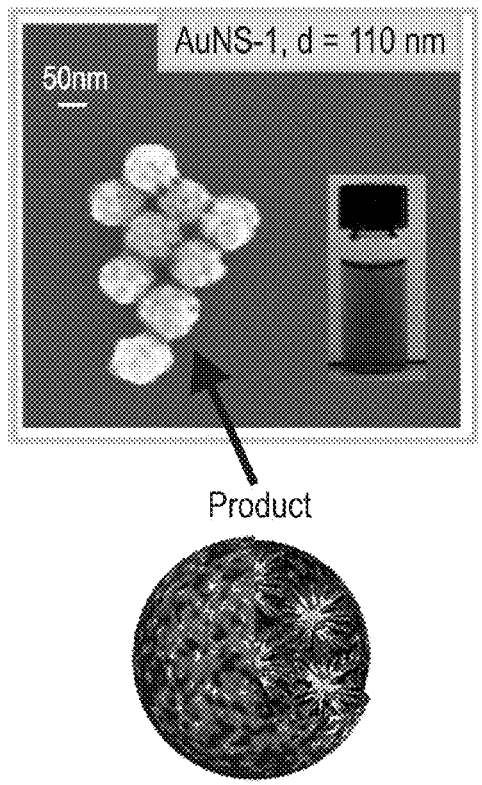
FIG. 4B is an SEM of similar sized (110 nm) gold nanoshells AuNS-1 prepared from a star polymer occlusion complex, OC-1, comprising porphyrin dye DTBP. A drawing representation of the gold nanoshells AuNS-1 is shown below the SEM, showing the shell encompassing multiple independent macromolecules of star polymer occlusion complex OC-1. The inset picture is an aqueous solution of the gold nanoshells AuNS-1. The solution has a blue black hue.
Figure 4C:
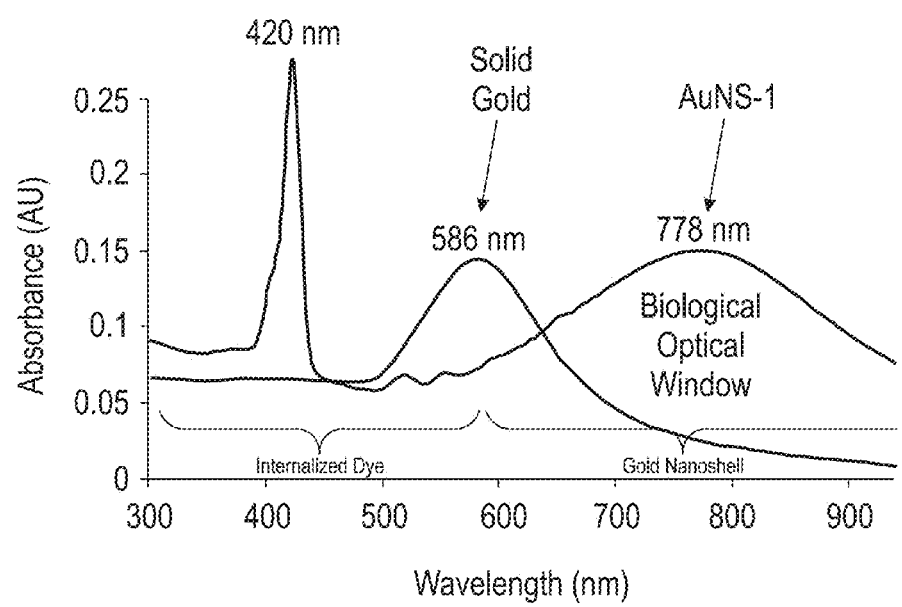
FIG. 4C is a graph of UV-VIS absorption spectra of commercially available solid gold nanoparticles (110 nm) versus similar sized gold nanoshells AuNS-1 prepared from star polymer occlusion complex OC-1. Only the gold nanoshells AuNS-1 absorb strongly in the "biological window" (ca. 650 nm to 950 nm).

The above described procedure was used to prepare gold nanoshells AuNS-1 from star polymer occlusion complex OC-1. The average particle diameter was 110 nm as determined from SEM images. FIGS. 4A and 4B are SEM images comparing commercially available solid gold particles and gold nanoshells AuNS-1, respectively. The particle size in each photograph is similar, about 110 nm. This particle size is suitable, for example, for systemic in vivo delivery of a biologically active material such as a drug. Each AuNS-1 nanoparticle is believed to encapsulate multiple macromolecules of star polymer occlusion complex, as shown in the three-dimensional drawing representation of FIG. 4B. The photographic inset images in the TEM images of FIGS. 4A and 4B are aqueous solutions of the solid gold nanoparticles and AuNS-1 nanoparticles, respectively. The solid gold nanoparticle solution in FIG. 4A is magenta. The AuNS-1 solution in FIG. 4B is dark blue. FIG. 4C compares the absorption spectra of the solid gold nanoparticles and AuNS-1. The solid gold nanoparticles have a peak absorbance at 586 nm, whereas AuNS-1 has peak absorbances at 420 nm (for the porphyrin DTBP) and 778 nm. Only the AuNS-1 solution absorbs in the biological optical window of about 600 nm to more than 1000 nm.

Effects of Changing Various Reaction Parameters.

Different gold nanoshell particle sizes and near infrared (NIR) absorptions can be achieved by modifying synthesis conditions (e.g., growth solution concentration, seed amount per star polymer and/or growth time). The following Examples 2 and 3 demonstrate the effect of varying different reaction condition parameters.

EXAMPLE 2

Preparation of Gold Nanoshells AuNS-2 from SP-1

The above procedure used to form AuNS-1 was also used to form AuNS-2 but using star polymer SP-1 as the template (rather than its occlusion complex OC-1), and using 6 mL of gold seeded star polymer SP-1 solution (rather than 9 ml of OC-1 solution), half the volume of hydroxylamine solution, and an addition time for the hydroxylamine solution of 20 min.

EXAMPLE 3

Preparation of Gold Nanoshells AuNS-3 from SP-1

The above procedure used to form AuNS-1 was also used to form AuNS-3, but with 6 mL of gold seeded star polymer occlusion complex OC-1 solution, half the volume of hydroxylamine solution, and an addition time for the hydroxylamine solution of 5 min. Table 8 summarizes the effects of varying different reaction parameters on the average particle diameter of the gold nanoshells formed.

TABLE 8

| Sample | | Gold Seeded Star Polymer Solution Added (mL) | AuOH Solution Added (mL) | Hydroxylamine Solution Added (mg/mL) | Hydroxylamine Addition time (min) | Average Particle Diameter (nm) |
|---|---|---|---|---|---|---|
| Ex. 1 | AuNS-1 | 9 | 14.8 | 5.2/20 | 0.75 | 110 |
| Ex. 2 | AuNS-2 | 6 | 14.8 | 2.6/10 | 20 | 90 |
| Ex. 3 | AuNS-3 | 6 | 14.8 | 2.6/10 | 5 | 200 |

EXAMPLE 4

Applying a Second Shell to the Gold Nanoshells—Preparation of Gold Nanoshell AuNS-4 from AuNS-2

The gold nanoshells can themselves be used to initiate a second growth step to provide an additional shell surrounding the original gold nanoshell. For example, gold nanoshell AuNS-4 was formed using the above procedure used to form AuNS-1 but using gold nanoshell AuNS-2 instead of the gold "seeded" template OC-1 to provide AuNS-4 with a second, additional gold nanoshell (particle size increased from an average of 90 nm for AuNS-2 to an average of 220 nm for AuNS-4).

Figure 5A:
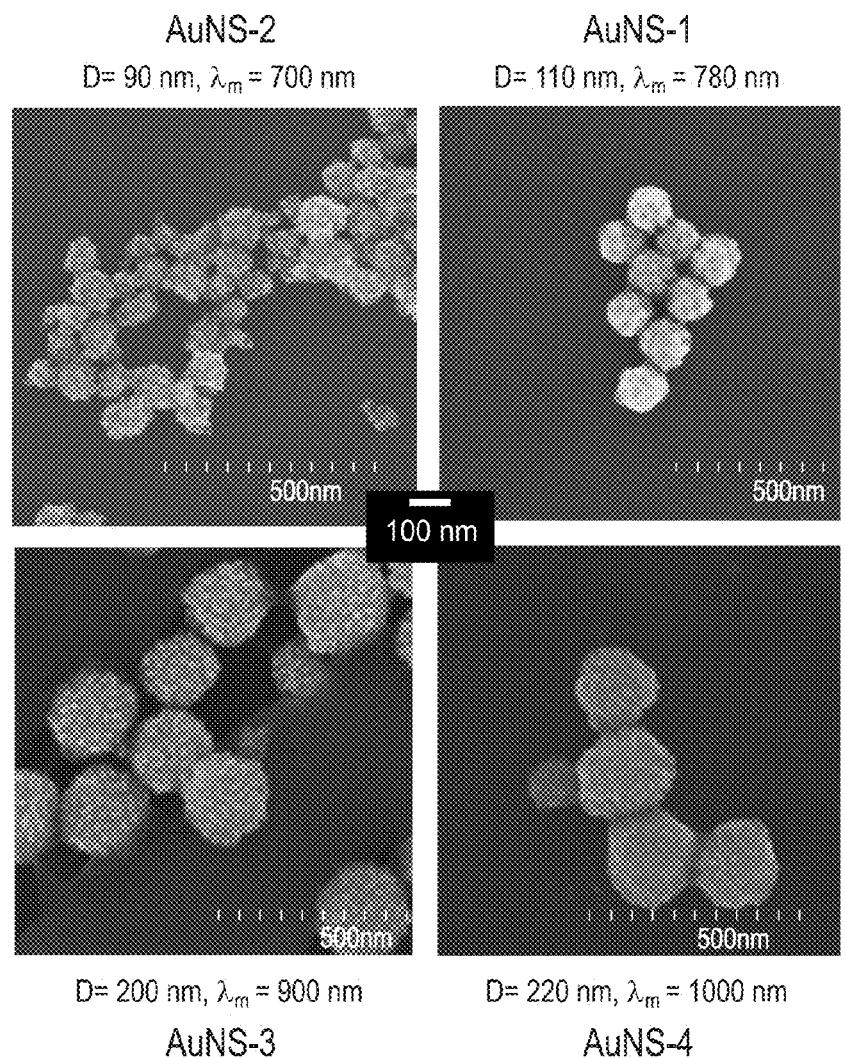
FIG. 5A is a set of four SEMs showing how variation of the gold nanoshell thickness affects the absorbance maxima of gold nanoshells AuNS-1 to AuNS-4. The thickness varies in response to the ratio of the volume of the gold seeded star polymer solution to the volume of the hydroxylamine solution added, the total volume and/or reagent concentration of the growth solution, and/or the addition rate of the growth solution to the solution of the seeded star polymer occlusion complex.
Figure 5B:
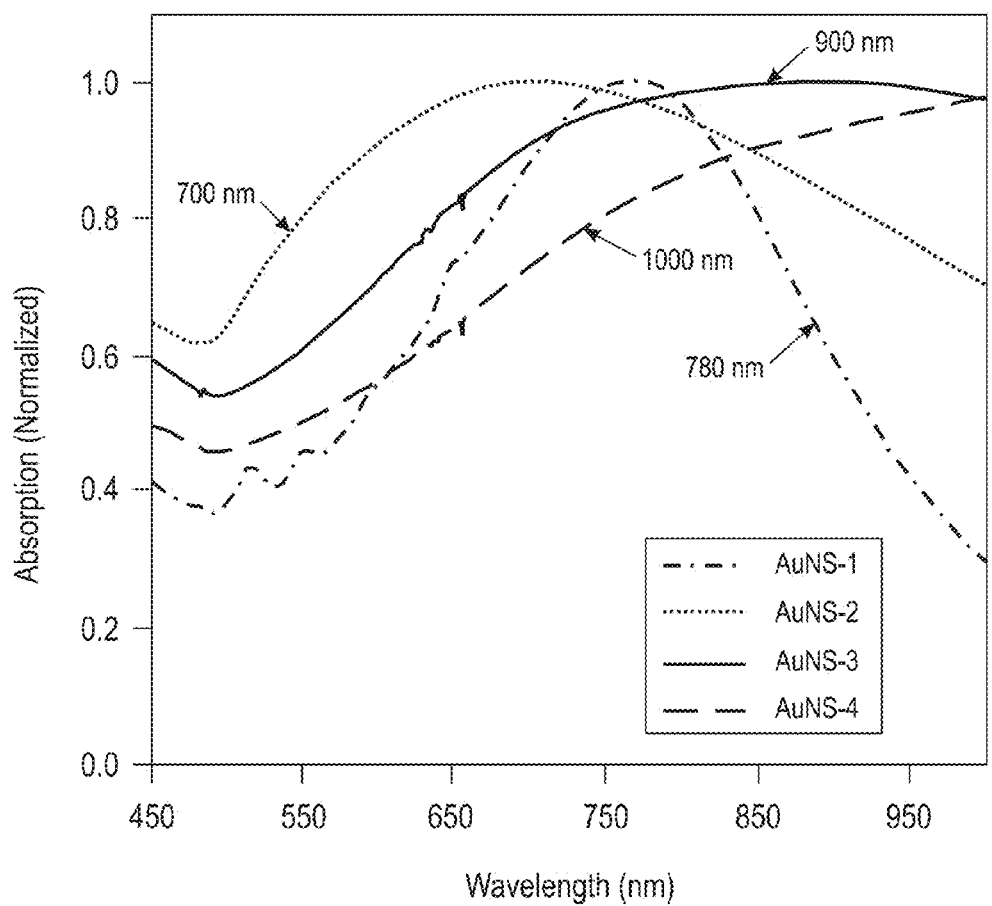
FIG. 5B is a graph containing visible-near infrared (VIS-NIR) absorption curves of gold nanoshells AuNS-1 to AuNS-4, which show a red shift in the absorbance with increasing particle size.
Figure 5C:
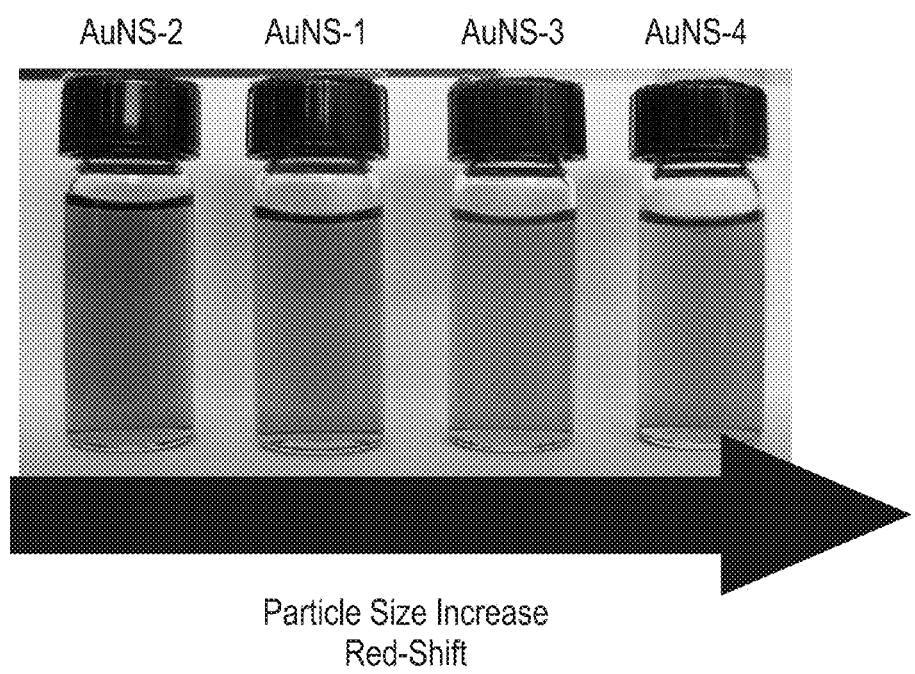
FIG. 5C is a photograph of four aqueous solutions of gold nanoshells AuNS-1 to AuNS-4. The hue shifts from magenta-purple on the left to blue-black on the right.

FIG. 5A is a series of SEMs of AuNS-1 to AuNS-4 having average particle sizes of 110 nm, 90 nm, 200 nm, and 220 nm, respectively. FIG. 5B is a graph showing the partial VIS-NIR absorption curves of AuNS-1 to AuNS-4, showing a red shift in the color of the solutions with increasing particle size. FIG. 5C is a photograph of the aqueous solutions of AuNS-1 to AuNS-4, showing a color shift from magenta-purple on the left to deep blue on the right.

EXAMPLE 5

Preparation of AuNS-5, a PEGylated Gold Nanoshell from AuNS-1

Figure 5D:
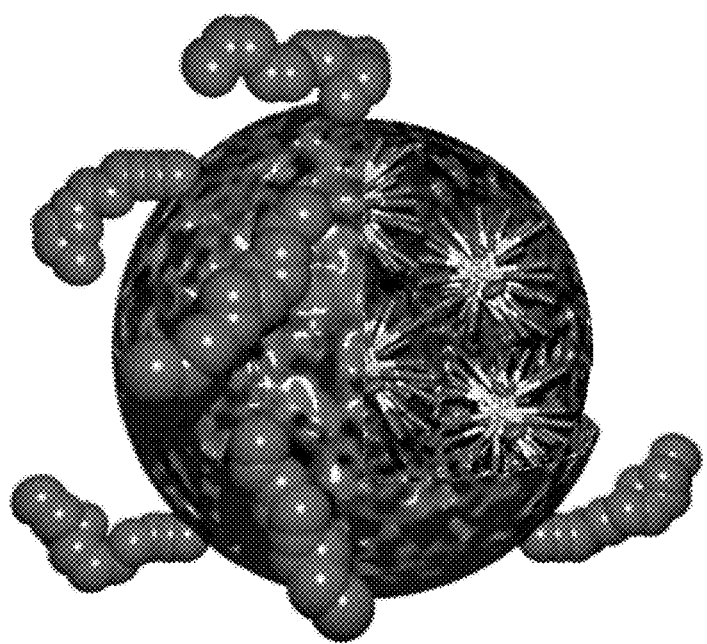
FIG. 5D is a three-dimensional drawing representation of AuNS-5 formed from contacting the surface of AuNS-1 with thiol-functionalized poly(ethylene glycol) (PEG).
Figure 5E:
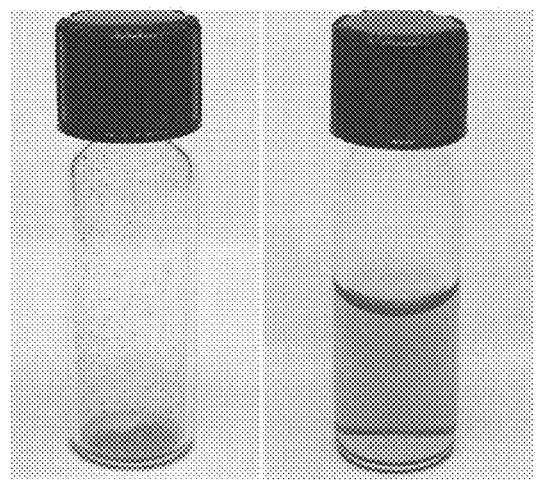
FIG. 5E is a photograph of vials containing AuNS-5 as (left) a lyophilized powder and (right) as an aqueous solution. Both the solution and the powder have a blue hue.

FIG. 5D is a three-dimensional drawing representation showing the structure of a gold nanoshell about a star polymer occlusion complex having an additional surface coating of functionalized organic material about the surface of the gold nanoshell The gold nanoshells can further be functionalized through the addition of an exterior coating of functionalized organic materials (organic tagging agents). For example, gold nanoshell AuNS-1 was contacted in solution with alpha-methoxy-omega-mercapto poly(ethylene glycol) PEGylating agent (PEG MW 5,000 Dalton) as the organic tagging agent to provide surface modified PEG-functionalized gold nanoshell AuNS-5, which was further purified by dialysis (MWCO=14 kDa) against water before being freeze dried to a lyophilized powder. The PEG chain is covalently linked to the surface of the tagged nanoshell through the mercapto end group. FIG. 5E is a photograph of vials containing PEG functionalized gold nanoshell AuNS-5 as (left) a lyophilized powder and (right) an aqueous solution. Both the powder and the solution have a blue hue.

Effect of pH.

Aggregation of the star polymer occlusion complex and size of the gold nanoshell can be controlled through pH, as shown in the following Examples 6 and 7, and in the three dimensional drawing representation of FIG. 6A. The unimolecular star polymer occlusion complex OC-1 has an average particle size of 20 nm to 25 nm.

EXAMPLE 6

Preparation of Gold Nanoshells, AuNS-6, at pH 3.18

The above procedure used to form AuNS-1 was used to form AuNS-6 but with the gold seed solution being adjusted to pH 3.18 by the addition of aqueous HCl prior to the growth step.

EXAMPLE 7

Preparation of Gold Nanoshells, AuNS-7, at pH 8.4

The above procedure used to form AuNS-1 was used to form AuNS-7 but with the gold seed solution being adjusted to pH 8.4 by the addition of aqueous NaOH prior to the growth step.

Figure 6B:
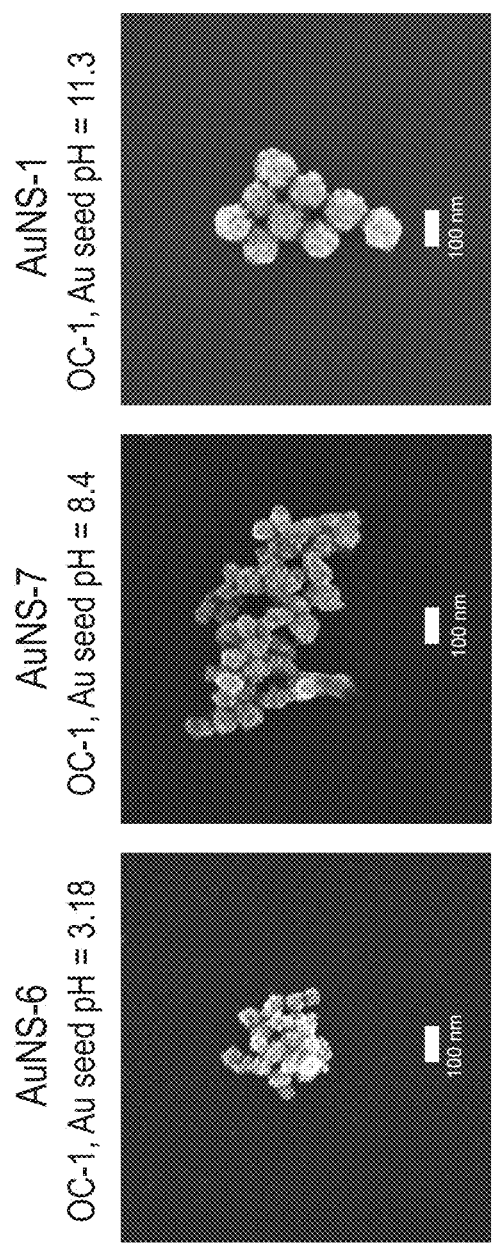
FIG. 6B is a set of three SEMs of gold nanoshells AuNS-6, AuNS-7, and AuNS-1 prepared at pH 3.18 (average particle size 50 nm), 8.4 (average particle size 80 nm), and 11.3 (average particle size 110 nm), respectively.

FIG. 6B is a series of scanning electron micrographs (SEM) of the gold nanoshells AuNS-6 and AuNS-7 prepared in Examples 6 and 7, respectively, and AuNS-1. The average particle size as measured from SEM images of AuNS-6 was 50 nm. The average particle size of AuNS-7 was 80 nm. These are compared to the SEM image of AuNS-1 (prepared with an inherent seed solution pH of 11.3), which had an average particle size of 110 nm.

Effect of Star Polymer Amine Content.

The size of the gold nanoshell can be controlled through the pendant amine content (DMAEMA) of the star polymer, as shown in the following Examples 8 and 9. The unimolecular star polymer occlusion complexes OC-1 to OC-3 have an average particle size of 18 nm to 24 nm.

EXAMPLE 8

Preparation of Gold Nanoshells, AuNS-8 Using Star Polymer SP-2(SP-2 Particle Diameter of 22 nm, Table 7)

The above procedure used in forming AuNS-1 was used to form AuNS-8 but with the template being the occlusion complex OC-2 formed from the star polymer SP-2 (Table 7).

EXAMPLE 9

Preparation of Gold Nanoshells, AuNS-9 with Star Polymer SP-3 (SP-3 Particle Diameter of 24 nm, Table 7)

The above procedure used in forming AuNS-1 was used to form AuNS-9 but with the template being the occlusion complex OC-3 formed from the star polymer SP-3 (Table 7). AuNS-9 is believed to contain on average 1 to 2 macromolecules of OC-2.

Figure 7:
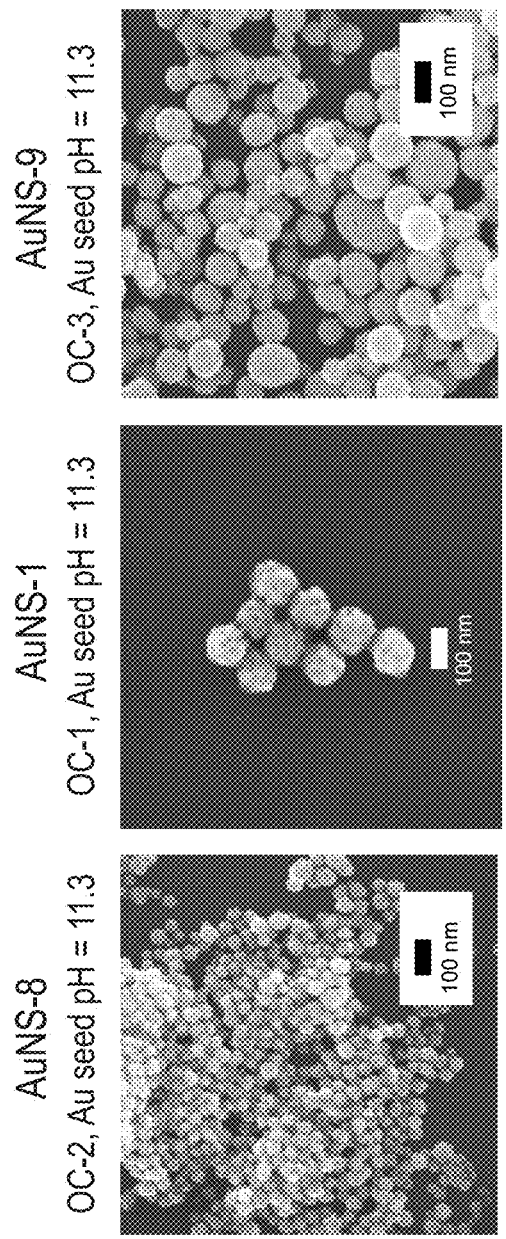
FIG. 7 is a set of three SEMs showing the effect of amine monomer (DMAEMA) content of the star polymer on the respective size and uniformity of gold nanoshells. Star polymers SP-1, SP-2 and SP-3 (Table 7) were used to prepare star polymer occlusion complexes OC-1, OC-2 and OC-3, respectively. OC-1, OC-2 and OC-3 were used to prepare gold nanoshells AuNS-1, AuNS-8, and AuNS-9, respectively, under otherwise identical reaction conditions. The star polymers templates have similar particles sizes (18 nm to 22 nm), but the resulting gold nanoshells have average particle sizes that vary greatly, increasing with amine content of the star polymer template.

FIG. 7 is a series of scanning electron micrographs (SEM) of the gold nanoshells AuNS-8 (Example 8), AuNS-1, and AuNS-9 (Example 9). The average particle size and polydispersity increase with amine content. The average particle size as of AuNS-8 was 50 nm. AuNS-8 is believed to contain on average 1 to 2 macromolecules of OC-2. The average particle size as of AuNS-9 was 120 nm. AuNS-9 was more polydisperse, having a particle size range of about 50 nm to about 150 nm.

Other Characterizations of Gold Nanoshells.

Figure 8A:
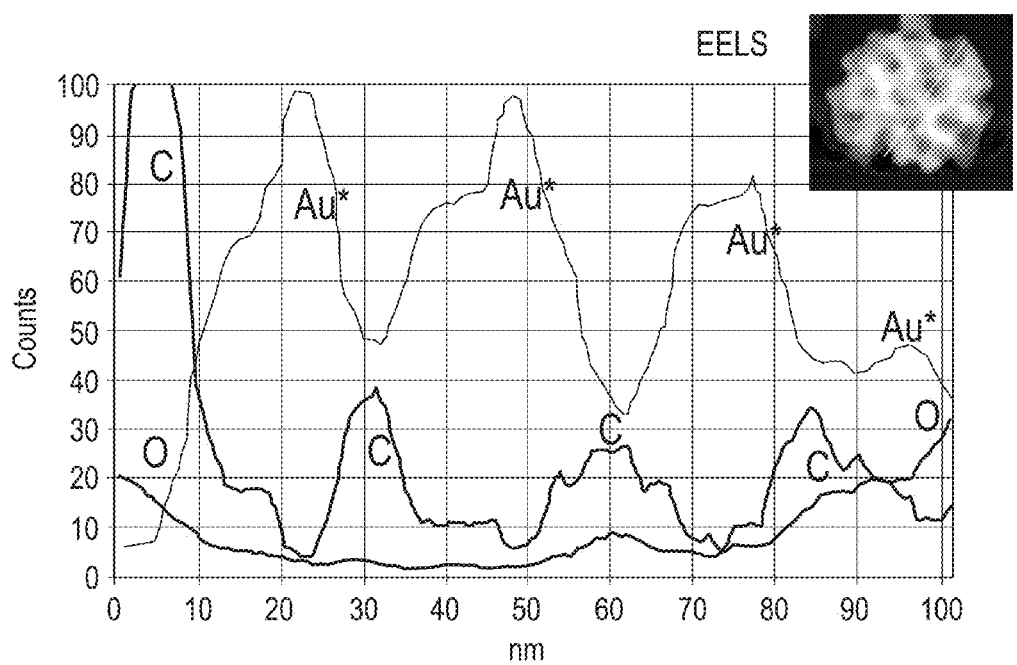
FIG. 8A is an electron energy loss spectrum (EELS) of AuNS-1 showing the presence of carbon, oxygen and gold in the sample.
Figure 8B:
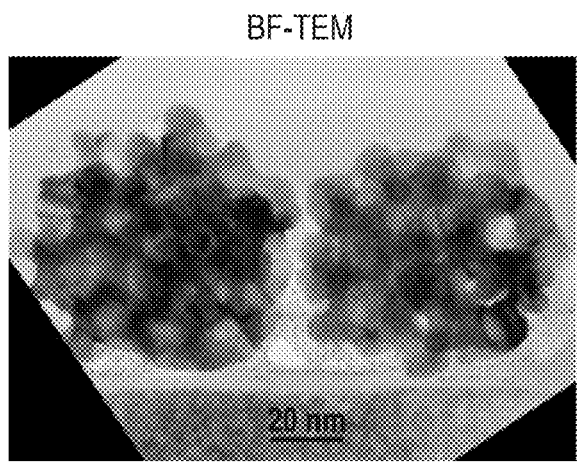
FIG. 8B is a bright field transmission electron micrograph (BF-TEM) showing the nodulous surface topography of AuNS-1 in greater magnification.
Figure 8C:
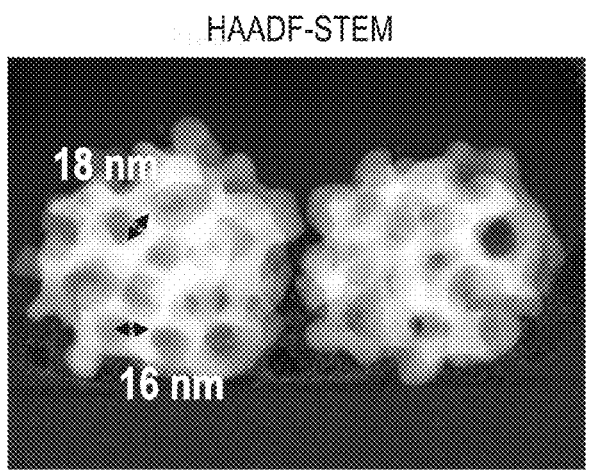
FIG. 8C is a high angle annular dark field micrograph obtained with a scanning transmission electron microscope (HAADF-STEM) of AuNS-1, which provides another topographical view of the AuNS-1 surface. The nodules have a diameter of about 18 nm and are spaced about 16 nm.
Figure 8D:
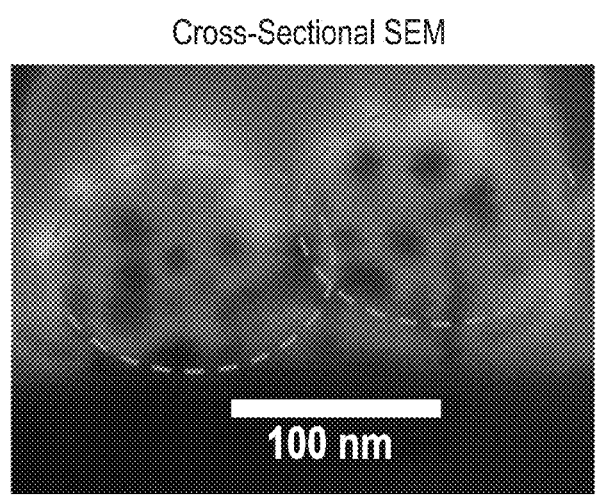
FIG. 8D is a cross-sectional scanning electron micrograph of AuNS-1 (cross-sectional sample produced using focusing ion beam (FIB) milling).

FIGS. 8A to 8D are images of obtained using various characterization techniques used on gold nanoshells AuNS-1. FIG. 8A is an electron energy loss spectrum (EELS) of AuNS-1 showing the periodic presence of carbon and gold in the sample along the line shown on the inserted image, confirming that the bright sections of the nanoparticle contain relatively high proportions of gold and the darker regions contain relatively higher proportions of carbon. The darker regions are approximately 16 nm to 18 nm in diameter. FIG. 8B is a bright field transmission electron micrograph (BF-TEM) showing the nodulous surface topography in greater magnification. FIG. 8C is a high angle annular dark field micrograph obtained with a scanning transmission electron microscope (HAADF-STEM), showing another detailed topographical view of the AuNS-1 nanoshell. The nodules have a diameter of about 18 nm and are spaced about 16 nm. FIG. 8D is a cross-sectional scanning electron micrograph of AuNS-1 (cross-sectional sample produced using focusing ion beam (FIB) milling).

Fluorescence of Gold Nanoshells.

Figure 9A:
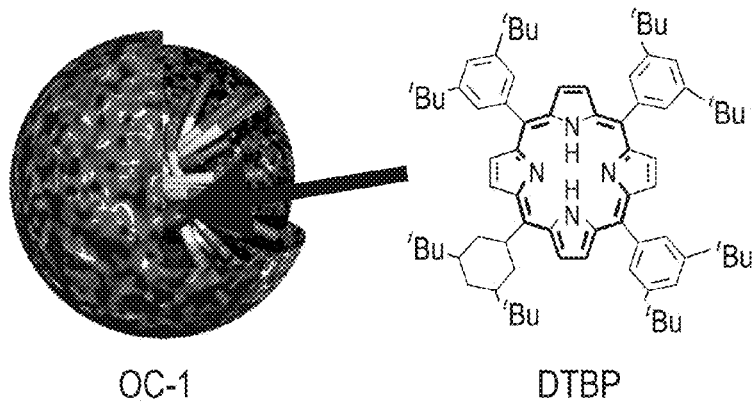
FIG. 9A is a graph showing the UV-VIS absorption spectra of star polymer occlusion complex OC-1 (single peak at 423 nm in water) and gold nanoshell AuNS-1 (peaks at 419 nm and 790 nm in water). OC-1 is represented by the three-dimensional drawing representation. OC-1 contains occluded porphyrin dye DTBP.
Figure 9A:
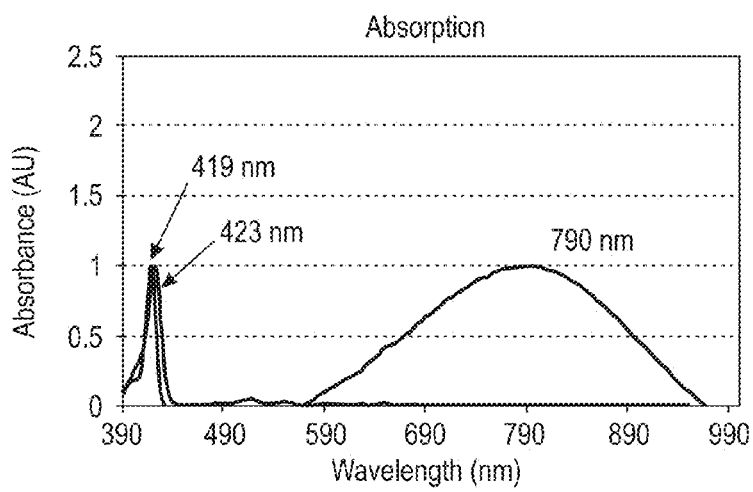
Figure 9B:
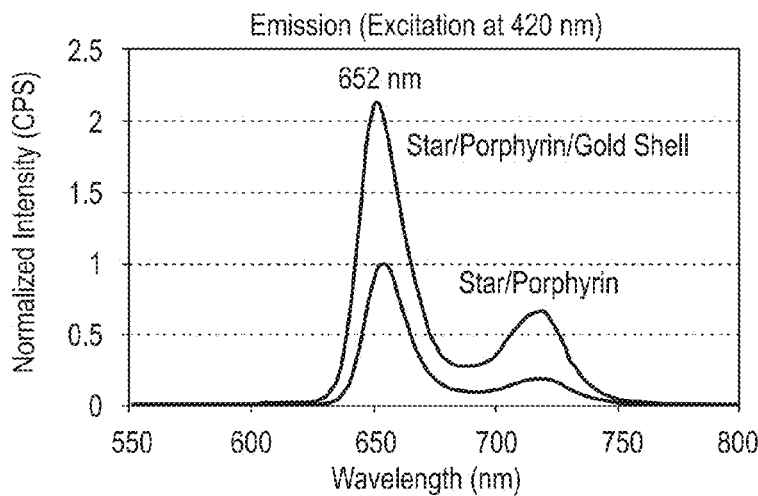
FIG. 9B is a graph comparing the fluorescence emission spectra of water solutions of OC-1 and gold nanoshell AuNS-1 for 420 nm excitation. The fluorescence of the occluded dye DTBP in the star polymer occlusion complex (lower curve) is similar to the fluorescence of the occluded dye DTBP in the gold nanoshell (upper curve). The dye is substantially in a non-aggregated state in the star polymer occlusion complex and the gold nanoshell.

FIG. 9A compares the UV-VIS absorption spectra of star polymer occlusion complex OC-1 (single peak at 423 nm) and gold nanoshell AuNS-1 (peaks at 419 nm and 790 nm). FIG. 9B compares the fluorescence emission spectra of OC-1 and gold nanoshell AuNS-1 for 420 nm excitation. The fluorescence of the occluded porphyrin dye in the occlusion complex is retained within the gold nanoshell. The dye is substantially in a non-aggregated state in the star polymer occlusion complex and the gold nanoshell.

II. Preparation of Silicon Nanoshells:

The disclosed star polymers can be engineered to have nucleation sites in their peripheries. Their ability to form occlusion complexes with a variety of organic dyes provides a versatile alternative template for the formation of structurally complex silicon based nanoshells.

Synthesis of Silicon Nanoshells Using "Two-Pot" Approach.

FIG. 10A illustrates with molecular models the "Two-Pot" approach to forming silicon nanoshells. In the first step, the appropriate star polymer (20 mg) and the porphyrin dye DTPB (2 mg) were dissolved in THF (20 microliters). An occlusion complex was made by adding this mixture drop wise to ethanol (4 mL) with rapid stirring. FIG. 10C is an atomic force microscope image (AFM) of the star polymer occlusion complex OC-4 (Z=10 nm) formed in this manner. This mixture was filtered using a poly(tetrafluoroethylene) (PTFE) filter (0.2 micrometers), and an aliquot (2 mL) was added to an aqueous solution of ammonium hydroxide (30% w/v) in ethanol (1:19 v/v, 20 mL). To this solution, 0.15 mL of a first silicon agent (e.g., TEOS) was added, and the reaction was stirred at room temperature for two hours. The reaction was not allowed to proceed beyond two hours in order to prevent aggregation of the particles. In step two, the reaction was stopped by the introduction of toluene (300 mL). The solvent volume was reduced under vacuum at 60° C., to a final volume of approximately 10 mL. A functionalized organosilane (e.g., hexamethyldisilazane (HMDS)) was then added (1.5 mL) and the reaction stirred for 16 hours at room temperature. The functionalized silicon nanoshell thus formed was purified by repeated dialysis against methanol (7 kDa cutoff). The hydroxyl group shown in FIG. 10A in step 1 represents the residual surface bound silanol OH groups of the nanoparticle's silicate nanoshell.

It is believed that the TEOS reacts with water (catalyzed by the ammonia and, presumably, by the amines of the star polymer) and begins to condense with itself. The silanol groups formed on the surface of the condensing material are relatively acidic compared to the amines found on the star polymer. Presumably the condensing material is soon electrostatically attracted to the star polymer at an early stage, thus "seeding" the star polymer prior to continued condensation of the TEOS.

EXAMPLE 10

Preparation of Silica Nanoshells, SiNS-1

The above "two pot" procedure was used to prepare silica nanoshells starting from star polymer occlusion complex OC-4 and HMDS as the functional organosilicate as described above. FIG. 10D is a TEM of the SiSN-1 showing a particle size of about 25 nm.

EXAMPLE 11 (COMPARISON)

Preparation of Solid Silica Particles

The two pot procedure was used without the star polymer occlusion complex to prepare solid silica particles as a comparison example. These particles are shown in FIG. 10E. The particle diameter ranges from about 50 nm to 250 nm.

Synthesis of Silica Nanoshells Using "One-Pot" Approach.

The "two pot" methodology was effective, but it was further optimized to a one pot version, where sample handling time was greatly reduced. Furthermore, when a more reactive silicon agent was used, the reaction time was also significantly reduced.

Figure 10B:
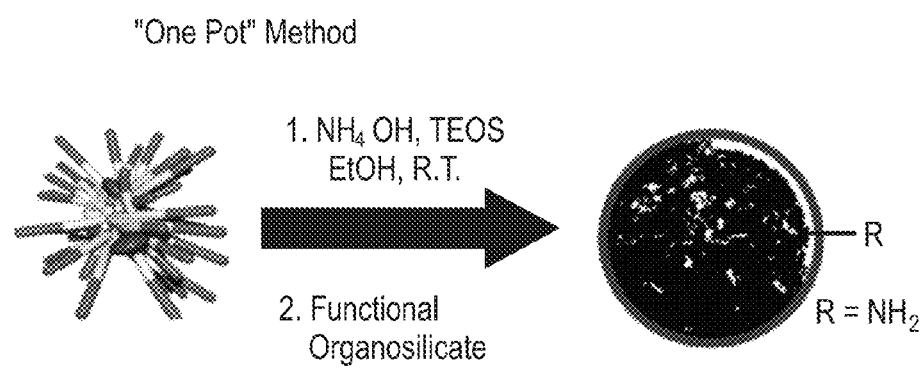
FIG. 10B is a schematic reaction diagram using three-dimensional drawing representations of the "One-Pot" method of forming silica nanoshells.
Figure 10C:
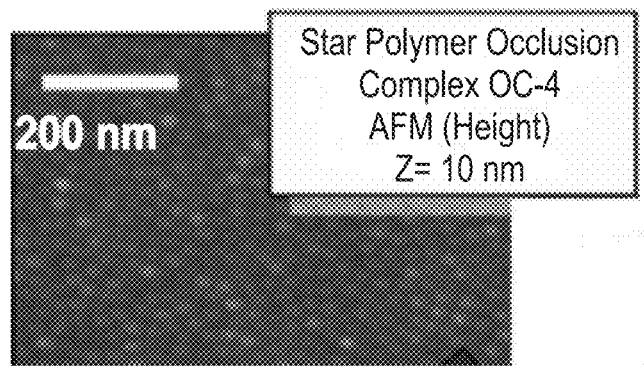
FIG. 10C is an atomic force microscope image (AFM) of the star polymer occlusion complex OC-4 (Z=10 nm) used in the preparation of silica nanoshells SiNS-1, using the "two-pot" method.
Figure 10D:
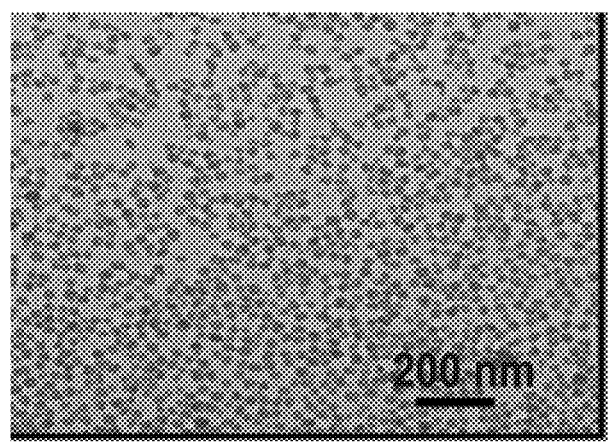
FIG. 10D is a transmission electron microscope image (TEM) of silica nanoshells SiNS-1.
Figure 10E:
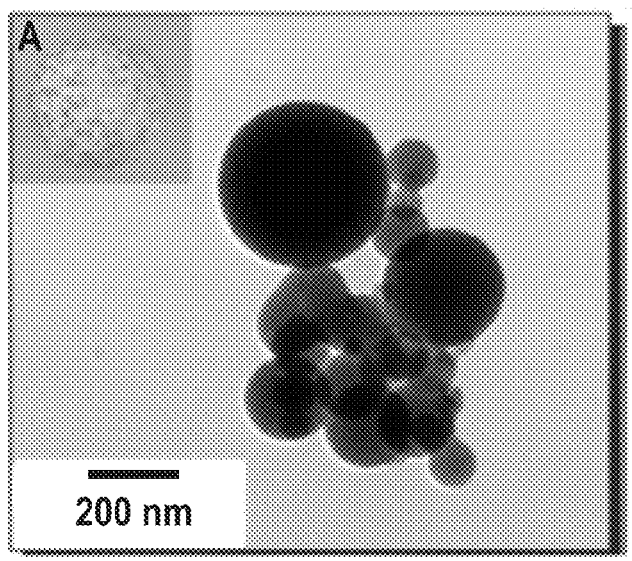
FIG. 10E is a TEM of comparison solid silica particles formed by the "two-pot" method without star polymer occlusion complex.

FIG. 10B illustrates with molecular models the "One-Pot" approach to forming silica nanoshells. In a general procedure, TEOS (21 microliters) was added to a 2 mL aliquot of the star polymer occlusion complex (as described above in the "two-pot" approach) in ethanol (20 mL) and the reaction mixture was stirred at room temperature for 3 hours. A functionalized organosilane (e.g., 3-aminoproplyldimethylethoxysilane) was added directly (12 microliters) and the reaction stirred for further 16 hours at room temperature. The functionalized silica nanoshells thus formed were purified by repeated dialysis against methanol (7 kDa cutoff). The amine group shown in FIG. 10B in step 1 represents the residual surface bound amine groups of the nanoparticle's shell formed when using 3-aminoproplyldimethylethoxysilane as the functionalized organosilane component in the reaction.

EXAMPLE 12

Preparation of Silica Nanoshell, SiSN-2, "One-Pot" Approach

Figure 10F:
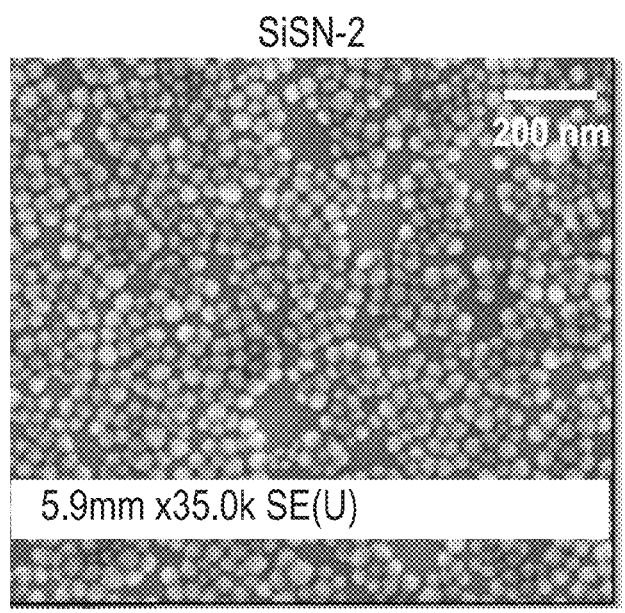
FIG. 10F is a TEM of the silica nanoshells SiNS-2, formed by the "one-pot" method.

The above described procedure was used to prepare silica nanoshells SiNS-2 using star polymer occlusion complex OC-4 and 3-aminoproplyldimethylethoxysilane as the functionalized organosilicate. FIG. 10F is a SEM of the SiSN-2 nanoshells, which have an average particle size of about 30 nm.

Size Control of Silica Nanoshells.

The following Examples 13 to 16 demonstrate that the particle size of the silica nanoshells can be controlled through coating time, coating reagent concentration and/or star polymer size (mixed examples derived from varying these parameters are shown).

EXAMPLE 13

Preparation of Silica Nanoshells, SiNS-3

Figure 11A:
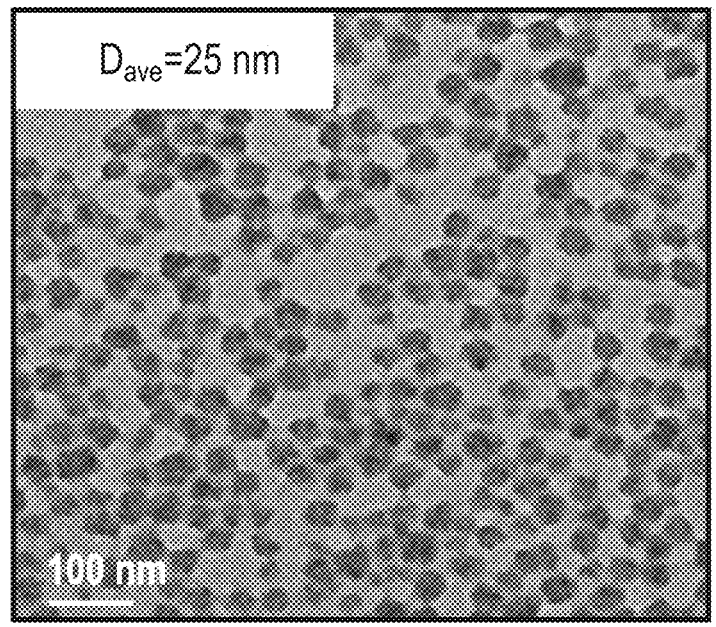
FIGS. 11A to 11D are a set of four TEMs of silica nanoshells SiNS-3 ($D_{ave}$=25 nm), SiNS-4 ($D_{ave}$=50 nm), SiNS-5 ($D_{ave}$=75 nm), and SiNS-6 ($D_{ave}$=100 nm), respectively, showing size control of silica nanoshells can be controlled through coating time, coating reagent concentration, and/or template size (mixed examples derived from varying these parameters are shown). The 25 nm particles were produced using the two-pot method. The 50 nm, 75 nm, and 100 nm particles were produced using the one pot method with extended reaction time and increasing amounts of ammonia in the reaction solution.

The two-pot method as described above for SiNS-1 was used to generate SiNS-3 using DPDS as the second organosilicate material. FIG. 11A is a TEM of the SiNS-3 nanoshells, which have an average particle size of about 25 nm.

EXAMPLE 14

Preparation of Silica Nanoshells, SiNS-4

Figure 11B:
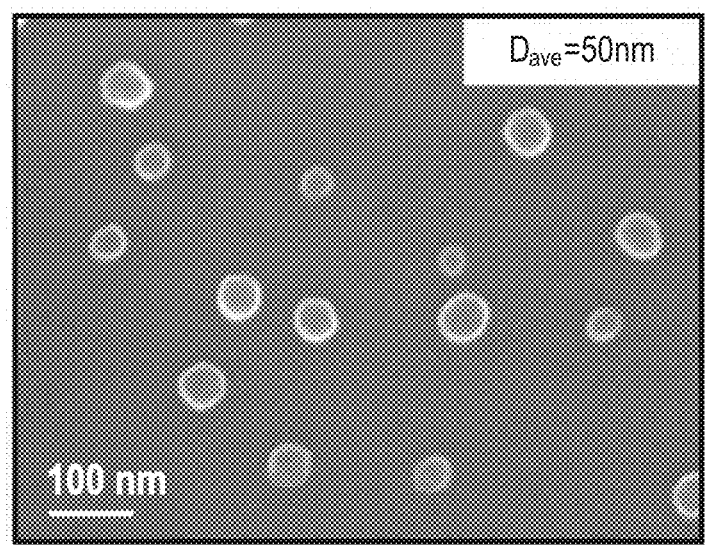

The one-pot method as described above was used to generate SiNS-4 using DPDS as the second organosilicate material and an extended reaction time. FIG. 11B is a TEM of the SiNS-4 nanoshells, which have an average particle size of about 50 nm.

EXAMPLE 15

Preparation of Silica Nanoshells, SiNS-5

Figure 11C:
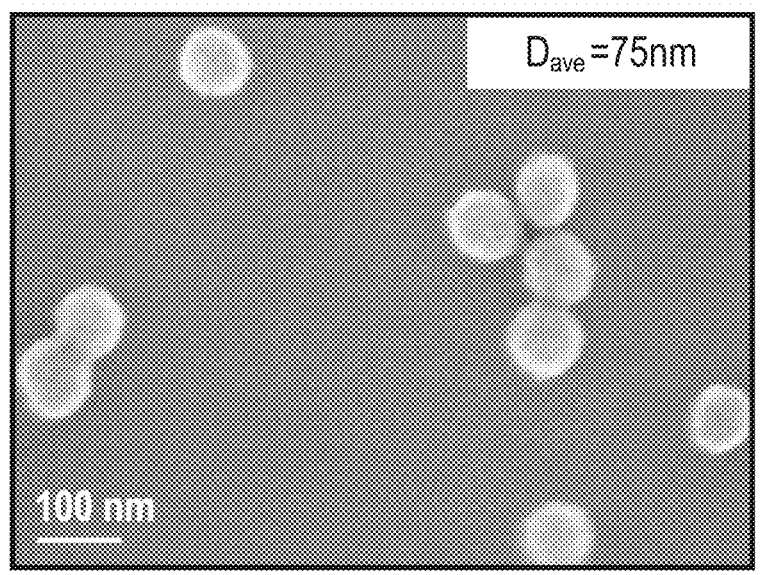

The one-pot method as described above was used to generate SiNS-5 using DPDS as the second organosilicate material and 1 ml of ammonium hydroxide solution. FIG. 11C is a TEM of the SiNS-5 nanoshells, which have an average particle size of about 75 nm.

EXAMPLE 16

Preparation of Silica Nanoshells, SiNS-6

Figure 11D:
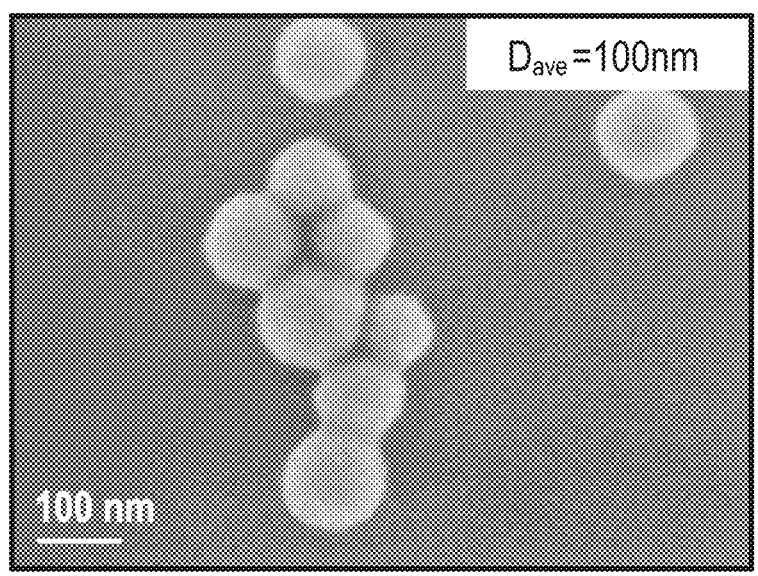

The one-pot method as described above was used to generate SiNS-2 using DPDS as the second organosilicate material and 1.15 ml of ammonium hydroxide solution. FIG. 11D is a TEM of the SiNS-6 nanoshells, which have an average particle size of about 100 nm.

The maximum time for the shell-forming reaction to be completed was two hours before aggregation took place. Therefore, a time line was created where a range of different sizes of silica nanoshells were produced.

Surface Tagging of Silica Nanoshells.

Figure 12A:
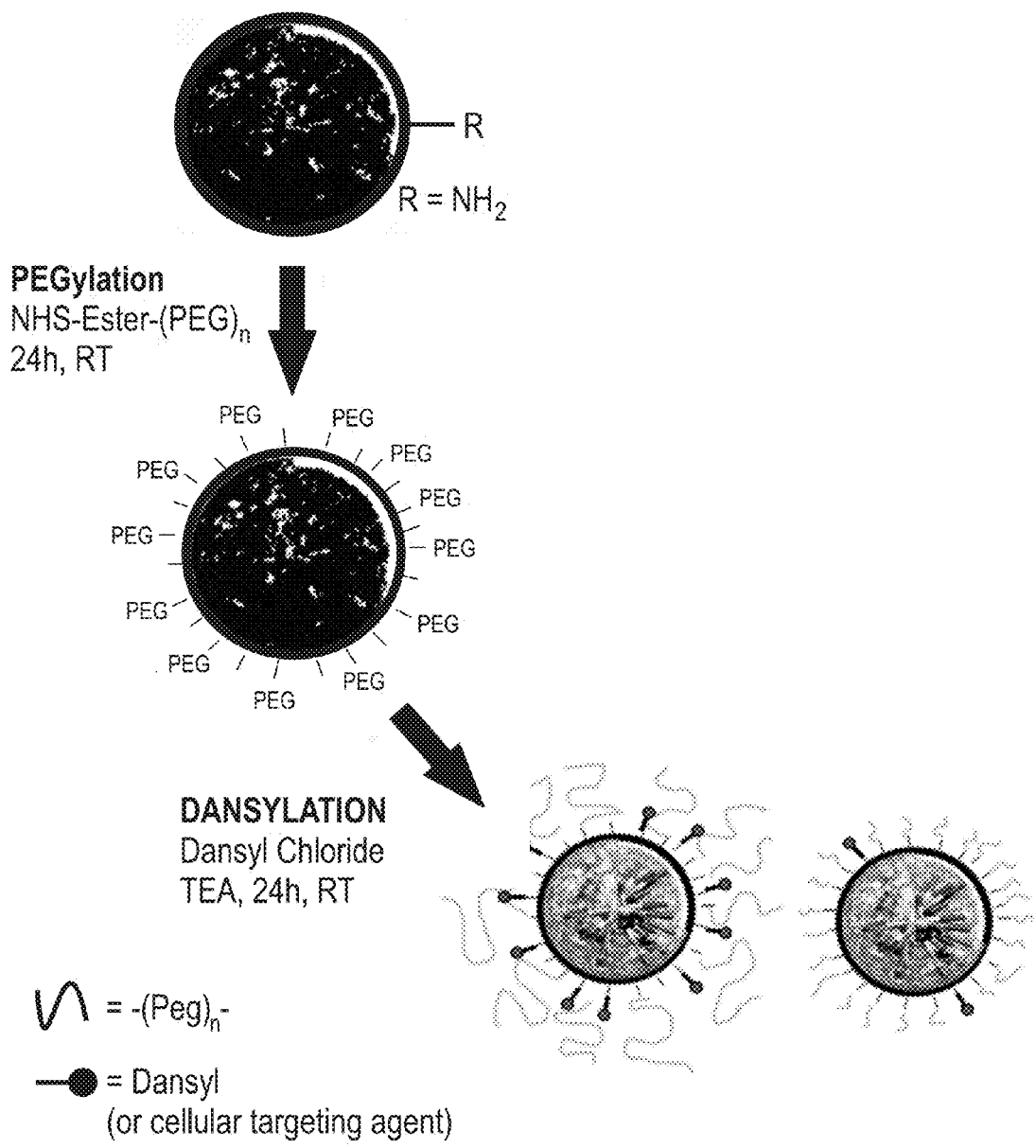
FIG. 12A is a schematic reaction diagram using three-dimensional drawing representations of the surface functionalization using organic tagging agents of silica nanoshell SiNS-2 that contains active primary amine surface groups. Four tagged silica nanoshells SiNS-7 to SiNS-10 (Examples 17 to 20) were formed using four different molecular weight alpha-methoxy-omega-carboxylic acid succinimidyl ester poly(ethylene glycol) as organic tagging agents. These are also referred to as PEGylating agents, which comprise a poly(ethylene glycol) (PEG) having a reactive succinimidyl ester end group, and are represented as "NHS-Ester-(PEG).

The following examples demonstrate surface tagging of silica nanoshells. Porphyrin occluded star polymers were coated with a silicon-containing shell in a one-pot process using TEOS and the surface of the particles was treated with aminopropyltrimethoxysilane (APTMS) to introduce surface amine groups. The resulting particles were surface tagged by sequential treatment with an alpha-methoxy-omega-carboxylic acid succinimidyl ester poly(ethylene glycol) and dansyl chloride as a representative cellular targeting agent. Surface functionalization was checked by comparing the dansyl and porphyrin components of the UV-VIS spectrum before and after extensive dialysis against water. FIG. 12A schematically shows the sequential tagging reactions.

EXAMPLE 17

Preparation of Tagged Silica Nanoshell, SiNS-7

Organic tagging agents can be used to modify the surface of the nanoshells. Amino-functionalized SiNS-2 (20 mg) was dissolved in a solution of dichloromethane and triethylamine (9:1) before the addition of alpha-methoxy-omega-carboxylic acid succinimidyl ester poly(ethylene glycol) having a PEG average molecular weight of 750 Da (0.2 g) as an organic tagging agent to the reaction solution. The reaction solution was then stirred at room temperature for 24 hours before the addition of dansyl chloride (0.2 g) as a second organic tagging agent and the reaction solution was then stirred for a further 24 hours before being purified by dialysis (MWCO=15 kDa) against MeOH and then water. The resulting solution was freeze dried to afford SiSN-7 as a powder.

EXAMPLE 18

Preparation of Tagged Silica Nanoshell, SiNS-8

The above described procedure for SiNS-7 was used to prepare tagged silica nanoshell, SiNS-8 using alpha-methoxy-omega-carboxylic acid succinimidyl ester poly(ethylene glycol) having a PEG average molecular weight of 2000 Da as the organic tagging agent.

EXAMPLE 19

Preparation of Tagged Silica Nanoshell, SiNS-9

The above described procedure for SiNS-7 was used to prepare tagged silica nanoshell, SiNS-9 using alpha-methoxy-omega-carboxylic acid succinimidyl ester poly(ethylene glycol) having a PEG chain average molecular weight of 5,000 Da as the organic tagging agent.

EXAMPLE 20

Preparation of Tagged Silica Nanoshell, SiNS-10

The above described procedure for SiNS-7 was used to prepare tagged silica nanoshell, SiNS-10 using alphamethoxy-omega-carboxylic acid succinimidyl ester poly(ethylene glycol) having a PEG average molecular weight of 10,000 Da as the organic tagging agent.

Figure 12B:
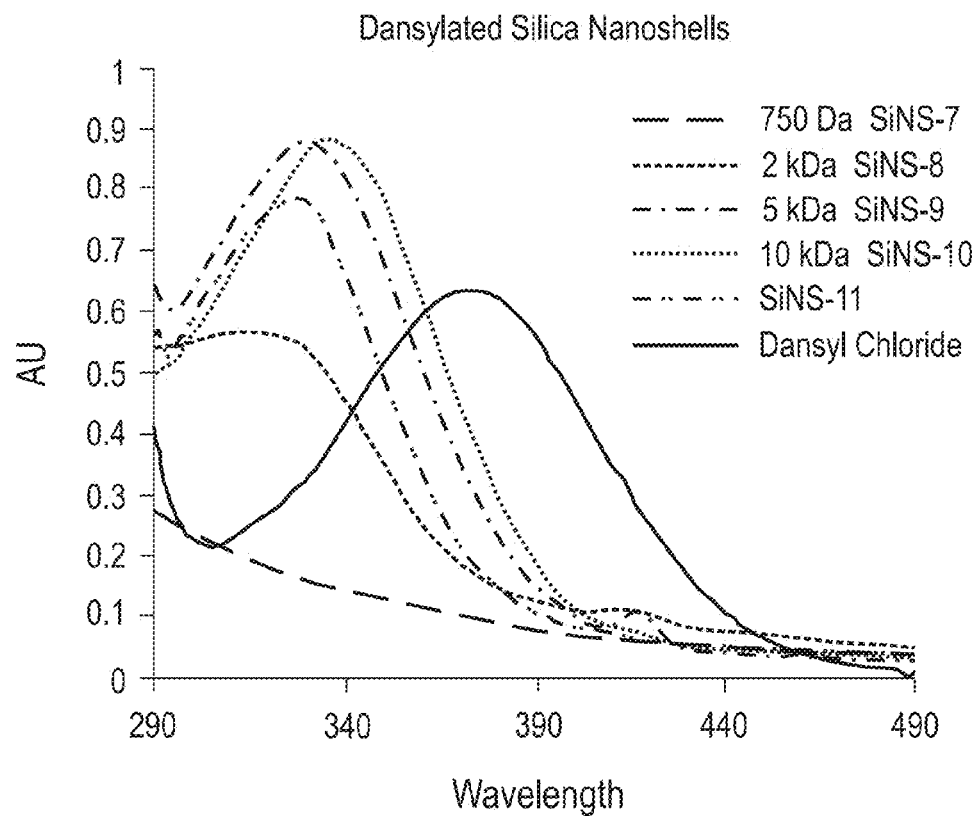
FIG. 12B is a graph comparing the UV-VIS absorbance of tagged silica nanoshells SiNS-7, SiNS-8, SiNS-9, and SiNS-10. SiNS-7, being fully covered by the smallest (least sterically demanding) PEG chain, is unable to react further with dansyl chloride and therefore has no significant absorption in the dansyl signature region. Increasing the PEG length used in forming SiNS-8, SiNS-9, SiNS-10 increases the number of residual surface amines available (owing to increasing steric demands of the surface bound PEG) to further react with small molecules such as dansyl chloride (hence increasing the absorbance in the signature dansyl region). This effect seems to be maximal for SiNS-9 which is similar to SiNS-10.
Figure 12C:
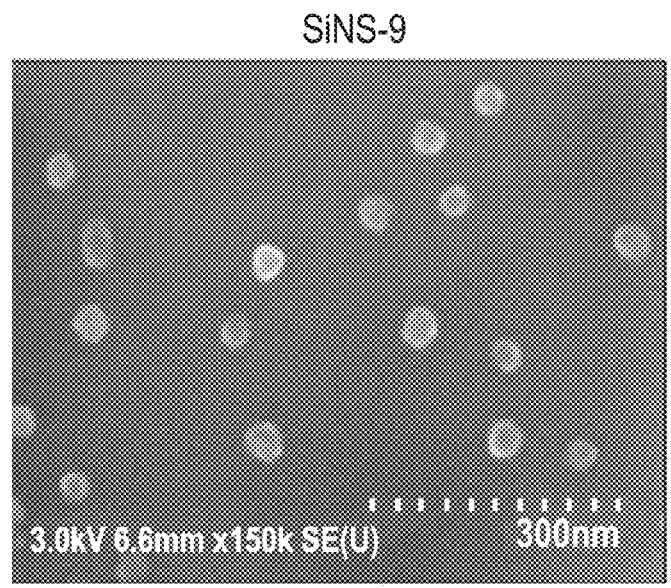
FIG. 12C is a TEM of dansyl tagged PEGylated silica nanoshells SiNS-9 (sample drop casted from aqueous solution before drying under ambient conditions).
Figure 12D:
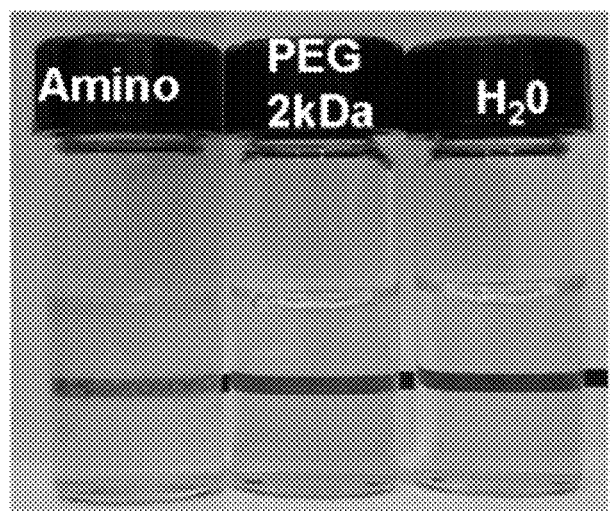
FIG. 12D is a photograph of three vials containing (from left to right) SiNS-2 (suspension in water), SiNS-8 (solution in water), and water (provided for reference).
Figure 12E:
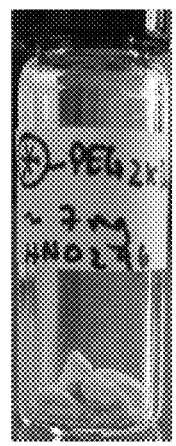
FIG. 12E is a photograph of a vial containing SiNS-8 as a lyophilized powder.

FIG. 12B compares the absorption curves of the PEGylated and dansylated silica nanoshells SiNS-7 to SiNS-10 (Examples 17 to 20). Dansyl chloride has a peak of about 380 nm whereas the dansylated silica nanoshells have peaks of about 320 nm to 340 nm. FIG. 12C is a TEM of tagged silica nanoshell SiNS-9 having an average particle size of about 30 nm to 40 nm. FIG. 12D is a photograph of aqueous solutions of the pre-tagged silica nanoshells (from left to right) SiNS-2 (left, suspension in water), tagged silica nanoshells SiNS-8 (middle, solution in water), water (right, provided for reference). FIG. 12E is a photograph of a vial containing SiNS-8 as a lyophilized powder.
Controlled Release.

The following examples demonstrate that if the dansylated silica nanoshells have a thin silicon-containing shell (20 nm particles), porphyrin can leak out of the tagged silica nanoshells, whereas if the silicon-containing shell is thick (30 nm particles), the porphyrin dye can be retained.

EXAMPLE 21

Preparation of Dansylated Silica Nanoshell, SiNS-11

Figure 13A:
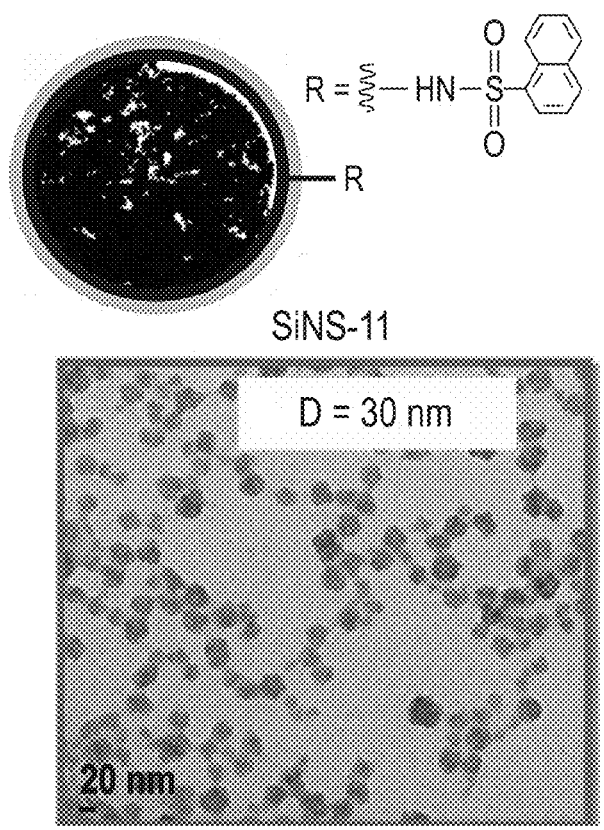
FIGS. 13A and 13B are TEMs of dansylated silica nanoshells SiNS-11 (average diameter 30 nm) and SiNS-12 (average diameter 20 nm), respectively. In this instance, a larger particle diameter indicates increased shell thickness.

The above described procedure for SiNS-2 was used to prepare the precursor silica nanoshell using extended reaction time to control the nanoshell thickness. The precursor nanoshell solution was solvent exchanged with dichlomethane via dialysis (MWCO=14 kDa) against dichloromethane before dansyl chloride (0.2 g) and triethylamine (0.2 mL) were added. The reaction solution was stirred at room temperature for 24 hours before being purified by dialysis (MWCO=15 kDa) against MeOH and then water. The nanoshells SiNS-11 had a diameter of 30 nm, as shown in the TEM of FIG. 13A.

EXAMPLE 22

Preparation of Tagged Silica Nanoshell, SiNS-12

Figure 13B:
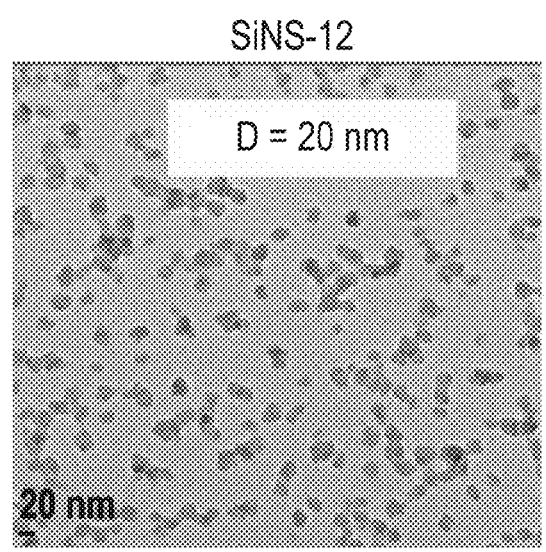

The above described procedure for SiNS-11 was used to prepare SiNS-12 using a reduced reaction time to control the nanoshell thickness. The SiNS-12 nanoshells had a diameter of 20 nm, as shown in the TEM of FIG. 13B.

Figure 13C:
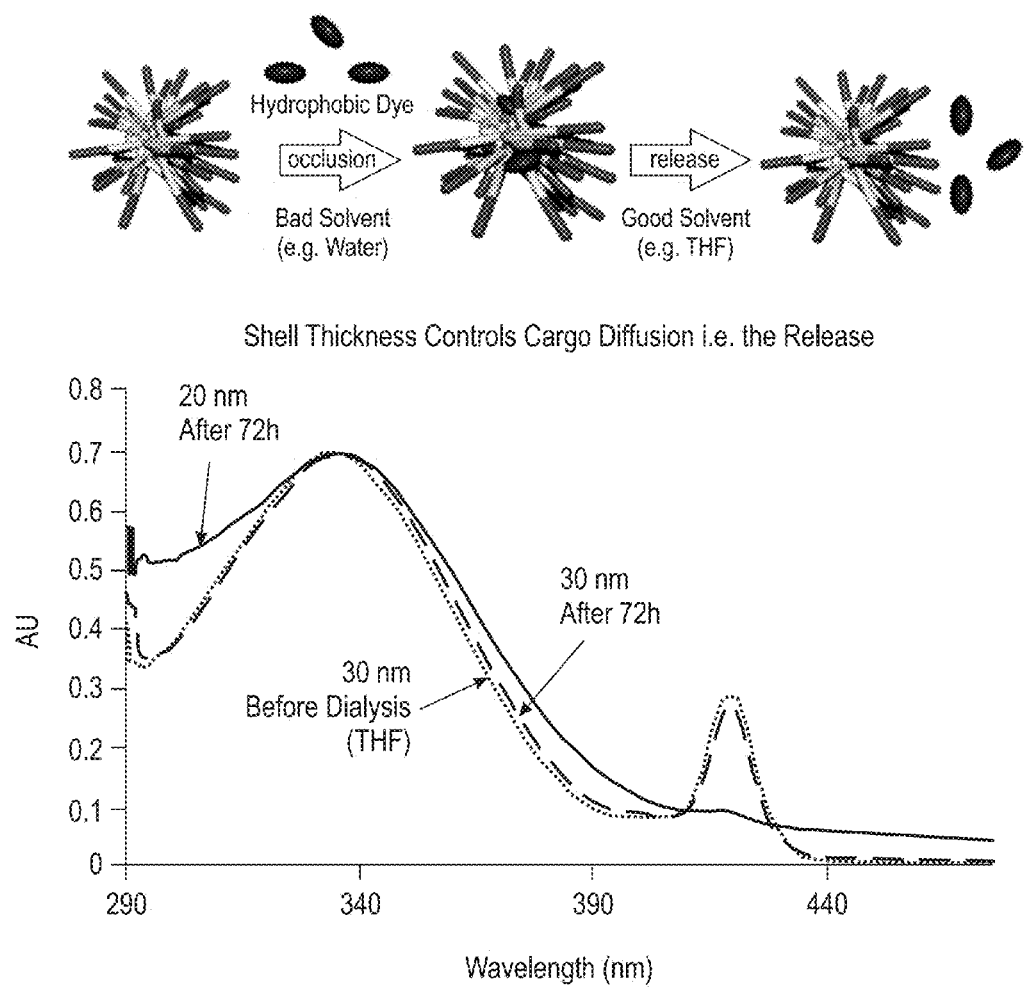
FIGS. 13C is a graph of the absorbance curves of dansylated silica nanoshells SiNS-11 and SiNS-12 after dialysis against tetrahydrofuran for 72 hours, demonstrating the controlled release rate of the occluded dye within the silica nanoshells varies with shell thickness. A shell thickness of 30 nm (SiNS-11) released almost no porphyrin dye (retention of peak at 420 nm), whereas the 20 nm shell thickness (SiNS-12) released substantially all of the porphyrin dye (loss of peak at 420 nm).

SiNS-11 and SiNS-12 were dialyzed against water (MWCO=14 kDa) for 72 hours. The absorption curves of FIG. 13C show that a shell thickness of 30 nm (SiNS-11) released almost no porphyrin dye (retention of peak at 420 nm), whereas the 20 nm shell thickness(SiNS-12) released substantially all of the porphyrin dye (loss of peak at 420 nm).
III. Preparation of Iron Oxide Nanoshells.

Iron oxide ($Fe_3O_4$, 6 nm) nanoparticles were synthesized from the thermal decomposition of iron(III)acetylacetone in benzyl ether in the presence of oleyl acid and oleyl amine, and the surfactant stabilized iron oxide nanoparticles were isolated by precipitation into hexane, as described by S. J. Sun et al., *J. Am. Chem. Soc.* 2004, 126, 273.

In a general procedure, a solution of the appropriate star polymer (20 mg), a hydrophobic porphyrin dye (2 mg) and the surfactant stabilized iron oxide nanoparticles (10 mg) were dissolved in THF (0.2 mL) and stirred at ambient temperature for 30 min before the solution was rapidly injected into water with rapid stirring. The aqueous solution thus formed was filtered though a 0.2 micrometer teflon filter and further purified by centrifugation.

EXAMPLE 23

Preparation of Iron Oxide Nanoshells SPIONNS-1

Figure 14A:
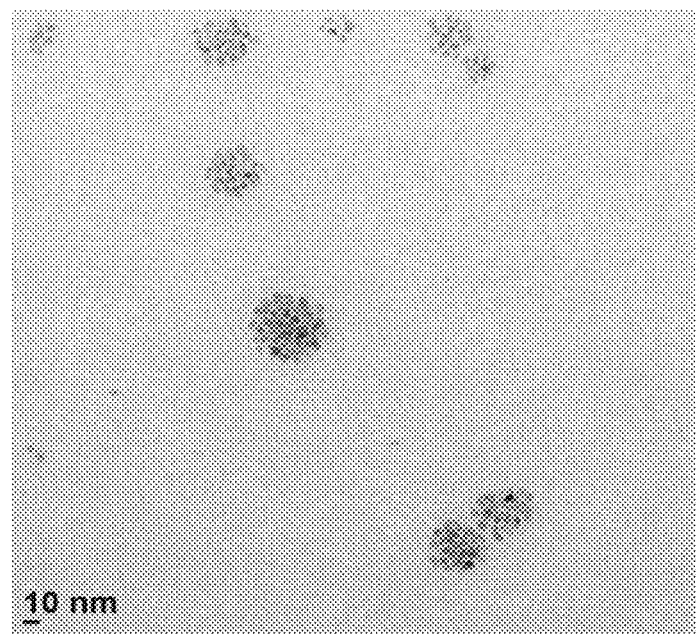
FIG. 14A is a TEM of iron oxide nanoshells SPIONNS-1.
Figure 14B:
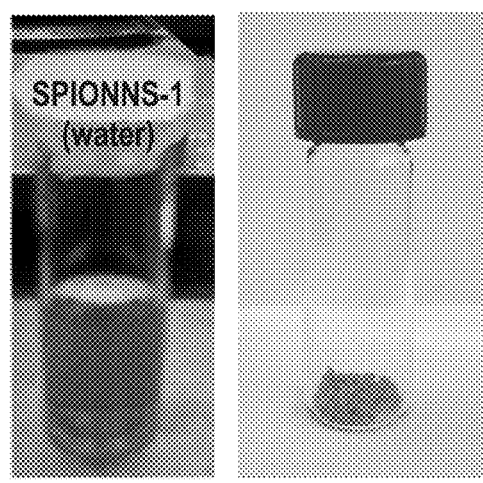
FIG. 14B is a pair of photographs of vials, the left vial containing an aqueous solution of SPIONNS-1 having a rust orange hue, and the right vial containing a brown colored lyophilized powder of SPIONNS-1.
Figure 14C:
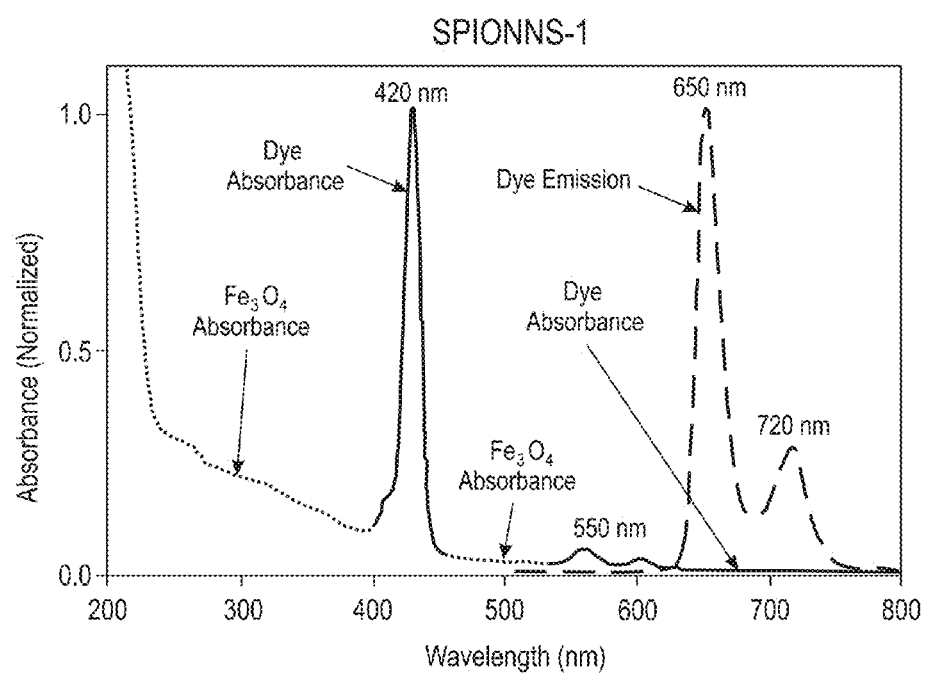
FIG. 14C is a graph of the UV-VIS absorbance (left) and emission from excitation at 420 nm (right) of an aqueous solution of SPIONNS-1.

The above described procedure using star polymer SP-1 was used to produce an iron oxide nanoshell SPIONNS-1 in water. FIG. 14A is a TEM of SPIONNS-1. FIG. 14B is a pair of photographs of SPIONNS-1 as an aqueous solution having a rust orange hue (left) and a brown colored lyophilized powder (right). The solution has UV-VIS peaks at 420 nm and 550 nm, and emission peaks (for excitation at 420 nm) of 650 nm and 720 nm, as shown in the absorption curve of FIG. 14C.

Without being bound by theory, it is believed that the self-assembly processes producing the occluded dye component and the shell component can be effected in tandem. The hydrophobic dyes are held inside the star polymer to form an occlusion complex wherein the polymer structure shields the dye to some extent from the external environment. Additionally, the iron oxide nanoparticles are believed to be bound to the periphery of the polymer to form a nanoshell which to some extent shield the polymer from the external environment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:
1. A nanoshell, comprising:
    a star polymer occlusion complex comprising i) an amphiphilic unimolecular star polymer having a crosslinked polymer core covalently linked to 6 or more independent polymer arms, and ii) a cargo material occluded in the star polymer; and
    a shell comprising iron oxide, the shell exterior to and in contact with a peripheral surface of the star polymer occlusion complex;
    wherein the crosslinked polymer core is a product of a vinyl polymerization and/or a ring opening polymerization.
2. The nanoshell of claim 1, wherein i) the core is hydrophobic, ii) the cargo material is hydrophobic, and iii) each of the 6 or more polymer arms comprises a) a hydro- phobic chain segment covalently linked to the core and b) a peripheral hydrophilic chain segment linked to the hydrophobic chain segment.

3. The nanoshell of claim 1, wherein an aqueous mixture of the nanoshell is suitable for diagnostic imaging.

4. The nanoshell of claim 1, wherein the shell comprises one or more shell layers.

5. The nanoshell of claim 4, wherein the one or more shell layers are porous.

6. The nanoshell of claim 1, wherein the nanoshell has an average diameter of about 15 nm to about 300 nm.

7. The nanoshell of claim 1, wherein the cargo material is an imaging agent.

8. The nanoshell of claim 1, wherein the cargo material is a biologically active compound.

9. The nanoshell of claim 1, wherein the star polymer comprises a polycarbonate chain segment, a polyester chain segment, or a combination thereof.

10. The nanoshell of claim 1, further comprising an organic surface group covalently linked to the shell, the organic surface group comprising a chemical moiety selected from the group consisting of dyes, poly(alkylene oxide) chain segments, poly(alkylene imine) chain segments, biologically active moieties, and combinations thereof.

11. A method of forming the nanoshell of claim 1, comprising:
   forming a mixture containing a star polymer occlusion complex and iron oxide in a suitable solvent, the star polymer occlusion complex comprising i) an amphiphilic unimolecular star polymer having a crosslinked polymer core covalently linked to 6 or more independent polymer arms, and ii) a cargo material occluded in the star polymer; and
   injecting the mixture into a second solvent, the second solvent being a non-solvent for the cargo material, thereby forming the nanoshell.

12. The method of claim 11, wherein i) the core is hydrophobic, ii) the cargo material is hydrophobic, and iii) each of the 6 or more polymer arms comprises a) a hydrophobic chain segment covalently linked to the core and b) a peripheral hydrophilic chain segment linked to the hydrophobic chain segment.

13. The method of claim 11, wherein the nanoshell has an average diameter of about 15 nm to about 300 nm.

14. The method of claim 11, wherein the cargo material is an imaging agent.

15. The method of claim 11, wherein the cargo material is a biologically active compound.

16. A tagged silica nanoshell, comprising:
   a star polymer occlusion complex comprising i) an amphiphilic unimolecular star polymer having a crosslinked polymer core covalently linked to 6 or more independent polymer arms and ii) a cargo material occluded in the star polymer, wherein the crosslinked polymer core is a product of a vinyl polymerization and/or a ring opening polymerization;
   a shell comprising silica, the shell exterior to and in contact with a peripheral surface of the star polymer occlusion complex; and
   an organic surface group comprising a poly(alkylene oxide) chain segment covalently linked to the shell.

17. The tagged silica nanoshell of claim 16, wherein i) the core is hydrophobic, ii) the cargo material is hydrophobic, and iii) each of the 6 or more polymer arms comprises a) a hydrophobic chain segment covalently linked to the core and b) a peripheral hydrophilic chain segment linked to the hydrophobic chain segment.

18. The tagged silica nanoshell of claim 16, wherein an aqueous mixture of the tagged silica nanoshell is suitable for diagnostic imaging.

19. The tagged silica nanoshell of claim 16, comprising a second organic surface group covalently linked to the shell, the second organic surface group comprising a chemical moiety selected from the group consisting of dyes, poly(alkylene imine) chain segments, biologically active moieties, and combinations thereof.

20. The tagged silica nanoshell of claim 16, wherein the tagged silica nanoshell has an average diameter of about 15 nm to about 300 nm.

21. A method of forming the tagged silica nanoshell of claim 16, comprising:
   treating a star polymer occlusion complex with a first tetravalent silicon material, thereby forming a precursor silica nanoshell, wherein i) the star polymer occlusion complex comprises an amphiphilic unimolecular star polymer and a cargo material occluded therein, the star polymer having a crosslinked polymer core covalently linked to 6 or more independent polymer arms and ii) the crosslinked polymer core is a product of a vinyl polymerization and/or a ring opening polymerization;
   treating the precursor nanoshell with a second tetravalent silicon material comprising a nucleophilic group, thereby forming a silica nanoshell comprising a shell which is exterior to and in contact with a peripheral surface of the star polymer occlusion complex, wherein the shell comprises i) silica and ii) nucleophilic surface groups selected from the group consisting of amines, thiols, alcohols, and combinations thereof; and
   covalently linking to a nucleophilic surface group of the shell an organic surface group comprising a poly(alkylene oxide) chain segment, thereby forming the tagged silica nanoshell.

22. The method of claim 21, wherein i) the core is hydrophobic, ii) the cargo material is hydrophobic, and iii) each of the 6 or more polymer arms comprises a) a hydrophobic chain segment covalently linked to the core and b) a peripheral hydrophilic chain segment linked to the hydrophobic chain segment.

23. The method of claim 21, further comprising covalently linking to the shell a second organic surface group comprising a chemical moiety selected from the group consisting of dyes, poly(alkylene imine) chain segments, biologically active moieties, and combinations thereof.

* * * * *